US012686847B2

(12) United States Patent
Janousek et al.

(10) Patent No.: US 12,686,847 B2
(45) Date of Patent: Jul. 21, 2026

(54) CULTURE MEDIA BASED ON PROTEIN HYDROLYSATE AND A PROCESS FOR PREPARING THEREOF

(71) Applicant: BTL Healthcare Technologies a.s., Prague (CZ)

(72) Inventors: Jiri Janousek, Jilove u Prahy (CZ); Sara Sediva, Prague (CZ); Marketa Veresova, Prague (CZ); Katerina Hermanova, Prague (CZ); Anna Kohoutova, Prague (CZ)

(73) Assignee: BTL Healthcare Technologies a.s., Prague (CZ)

( * ) Notice: Subject to any disclaimer, the term of this patent is extended or adjusted under 35 U.S.C. 154(b) by 0 days.

(21) Appl. No.: 19/029,060

(22) Filed: Jan. 17, 2025

(65) Prior Publication Data

US 2025/0215389 A1      Jul. 3, 2025

Related U.S. Application Data

(63) Continuation of application No. PCT/IB2024/053805, filed on Apr. 18, 2024.

(60) Provisional application No. 63/497,051, filed on Apr. 19, 2023.

(51) Int. Cl.
*C12N 5/00* (2006.01)
*A23L 13/00* (2016.01)
*C12P 21/06* (2006.01)

(52) U.S. Cl.
CPC ........ *C12N 5/0018* (2013.01); *C12N 2500/12* (2013.01); *C12N 2500/24* (2013.01); *C12N 2500/32* (2013.01); *C12N 2500/34* (2013.01); *C12N 2500/46* (2013.01)

(58) Field of Classification Search
CPC .............. C12N 5/0018; C12N 2500/12; C12N 2500/24; C12N 2500/32; C12N 2500/34; C12N 2500/46
See application file for complete search history.

(56) References Cited

U.S. PATENT DOCUMENTS

| | | | |
|---|---|---|---|
| 922,075 | A | 5/1909 | Bates |
| 1,087,094 | A | 2/1914 | Berrigan |
| 4,642,238 | A | 2/1987 | Lin |
| 5,541,102 | A | 7/1996 | Donis |
| 5,607,840 | A | 3/1997 | Van Gorp |
| 5,607,854 | A | 3/1997 | Prahl |
| 6,338,866 | B1 | 1/2002 | Criggall |
| 6,403,142 | B1 | 6/2002 | McDaniel, III |
| 6,537,597 | B1 | 3/2003 | Nakamori |
| 6,537,782 | B1 | 3/2003 | Shibuya |
| 6,783,792 | B2 | 8/2004 | McDaniel, III |
| 6,821,534 | B2 | 11/2004 | McDaniel, III |
| 6,855,365 | B2 | 2/2005 | Short |
| 6,897,040 | B2 | 5/2005 | Morris |
| 6,962,812 | B2 | 11/2005 | Shibuya |
| 7,078,035 | B2 | 7/2006 | Short |
| 7,115,385 | B2 | 10/2006 | Breitschwerdt |
| 7,166,445 | B2 | 1/2007 | Morris |
| 7,232,677 | B2 | 6/2007 | Short |
| 7,416,874 | B2 | 8/2008 | Short |
| 7,432,097 | B2 | 10/2008 | Short |
| 7,432,098 | B2 | 10/2008 | Short |
| 7,442,548 | B2 | 10/2008 | Thomson |
| 7,449,334 | B2 | 11/2008 | Thomson |
| 7,452,706 | B2 | 11/2008 | Short |
| 7,456,019 | B2 | 11/2008 | Goodwin |
| 7,465,470 | B2 | 12/2008 | Saito |
| 7,553,665 | B2 | 6/2009 | Aloni |
| 7,563,769 | B2 | 7/2009 | Bogin |
| 7,592,175 | B2 | 9/2009 | Amit |
| 7,604,829 | B2 | 10/2009 | Schopf |
| 7,628,528 | B2 | 12/2009 | Zeikus |
| 7,662,615 | B2 | 2/2010 | Chang |
| 7,749,756 | B2 | 7/2010 | Leonhartsberger |
| 7,807,176 | B2 | 10/2010 | Nishikawa |
| 7,816,140 | B2 | 10/2010 | Lau |
| 7,819,576 | B2 | 10/2010 | Zeikus |
| 7,824,895 | B2 | 11/2010 | Short |
| 7,863,031 | B2 | 1/2011 | Short |
| 7,879,377 | B2 | 2/2011 | Dahl |
| 7,897,379 | B2 | 3/2011 | Kenney |
| 7,939,495 | B2 | 5/2011 | Chung |
| 7,955,833 | B2 | 6/2011 | Reiter |
| 7,955,851 | B2 | 6/2011 | Amit |
| 7,977,096 | B2 | 7/2011 | Nistor |
| 8,012,931 | B2 | 9/2011 | Cujec |

(Continued)

FOREIGN PATENT DOCUMENTS

| CA | 3231125 A1 | 4/2023 |
|---|---|---|
| CA | 3275968 A1 | 6/2024 |

(Continued)

OTHER PUBLICATIONS

Marson et al., (2020) Proteolytic enzymes positively modulated the physiocochemical and antioxidant properties of spent yeast protein hydrolysates. Process biochemistry, 91: pp. 34-35 (Year: 2020).*
R. Ian Freshney, "Defined Media and Supplements", "Serum-Free Media", "Preparation and Sterilization". In: Culture of Animal Cell: A Manual of Basic Technique and Specialized Applications. (Hoboken, NJ, John Wiley & Sons, Inc., 2010), pp. 99-132. QH585.2. F74 2010 (Year: 2010).*
Jacob, Friedrich Felix, et al. "Spent yeast from brewing processes: a biodiverse starting material for yeast extract production." Fermentation 5.2 (2019): 51. 19 pages.
Jacob, Friedrich Felix, Mathias Hutzler, and Frank-Jürgen Methner. "Comparison of various industrially applicable disruption methods to produce yeast extract using spent yeast from top-fermenting beer production: influence on amino acid and protein content." European Food Research and Technology 245 (2019): 95-109.

(Continued)

*Primary Examiner* — Kara D Johnson
(74) *Attorney, Agent, or Firm* — Riverside Law LLP

(57) ABSTRACT

The present invention provides culture media and method for the cultivation of non-human metazoan cells for preparing a food product.

30 Claims, 1 Drawing Sheet

(56)                References Cited

U.S. PATENT DOCUMENTS

| | | | |
|---|---|---|---|
| 8,034,770 B2 | 10/2011 | Belouski |
| 8,043,614 B2 | 10/2011 | Ahlfors |
| 8,067,171 B2 | 11/2011 | Khatibm |
| 8,076,300 B2 | 12/2011 | Presta |
| 8,080,265 B2 | 12/2011 | Kizoulis |
| 8,114,646 B2 | 2/2012 | Martin |
| 8,119,783 B2 | 2/2012 | Bogin |
| 8,158,424 B2 | 4/2012 | Thomson |
| 8,188,040 B2 | 5/2012 | Belouski |
| 8,211,697 B2 | 7/2012 | Sakurada |
| 8,222,034 B2 | 7/2012 | Amit |
| 8,236,527 B2 | 8/2012 | Chen |
| 8,252,557 B2 | 8/2012 | Katayama |
| 8,257,941 B2 | 9/2012 | Sakurada |
| 8,318,465 B2 | 11/2012 | Filho |
| 8,343,918 B2 | 1/2013 | Glass |
| 8,361,963 B2 | 1/2013 | Belouski |
| 8,383,365 B2 | 2/2013 | Cujec |
| 8,398,932 B2 | 3/2013 | Busujima |
| 8,410,051 B2 | 4/2013 | Belouski |
| 8,426,203 B2 | 4/2013 | Thomson |
| 8,440,408 B2 | 5/2013 | Grillberger |
| 8,470,552 B2 | 6/2013 | Croughan |
| 8,524,497 B2 | 9/2013 | Reiter |
| 8,563,311 B2 | 10/2013 | Amit |
| 8,569,050 B1 | 10/2013 | Ericsson |
| 8,569,061 B2 | 10/2013 | Nistor |
| 8,609,823 B2 | 12/2013 | Bogin |
| 8,618,053 B2 | 12/2013 | Belouski |
| 8,628,815 B2 | 1/2014 | Torney |
| 8,642,546 B2 | 2/2014 | Belouski |
| 8,672,245 B2 | 3/2014 | Finnigan |
| 8,722,621 B2 | 5/2014 | Glass |
| 8,748,156 B2 | 6/2014 | Grillberger |
| 8,759,299 B2 | 6/2014 | Dong |
| 8,771,988 B2 | 7/2014 | Goepfert |
| 8,772,571 B2 | 7/2014 | Lau |
| 8,790,913 B2 | 7/2014 | Zeikus |
| 8,795,985 B2 | 8/2014 | Belouski |
| 8,828,719 B2 | 9/2014 | Cain |
| 8,835,385 B2 | 9/2014 | Belouski |
| 8,835,604 B2 | 9/2014 | Hoegenhaug |
| 8,853,374 B2 | 10/2014 | Inouye |
| 8,859,280 B2 | 10/2014 | Gardner |
| 8,877,478 B2 | 11/2014 | Steer |
| 8,894,756 B2 | 11/2014 | Galliher |
| 8,916,522 B2 | 12/2014 | Bogin |
| 8,936,924 B2 | 1/2015 | Solbak |
| 8,940,860 B2 | 1/2015 | Dimarchi |
| 8,945,925 B2 | 2/2015 | Amit |
| 8,951,784 B2 | 2/2015 | Gould |
| 8,962,290 B2 | 2/2015 | Chen |
| 8,962,556 B2 | 2/2015 | Yayon |
| 8,980,844 B2 | 3/2015 | Chung |
| 8,998,793 B2 | 4/2015 | Oatley |
| 8,999,929 B2 | 4/2015 | Mohammadi |
| 9,005,942 B2 | 4/2015 | Chen |
| 9,006,400 B2 | 4/2015 | Boettcher |
| 9,012,192 B2 | 4/2015 | Chen |
| 9,018,010 B2 | 4/2015 | Amit |
| 9,045,733 B2 | 6/2015 | Chen |
| 9,079,971 B2 | 7/2015 | Cujec |
| 9,085,785 B2 | 7/2015 | Reed |
| 9,109,193 B2 | 8/2015 | Galliher |
| 9,127,242 B2 | 9/2015 | Guertin |
| 9,149,056 B2 | 10/2015 | Zhang |
| 9,157,058 B2 | 10/2015 | Dalla-Betta |
| 9,163,211 B2 | 10/2015 | Reiter |
| 9,169,309 B2 | 10/2015 | Jeong |
| 9,174,181 B2 | 11/2015 | Kocourek |
| 9,213,999 B2 | 12/2015 | Sakurada |
| 9,217,130 B2 | 12/2015 | Hashimoto |
| 9,234,210 B2 | 1/2016 | Famili |
| 9,266,935 B2 | 2/2016 | Boettcher |
| 9,272,251 B2 | 3/2016 | Jones |
| 9,273,106 B2 | 3/2016 | Belouski |
| 9,273,278 B2 | 3/2016 | Lee |
| 9,273,292 B2 | 3/2016 | Song |
| 9,279,103 B2 | 3/2016 | Chen |
| 9,279,107 B2 | 3/2016 | Chen |
| 9,315,565 B2 | 4/2016 | Cain |
| 9,321,995 B2 | 4/2016 | Liu |
| 9,332,779 B2 | 5/2016 | Marga |
| 9,340,814 B2 | 5/2016 | Sasaki |
| 9,345,254 B2 | 5/2016 | Samoto |
| 9,359,617 B2 | 6/2016 | Francky |
| 9,382,515 B2 | 7/2016 | Jaenisch |
| 9,388,375 B2 | 7/2016 | Brau |
| 9,410,121 B2 | 8/2016 | Amit |
| 9,428,727 B2 | 8/2016 | Leist |
| 9,428,766 B2 | 8/2016 | Goepfert |
| 9,434,778 B2 | 9/2016 | Morin |
| 9,434,922 B2 | 9/2016 | Oatley |
| 9,439,874 B2 | 9/2016 | Weng |
| 9,453,194 B2 | 9/2016 | Zeikus |
| 9,458,215 B2 | 10/2016 | Lau |
| 9,458,220 B2 | 10/2016 | Dimarchi |
| 9,464,126 B2 | 10/2016 | Mohammadi |
| 9,474,785 B2 | 10/2016 | Mohammadi |
| 9,476,081 B2 | 10/2016 | Cain |
| 9,480,809 B2 | 11/2016 | Guney |
| 9,487,568 B2 | 11/2016 | Bogin |
| 9,487,572 B2 | 11/2016 | Weiss |
| 9,493,530 B2 | 11/2016 | Belouski |
| 9,506,086 B2 | 11/2016 | Jannson |
| 9,517,273 B2 | 12/2016 | Cujec |
| 9,573,987 B2 | 2/2017 | Dimarchi |
| 9,585,412 B2 | 3/2017 | Corrigan |
| 9,593,156 B2 | 3/2017 | Dimarchi |
| 9,631,004 B2 | 4/2017 | Morin |
| 9,637,557 B2 | 5/2017 | Scheer |
| 9,637,717 B2 | 5/2017 | Lee |
| 9,643,133 B2 | 5/2017 | Goodwin |
| 9,644,186 B2 | 5/2017 | Chen |
| 9,657,075 B2 | 5/2017 | Mohammadi |
| 9,670,446 B2 | 6/2017 | Khan |
| 9,670,504 B2 | 6/2017 | Miller |
| 9,670,519 B2 | 6/2017 | Srivastava |
| 9,695,403 B2 | 7/2017 | Weiner |
| 9,714,411 B2 | 7/2017 | Grillberger |
| 9,714,414 B2 | 7/2017 | Jaenisch |
| 9,714,433 B2 | 7/2017 | Sakurada |
| 9,738,692 B2 | 8/2017 | Inouye |
| 9,745,359 B2 | 8/2017 | Qin |
| 9,758,568 B2 | 9/2017 | Grillberger |
| 9,783,771 B2 | 10/2017 | Khan |
| 9,803,168 B2 | 10/2017 | Nishimura |
| 9,809,630 B2 | 11/2017 | Ju |
| 9,809,796 B2 | 11/2017 | Gillberger |
| 9,862,753 B2 | 1/2018 | Yayon |
| 9,879,290 B2 | 1/2018 | Kurek |
| 9,883,689 B2 | 2/2018 | Perumalla |
| 9,901,631 B2 | 2/2018 | Degrace |
| 9,908,664 B2 | 3/2018 | Galliher |
| 9,925,241 B2 | 3/2018 | Suh |
| 9,926,355 B2 | 3/2018 | Mohammadi |
| 9,926,356 B2 | 3/2018 | Mohammadi |
| 9,932,553 B2 | 4/2018 | Brau |
| 9,943,545 B2 | 4/2018 | Rezner |
| 9,957,484 B2 | 5/2018 | Rana |
| 9,957,534 B2 | 5/2018 | Kurek |
| 9,969,965 B2 | 5/2018 | Tuohey |
| 9,969,966 B2 | 5/2018 | Asgari |
| 9,969,992 B2 | 5/2018 | Weiner |
| 9,975,936 B2 | 5/2018 | Cujec |
| 9,988,600 B2 | 6/2018 | Rayner-Brandes |
| 10,000,770 B2 | 6/2018 | Famili |
| 10,011,642 B2 | 7/2018 | Belouski |
| 10,011,822 B2 | 7/2018 | Wu |
| 10,022,415 B2 | 7/2018 | Yoo |
| 10,030,225 B2 | 7/2018 | Von Hagen |
| 10,045,544 B2 | 8/2018 | Spierts |
| 10,059,915 B2 | 8/2018 | Lee |
| 10,066,000 B2 | 9/2018 | Vasu |

(56)                References Cited

U.S. PATENT DOCUMENTS

| | | | |
|---|---|---|---|
| 10,066,205 | B2 | 9/2018 | Amit |
| 10,076,554 | B2 | 9/2018 | Boettcher |
| 10,081,787 | B2 | 9/2018 | Zeikus |
| 10,092,888 | B2 | 10/2018 | Barksdale |
| 10,093,904 | B2 | 10/2018 | Jaenisch |
| 10,098,368 | B2 | 10/2018 | Nakase |
| 10,104,903 | B2 | 10/2018 | Sunvold |
| 10,125,166 | B2 | 11/2018 | Rothbauer |
| 10,138,284 | B2 | 11/2018 | Weiss |
| 10,138,461 | B2 | 11/2018 | Grillberger |
| 10,144,938 | B2 | 12/2018 | Noguera |
| 10,179,898 | B2 | 1/2019 | Khan |
| 10,179,920 | B2 | 1/2019 | Jansson |
| 10,189,883 | B2 | 1/2019 | Morin |
| 10,196,617 | B2 | 2/2019 | Solbak |
| 10,222,387 | B2 | 3/2019 | Mcgrane |
| 10,226,548 | B2 | 3/2019 | Ahlfors |
| 10,227,559 | B2 | 3/2019 | Shimoni |
| 10,233,225 | B2 | 3/2019 | Dimarchi |
| 10,240,121 | B2 | 3/2019 | Gevaert |
| 10,266,843 | B2 | 4/2019 | Derosa |
| 10,273,265 | B2 | 4/2019 | Rothbauer |
| 10,280,397 | B2 | 5/2019 | Oatley |
| 10,294,289 | B2 | 5/2019 | Gouze |
| 10,327,463 | B2 | 6/2019 | Sheehan |
| 10,329,594 | B1 | 6/2019 | Forman |
| 10,336,799 | B2 | 7/2019 | Nolle |
| 10,336,983 | B2 | 7/2019 | Popp |
| 10,350,554 | B2 | 7/2019 | Goodwin |
| 10,364,278 | B2 | 7/2019 | Mohammadi |
| 10,377,805 | B2 | 8/2019 | Cujec |
| 10,377,806 | B2 | 8/2019 | Morin |
| 10,385,113 | B2 | 8/2019 | Thallapuranam |
| 10,392,429 | B2 | 8/2019 | Weiss |
| 10,400,210 | B2 | 9/2019 | Caracci |
| 10,428,340 | B2 | 10/2019 | Weiner |
| 10,428,349 | B2 | 10/2019 | Derosa |
| 10,429,378 | B2 | 10/2019 | Eilertsen |
| 10,472,404 | B2 | 11/2019 | Qin |
| 10,472,605 | B2 | 11/2019 | Barry |
| 10,473,673 | B2 | 11/2019 | Mcgrane |
| 10,519,413 | B2 | 12/2019 | Brau |
| 10,544,395 | B2 | 1/2020 | Hiller |
| 10,548,902 | B1 | 2/2020 | Majeed |
| 10,563,169 | B2 | 2/2020 | Von Hagen |
| 10,570,367 | B2 | 2/2020 | Bruninghaus |
| 10,577,613 | B1 | 3/2020 | Goel |
| 10,590,382 | B2 | 3/2020 | Amit |
| 10,619,131 | B2 | 4/2020 | Von Hagen |
| 10,633,424 | B2 | 4/2020 | Mohammadi |
| 10,655,099 | B2 | 5/2020 | Grillberger |
| 10,669,522 | B2 | 6/2020 | Fike |
| 10,669,524 | B2 | 6/2020 | Forgacs |
| 10,675,428 | B2 | 6/2020 | Guney |
| 10,689,652 | B2 | 6/2020 | Stampfer |
| 10,695,404 | B2 | 6/2020 | Evans |
| 10,696,731 | B2 | 6/2020 | Grillberger |
| 10,696,941 | B2 | 6/2020 | Dalla-Betta |
| 10,703,788 | B2 | 7/2020 | Mohammadi |
| 10,745,458 | B2 | 8/2020 | Weiss |
| 10,768,184 | B2 | 9/2020 | Mcgrane |
| 10,787,652 | B2 | 9/2020 | Lotvin |
| 10,793,827 | B2 | 10/2020 | Barrett |
| 10,801,003 | B2 | 10/2020 | Jaques |
| 10,842,809 | B2 | 11/2020 | Jackson |
| 10,843,141 | B2 | 11/2020 | Goodwin |
| 10,870,851 | B2 | 12/2020 | Stampfer |
| 10,883,076 | B2 | 1/2021 | Khan |
| 10,920,196 | B2 | 2/2021 | Genovese |
| 10,927,346 | B2 | 2/2021 | Valamehr |
| 10,954,276 | B2 | 3/2021 | Ju |
| 10,961,291 | B2 | 3/2021 | Cujec |
| 10,961,556 | B2 | 3/2021 | Ley |
| 10,973,242 | B2 | 4/2021 | Shigeta |
| 10,973,244 | B2 | 4/2021 | Jackson |
| 10,982,198 | B2 | 4/2021 | Lotvin |
| 10,995,129 | B2 | 5/2021 | Weiss |
| 11,001,810 | B1 | 5/2021 | Lian |
| 11,008,138 | B2 | 5/2021 | Galliher |
| 11,015,171 | B2 | 5/2021 | Yamashita |
| 11,021,528 | B2 | 6/2021 | Gouze |
| 11,028,361 | B2 | 6/2021 | Fike |
| 11,046,931 | B2 | 6/2021 | Caracci |
| 11,072,640 | B2 | 7/2021 | Belouski |
| 11,077,165 | B2 | 8/2021 | Zicker |
| 11,098,081 | B2 | 8/2021 | Rothbauer |
| 11,102,993 | B2 | 8/2021 | Stewart |
| 11,104,875 | B2 | 8/2021 | Hiller |
| 11,110,488 | B1 | 9/2021 | Frota |
| 11,111,471 | B2 | 9/2021 | Galliher |
| 11,124,760 | B2 | 9/2021 | Yang |
| 11,124,804 | B2 | 9/2021 | Derosa |
| 11,129,874 | B2 | 9/2021 | Boettcher |
| 11,135,244 | B2 | 10/2021 | Rezner |
| 11,142,560 | B2 | 10/2021 | Weiss |
| 11,147,300 | B2 | 10/2021 | Leung |
| 11,154,077 | B2 | 10/2021 | Corrigan |
| 11,162,062 | B2 | 11/2021 | Brau |
| 11,174,459 | B2 | 11/2021 | Forgacs |
| 11,203,738 | B2 | 12/2021 | Dyson |
| 11,207,257 | B2 | 12/2021 | Shin |
| 11,208,451 | B2 | 12/2021 | Qin |
| 11,208,633 | B2 | 12/2021 | Lotvin |
| 11,229,681 | B2 | 1/2022 | Takada |
| 11,230,725 | B2 | 1/2022 | Florin |
| 11,248,031 | B2 | 2/2022 | Morin |
| 11,248,034 | B2 | 2/2022 | Menting |
| 11,254,723 | B2 | 2/2022 | Fang |
| 11,259,546 | B2 | 3/2022 | Shigeta |
| 11,274,321 | B2 | 3/2022 | Reed |
| 11,284,633 | B2 | 3/2022 | Gross |
| 11,291,229 | B2 | 4/2022 | Ingoglia |
| 11,292,999 | B2 | 4/2022 | Paldus |
| 11,306,342 | B2 | 4/2022 | Chin |
| 11,312,539 | B2 | 4/2022 | Galliher |
| 11,324,233 | B2 | 5/2022 | Ray |
| 11,332,771 | B2 | 5/2022 | Oshodi |
| 11,344,050 | B2 | 5/2022 | Leung |
| 11,352,407 | B2 | 6/2022 | Lancaster |
| 11,357,244 | B2 | 6/2022 | Leung |
| 11,365,389 | B2 | 6/2022 | Barrett |
| 11,365,394 | B2 | 6/2022 | Valamehr |
| 11,371,002 | B2 | 6/2022 | Jaques |
| 11,391,725 | B2 | 7/2022 | Wang |
| 11,419,358 | B2 | 8/2022 | Akintoye |
| 11,427,802 | B2 | 8/2022 | Mironov |
| 11,432,574 | B2 | 9/2022 | Pattillo |
| 11,452,834 | B2 | 9/2022 | Guney |
| 11,466,246 | B2 | 10/2022 | Dyson |
| 11,466,290 | B2 | 10/2022 | Breunig |
| 11,470,871 | B2 | 10/2022 | Pattillo |
| 11,478,006 | B2 | 10/2022 | Pattillo |
| 11,479,591 | B2 | 10/2022 | Eveleth |
| 11,479,792 | B2 | 10/2022 | Genovese |
| 11,484,879 | B2 | 11/2022 | Hanyu |
| 11,498,949 | B2 | 11/2022 | Vasu |
| 11,499,135 | B2 | 11/2022 | Mironov |
| 11,504,651 | B2 | 11/2022 | Varanasi |
| 11,505,784 | B2 | 11/2022 | Clemens |
| 11,510,999 | B2 | 11/2022 | Lee |
| 11,512,273 | B2 | 11/2022 | Breemhaar |
| 11,555,058 | B2 | 1/2023 | Lancaster |
| 11,555,170 | B2 | 1/2023 | Flynn |
| 11,559,072 | B2 | 1/2023 | Leung |
| 11,559,073 | B2 | 1/2023 | Leung |
| 11,576,411 | B2 | 2/2023 | Leung |
| 11,589,598 | B2 | 2/2023 | Savir |
| 11,591,572 | B2 | 2/2023 | Clevers |
| 11,597,199 | B2 | 3/2023 | Parfenov |
| 11,627,751 | B2 | 4/2023 | Leung |
| 11,629,322 | B2 | 4/2023 | Prabhudharwadkar |
| 11,642,484 | B2 | 5/2023 | Guney |
| 11,649,449 | B2 | 5/2023 | Lawrence |
| 11,650,159 | B2 | 5/2023 | Renata |

(56) References Cited

U.S. PATENT DOCUMENTS

| | | |
|---|---|---|
| 11,660,415 B2 | 5/2023 | Guney |
| 11,680,237 B2 | 6/2023 | Castillo |
| 11,680,295 B2 | 6/2023 | Khatib |
| 11,685,899 B2 | 6/2023 | Simmons |
| 11,692,167 B2 | 7/2023 | Corbin |
| 11,697,624 B2 | 7/2023 | Blaney |
| 11,697,678 B2 | 7/2023 | Gouze |
| 11,702,629 B2 | 7/2023 | Walsh |
| 11,708,587 B2 | 7/2023 | Genovese |
| 11,714,081 B2 | 8/2023 | Eilertsen |
| 11,718,824 B2 | 8/2023 | Caracci |
| 11,725,290 B2 | 8/2023 | Reed |
| 11,738,510 B2 | 8/2023 | Kozlovski |
| 11,739,136 B2 | 8/2023 | Pu |
| 11,746,135 B2 | 9/2023 | Dvorak |
| 11,752,509 B2 | 9/2023 | Liu |
| 11,752,510 B2 | 9/2023 | Liu |
| 11,758,931 B2 | 9/2023 | Kayser |
| 11,760,964 B2 | 9/2023 | Muller-Aufferman |
| 11,771,112 B2 | 10/2023 | March |
| 11,779,033 B2 | 10/2023 | Scionti |
| 11,819,846 B2 | 11/2023 | Hanyu |
| 11,820,794 B2 | 11/2023 | Flynn |
| 11,827,677 B2 | 11/2023 | Wang |
| 11,834,643 B2 | 12/2023 | Galliher |
| 11,840,558 B2 | 12/2023 | Belouski |
| 11,859,161 B2 | 1/2024 | Paldus |
| 11,866,700 B2 | 1/2024 | Kang |
| 11,884,909 B2 | 1/2024 | Huang |
| 11,891,596 B2 | 2/2024 | Mueller-Auffermann |
| 11,898,127 B1 | 2/2024 | Leung |
| 11,912,967 B2 | 2/2024 | Tandikul |
| 11,912,972 B2 | 2/2024 | Huang |
| 11,944,664 B2 | 4/2024 | Boettcher |
| 11,952,597 B2 | 4/2024 | Lotvin |
| 11,970,724 B2 | 4/2024 | Oshodi |
| 11,976,302 B2 | 5/2024 | Genovese |
| 11,981,884 B2 | 5/2024 | Benton |
| 11,991,994 B2 | 5/2024 | Anderson-Baron |
| 11,992,029 B2 | 5/2024 | Peterson |
| 11,992,033 B2 | 5/2024 | Belt |
| 11,993,637 B2 | 5/2024 | Cujec |
| 12,031,152 B2 | 7/2024 | Johnson |
| 12,037,613 B2 | 7/2024 | Zhai |
| 12,041,949 B2 | 7/2024 | Ghotra |
| 12,089,615 B2 | 9/2024 | Ghotra |
| 12,102,102 B2 | 10/2024 | Kreamer |
| 12,127,575 B2 | 10/2024 | Pattillo |
| 12,168,019 B1 | 12/2024 | Andrews |
| 12,281,293 B1 | 4/2025 | Huang |
| 12,359,228 B2 | 7/2025 | Behkish |
| 12,391,773 B2 | 8/2025 | Mccurdy |
| 2004/0091968 A1 | 5/2004 | Short |
| 2005/0009161 A1 | 1/2005 | Streeter |
| 2005/0020814 A1 | 1/2005 | Rudolph |
| 2005/0037955 A1 | 2/2005 | Hooper |
| 2006/0094104 A1 | 5/2006 | Grillberger |
| 2006/0223155 A1 | 10/2006 | Streeter |
| 2007/0212332 A1 | 9/2007 | Baylink |
| 2007/0212770 A1 | 9/2007 | Grillberger |
| 2007/0212778 A1 | 9/2007 | Bramke |
| 2008/0009040 A1 | 1/2008 | Grillberger |
| 2008/0064080 A1 | 3/2008 | Grillberger |
| 2008/0064105 A1 | 3/2008 | Grillberger |
| 2008/0076158 A1 | 3/2008 | Dassler |
| 2008/0261299 A1 | 10/2008 | Zeikus |
| 2008/0313747 A1 | 12/2008 | Kern |
| 2009/0029465 A1 | 1/2009 | Thomson |
| 2009/0042253 A1 | 2/2009 | Hiller |
| 2009/0275128 A1 | 11/2009 | Thomson |
| 2009/0280217 A1 | 11/2009 | Katase |
| 2009/0304646 A1 | 12/2009 | Sakurada |
| 2010/0105100 A1 | 4/2010 | Sakurada |
| 2010/0120104 A1 | 5/2010 | Reed |
| 2010/0173409 A1 | 7/2010 | Gardner |
| 2010/0173839 A1 | 7/2010 | Glass |
| 2010/0178680 A1 | 7/2010 | Goodwin |
| 2010/0185047 A1 | 7/2010 | Khatib |
| 2010/0240090 A1 | 9/2010 | Sakurada |
| 2010/0267135 A1 | 10/2010 | Sakurada |
| 2010/0286042 A1 | 11/2010 | Imamura |
| 2011/0027417 A1 | 2/2011 | Corrigan |
| 2011/0039332 A1 | 2/2011 | Sakurada |
| 2011/0081680 A1 | 4/2011 | Grillberger |
| 2011/0081722 A1 | 4/2011 | Grillberger |
| 2011/0104754 A1 | 5/2011 | Bramke |
| 2011/0117603 A1 | 5/2011 | Piparia |
| 2011/0151512 A1 | 6/2011 | Grillberger |
| 2011/0262965 A1 | 10/2011 | Barrett |
| 2011/0306750 A1 | 12/2011 | Hoegenhaug |
| 2011/0312087 A1 | 12/2011 | Khan |
| 2012/0021094 A1 | 1/2012 | Sunvold |
| 2012/0052069 A1 | 3/2012 | Belouski |
| 2012/0135889 A1 | 5/2012 | Khatib |
| 2012/0156182 A1 | 6/2012 | Ahlfors |
| 2012/0190061 A1 | 7/2012 | Croughan |
| 2012/0214740 A1 | 8/2012 | Imamura |
| 2012/0308544 A1 | 12/2012 | Steinfeld |
| 2013/0078690 A1 | 3/2013 | Reed |
| 2013/0095062 A1 | 4/2013 | Chen |
| 2013/0149755 A1 | 6/2013 | Reed |
| 2013/0210707 A1 | 8/2013 | Chung |
| 2013/0236959 A1 | 9/2013 | Chen |
| 2013/0236962 A1 | 9/2013 | Thomson |
| 2013/0303573 A1 | 11/2013 | Boss |
| 2014/0094406 A1 | 4/2014 | Mohammadi |
| 2014/0107022 A1 | 4/2014 | Mohammadi |
| 2014/0134306 A1 | 5/2014 | Sakaji |
| 2014/0206083 A1 | 7/2014 | Sakurada |
| 2014/0273095 A1 | 9/2014 | Oshodi |
| 2014/0315280 A1 | 10/2014 | Ehwald |
| 2015/0017694 A1 | 1/2015 | Kurek |
| 2015/0031601 A1 | 1/2015 | Hoegenhaug |
| 2015/0076060 A1 | 3/2015 | Lee |
| 2015/0079238 A1 | 3/2015 | Marga |
| 2015/0099295 A1 | 4/2015 | Chen |
| 2015/0111821 A1 | 4/2015 | Suh |
| 2015/0132840 A1 | 5/2015 | Arnold |
| 2015/0140591 A1 | 5/2015 | Florin |
| 2015/0140640 A1 | 5/2015 | Reed |
| 2015/0183847 A1 | 7/2015 | Qin |
| 2015/0240219 A1 | 8/2015 | Baylink |
| 2015/0299280 A1 | 10/2015 | Nakayama |
| 2015/0315539 A1 | 11/2015 | Villanueva |
| 2016/0158317 A1 | 6/2016 | Hoegenhaug |
| 2016/0227830 A1 | 8/2016 | Genovese |
| 2016/0227831 A1 | 8/2016 | Marga |
| 2016/0244710 A1 | 8/2016 | Wood |
| 2016/0251625 A1 | 9/2016 | Genovese |
| 2016/0289633 A1 | 10/2016 | Yang |
| 2016/0312168 A1 | 10/2016 | Pizzi |
| 2017/0037421 A1 | 2/2017 | Blessing |
| 2017/0066808 A9 | 3/2017 | Glass |
| 2017/0095533 A1 | 4/2017 | Bogin |
| 2017/0143005 A1 | 5/2017 | Miyamoto |
| 2017/0172178 A1 | 6/2017 | Corrigan |
| 2017/0198258 A1 | 7/2017 | Jin |
| 2017/0218407 A1 | 8/2017 | Reed |
| 2017/0233447 A1 | 8/2017 | Qin |
| 2017/0327787 A1 | 11/2017 | Fukuda |
| 2017/0342371 A1 | 11/2017 | Barrett |
| 2018/0037867 A1 | 2/2018 | Simmons |
| 2018/0110240 A1 | 4/2018 | Mao |
| 2018/0127475 A1 | 5/2018 | Yayon |
| 2018/0148494 A1 | 5/2018 | Gouze |
| 2018/0179559 A1 | 6/2018 | Reed |
| 2018/0193418 A1 | 7/2018 | Suh |
| 2018/0237736 A1 | 8/2018 | Tuohey |
| 2018/0282431 A1 | 10/2018 | Scheer |
| 2018/0298409 A1 | 10/2018 | Reed |
| 2018/0346941 A1 | 12/2018 | Kurek |
| 2019/0008186 A1 | 1/2019 | Jackson |
| 2019/0014796 A1 | 1/2019 | Jackson |
| 2019/0024079 A1 | 1/2019 | Genovese |

(56)        References Cited

U.S. PATENT DOCUMENTS

| | | |
|---|---|---|
| 2019/0040427 A1 | 2/2019 | Kurek |
| 2019/0055513 A1 | 2/2019 | Ng |
| 2019/0069575 A1 | 3/2019 | Shigeta |
| 2019/0112572 A1 | 4/2019 | Figueroa |
| 2019/0136173 A1 | 5/2019 | Levinson |
| 2019/0144891 A1 | 5/2019 | Jansson |
| 2019/0161733 A1 | 5/2019 | Pijnappel |
| 2019/0169566 A1 | 6/2019 | Gevaert |
| 2019/0185584 A1 | 6/2019 | Scheer |
| 2019/0192630 A1 | 6/2019 | Suh |
| 2019/0241874 A1 | 8/2019 | Jaenisch |
| 2019/0292515 A1 | 9/2019 | Phelps |
| 2019/0300393 A1 | 10/2019 | Fleckner |
| 2019/0313666 A1 | 10/2019 | Lignet |
| 2019/0338232 A1 | 11/2019 | Breemhaar |
| 2019/0352676 A1 | 11/2019 | Senaratne |
| 2019/0382808 A1 | 12/2019 | Reed |
| 2019/0390161 A1 | 12/2019 | Knaup |
| 2020/0002397 A1 | 1/2020 | Qin |
| 2020/0005619 A1 | 1/2020 | Emmons |
| 2020/0010796 A1 | 1/2020 | Merz |
| 2020/0040303 A1 | 2/2020 | Simmons |
| 2020/0080048 A1 | 3/2020 | Popp |
| 2020/0080050 A1 | 3/2020 | Nahmias |
| 2020/0115669 A1 | 4/2020 | Bremer, Jr. |
| 2020/0140810 A1 | 5/2020 | Ben-Arye |
| 2020/0140821 A1 | 5/2020 | Elfenbein |
| 2020/0165569 A1 | 5/2020 | Genovese |
| 2020/0172856 A1 | 6/2020 | Reed |
| 2020/0181656 A1 | 6/2020 | Kurek |
| 2020/0181664 A1 | 6/2020 | Behkish |
| 2020/0205441 A1 | 7/2020 | Cheison |
| 2020/0236971 A1 | 7/2020 | Audibert |
| 2020/0239852 A1 | 7/2020 | Hiller |
| 2020/0270320 A1 | 8/2020 | Dvorak |
| 2020/0308579 A1 | 10/2020 | Kang |
| 2020/0325441 A1 | 10/2020 | Hiller |
| 2020/0377850 A1 | 12/2020 | Bruninghaus |
| 2020/0385674 A1 | 12/2020 | Ross |
| 2020/0392448 A1 | 12/2020 | Goodwin |
| 2020/0392461 A1 | 12/2020 | Mullen |
| 2020/0399603 A1 | 12/2020 | Kishida |
| 2021/0002605 A1 | 1/2021 | Murakami |
| 2021/0009657 A1 | 1/2021 | Gouze |
| 2021/0017548 A1 | 1/2021 | Behkish |
| 2021/0024959 A1 | 1/2021 | Valamehr |
| 2021/0037870 A1 | 2/2021 | Krieger |
| 2021/0068425 A1 | 3/2021 | Ross |
| 2021/0069654 A1 | 3/2021 | Goodwin |
| 2021/0076706 A1 | 3/2021 | Herrmann |
| 2021/0079342 A1 | 3/2021 | Amit |
| 2021/0084940 A1 | 3/2021 | Schlebusch |
| 2021/0087521 A1 | 3/2021 | Ikeda |
| 2021/0087525 A1 | 3/2021 | Burridge |
| 2021/0087537 A1 | 3/2021 | Valamehr |
| 2021/0092978 A1 | 4/2021 | Xu |
| 2021/0102163 A1 | 4/2021 | Lee |
| 2021/0123013 A1 | 4/2021 | Feyeux |
| 2021/0130760 A1 | 5/2021 | Castillo |
| 2021/0138219 A1 | 5/2021 | Stankowski |
| 2021/0139843 A1 | 5/2021 | Nahmias |
| 2021/0139858 A1 | 5/2021 | Lian |
| 2021/0163895 A1 | 6/2021 | Valamehr |
| 2021/0169802 A1 | 6/2021 | Yun |
| 2021/0171662 A1 | 6/2021 | Scheer |
| 2021/0171912 A1 | 6/2021 | Genovese |
| 2021/0189317 A1 | 6/2021 | Henry |
| 2021/0207080 A1 | 7/2021 | Beauchesne |
| 2021/0222109 A1 | 7/2021 | Yin |
| 2021/0222128 A1 | 7/2021 | Chen |
| 2021/0235733 A1 | 8/2021 | Kayser |
| 2021/0246480 A1 | 8/2021 | Chin |
| 2021/0269767 A1 | 9/2021 | Fike |
| 2021/0269797 A1 | 9/2021 | Beigelman |
| 2021/0284971 A1 | 9/2021 | Matsumoto |
| 2021/0307363 A1 | 10/2021 | Wernimont |
| 2021/0309956 A1 | 10/2021 | Pizzi |
| 2021/0317395 A1 | 10/2021 | Hiller |
| 2021/0332326 A1 | 10/2021 | Vodnala |
| 2021/0340570 A1 | 11/2021 | Genovese |
| 2021/0345654 A1 | 11/2021 | Krieger |
| 2021/0348108 A1 | 11/2021 | Choi |
| 2021/0348129 A1 | 11/2021 | Rebello |
| 2021/0371788 A1 | 12/2021 | Huang |
| 2021/0380923 A1 | 12/2021 | Coffman |
| 2021/0392908 A1 | 12/2021 | Reed |
| 2021/0392920 A1 | 12/2021 | Dyson |
| 2021/0393700 A1 | 12/2021 | O'Heeron |
| 2021/0395677 A1 | 12/2021 | Reed |
| 2021/0395690 A1 | 12/2021 | Nahmias |
| 2022/0000154 A1 | 1/2022 | Leung |
| 2022/0000826 A1 | 1/2022 | Jewell |
| 2022/0002652 A1 | 1/2022 | Patrick |
| 2022/0007695 A1 | 1/2022 | Kayser |
| 2022/0007696 A1 | 1/2022 | Lavon |
| 2022/0017859 A1 | 1/2022 | Guehenneux |
| 2022/0023807 A1 | 1/2022 | Damren |
| 2022/0025310 A1 | 1/2022 | Chin |
| 2022/0033753 A1 | 2/2022 | Brau |
| 2022/0041672 A1 | 2/2022 | Misaghi |
| 2022/0041979 A1 | 2/2022 | Forgacs |
| 2022/0053796 A1 | 2/2022 | Bayle |
| 2022/0056394 A1 | 2/2022 | Leung |
| 2022/0064217 A1 | 3/2022 | Wehkamp |
| 2022/0064690 A1 | 3/2022 | Florin |
| 2022/0071233 A1 | 3/2022 | Kaplan |
| 2022/0071247 A1 | 3/2022 | Kayser |
| 2022/0073856 A1 | 3/2022 | Pitkänen |
| 2022/0073868 A1 | 3/2022 | Cooper |
| 2022/0073870 A1 | 3/2022 | Johnson |
| 2022/0073944 A1 | 3/2022 | Derosa |
| 2022/0079194 A1 | 3/2022 | Li |
| 2022/0079200 A2 | 3/2022 | Krieger |
| 2022/0081475 A1 | 3/2022 | Li |
| 2022/0089661 A1 | 3/2022 | Li |
| 2022/0096598 A1 | 3/2022 | Duan |
| 2022/0098546 A1 | 3/2022 | Akcali |
| 2022/0110347 A1 | 4/2022 | Leung |
| 2022/0145337 A1 | 5/2022 | Reed |
| 2022/0154137 A1 | 5/2022 | Ng |
| 2022/0154228 A1 | 5/2022 | Reed |
| 2022/0162662 A1 | 5/2022 | Chin |
| 2022/0168220 A1 | 6/2022 | Levin |
| 2022/0169962 A1 | 6/2022 | Takeuchi |
| 2022/0169973 A1 | 6/2022 | Dehottay et al. |
| 2022/0177818 A1 | 6/2022 | Matuszczyk |
| 2022/0177823 A1 | 6/2022 | Vila |
| 2022/0183316 A1 | 6/2022 | Santo |
| 2022/0183317 A1 | 6/2022 | Krieger |
| 2022/0184142 A1 | 6/2022 | Valamehr |
| 2022/0185856 A1 | 6/2022 | Morin |
| 2022/0186167 A1 | 6/2022 | Vela |
| 2022/0195358 A1 | 6/2022 | Tandikul |
| 2022/0195359 A1 | 6/2022 | Lavon |
| 2022/0195368 A1 | 6/2022 | Genovese |
| 2022/0195392 A1 | 6/2022 | Rowat |
| 2022/0202759 A1 | 6/2022 | Jackson |
| 2022/0204909 A1 | 6/2022 | Alzate |
| 2022/0213427 A1 | 7/2022 | Melchiorri |
| 2022/0213438 A1 | 7/2022 | Lin |
| 2022/0220439 A1 | 7/2022 | Lavon |
| 2022/0228097 A1 | 7/2022 | White |
| 2022/0228121 A1 | 7/2022 | Stout |
| 2022/0228187 A1 | 7/2022 | Oshodi |
| 2022/0234012 A1 | 7/2022 | Castan |
| 2022/0243192 A1 | 8/2022 | Forman |
| 2022/0243193 A1 | 8/2022 | Forman |
| 2022/0251487 A1 | 8/2022 | Kubota |
| 2022/0251550 A1 | 8/2022 | Genovese |
| 2022/0275325 A1 | 9/2022 | Barrett |
| 2022/0282285 A1 | 9/2022 | Webber |
| 2022/0287331 A1 | 9/2022 | Schlebusch |
| 2022/0290090 A1 | 9/2022 | Ball |
| 2022/0298472 A1 | 9/2022 | Kober |

(56) References Cited

U.S. PATENT DOCUMENTS

| | | |
|---|---|---|
| 2022/0298480 A1 | 9/2022 | Chin |
| 2022/0306987 A1 | 9/2022 | Duthoit |
| 2022/0308042 A1 | 9/2022 | Wang |
| 2022/0315880 A1 | 10/2022 | Lang |
| 2022/0315953 A1 | 10/2022 | Langereis |
| 2022/0322703 A1 | 10/2022 | Van Eyk |
| 2022/0325212 A1 | 10/2022 | Toledano |
| 2022/0325220 A1 | 10/2022 | Vainikka |
| 2022/0325258 A1 | 10/2022 | Kogut |
| 2022/0330599 A1 | 10/2022 | Zahn |
| 2022/0333066 A1 | 10/2022 | Amit |
| 2022/0333148 A1 | 10/2022 | Chin |
| 2022/0340636 A1 | 10/2022 | Menting |
| 2022/0340864 A1 | 10/2022 | Shimizu |
| 2022/0369665 A1 | 11/2022 | Valenzuela |
| 2022/0372435 A1 | 11/2022 | Phelps |
| 2022/0372436 A1 | 11/2022 | Oshodi |
| 2022/0380712 A1 | 12/2022 | Sieck |
| 2022/0388725 A1 | 12/2022 | Galliher |
| 2022/0394997 A1 | 12/2022 | Legarth |
| 2022/0395001 A1 | 12/2022 | Jackson |
| 2022/0400716 A1 | 12/2022 | Rease |
| 2022/0408731 A1 | 12/2022 | Shah |
| 2022/0411734 A1 | 12/2022 | Pietras |
| 2022/0411742 A1 | 12/2022 | Namatame |
| 2022/0411824 A1 | 12/2022 | Genovese |
| 2023/0002718 A1 | 1/2023 | Haupt |
| 2023/0002739 A1 | 1/2023 | Newton |
| 2023/0012452 A1 | 1/2023 | Pereira-Taveres |
| 2023/0016607 A1 | 1/2023 | Lu |
| 2023/0017014 A1 | 1/2023 | Drugmand |
| 2023/0030915 A1 | 2/2023 | Jewell |
| 2023/0045226 A1 | 2/2023 | Jaques |
| 2023/0046426 A1 | 2/2023 | Hariharan |
| 2023/0049887 A1 | 2/2023 | Audibert |
| 2023/0050194 A1 | 2/2023 | Vogel |
| 2023/0054944 A1 | 2/2023 | Ben-Shitrit |
| 2023/0060907 A1 | 3/2023 | Gharibian |
| 2023/0067342 A1 | 3/2023 | Jackson |
| 2023/0067465 A1 | 3/2023 | Yon |
| 2023/0070582 A1 | 3/2023 | Nahmias |
| 2023/0071409 A1 | 3/2023 | Trassy |
| 2023/0073515 A1 | 3/2023 | Rezania |
| 2023/0073614 A1 | 3/2023 | Nahmias |
| 2023/0075095 A1 | 3/2023 | King |
| 2023/0077429 A1 | 3/2023 | Caplan |
| 2023/0081499 A1 | 3/2023 | Popp |
| 2023/0083026 A1 | 3/2023 | Moutsatsou |
| 2023/0091040 A1 | 3/2023 | Leung |
| 2023/0091231 A1 | 3/2023 | Nahmias |
| 2023/0093399 A1 | 3/2023 | West |
| 2023/0100306 A1 | 3/2023 | Engelmayr, Jr. |
| 2023/0101863 A1 | 3/2023 | Robertson |
| 2023/0105342 A1 | 4/2023 | Anderson-Baron |
| 2023/0108652 A1 | 4/2023 | Konrad |
| 2023/0108890 A1 | 4/2023 | Kawashima |
| 2023/0122678 A1 | 4/2023 | Dyson |
| 2023/0130038 A1 | 4/2023 | Vasu |
| 2023/0130851 A1 | 4/2023 | Eveleth |
| 2023/0132594 A1 | 5/2023 | Sathe |
| 2023/0132925 A1 | 5/2023 | Jane |
| 2023/0146879 A1 | 5/2023 | Röntgen |
| 2023/0149834 A1 | 5/2023 | Varanasi |
| 2023/0151330 A1 | 5/2023 | Faram |
| 2023/0151386 A1 | 5/2023 | Henry |
| 2023/0157316 A1 | 5/2023 | Rease |
| 2023/0159874 A1 | 5/2023 | Johannessen |
| 2023/0159879 A1 | 5/2023 | Henry |
| 2023/0159954 A1 | 5/2023 | Henry |
| 2023/0167394 A1 | 6/2023 | Gaertner |
| 2023/0172231 A1 | 6/2023 | Zaune-Figlar |
| 2023/0183762 A1 | 6/2023 | Reed |
| 2023/0203420 A1 | 6/2023 | Leung |
| 2023/0203446 A1 | 6/2023 | Konrad |
| 2023/0203449 A1 | 6/2023 | Clemens |
| 2023/0210131 A1 | 7/2023 | Savir |
| 2023/0210132 A1 | 7/2023 | Savir |
| 2023/0210133 A1 | 7/2023 | Ido |
| 2023/0210134 A1 | 7/2023 | Savir |
| 2023/0210135 A1 | 7/2023 | Ido |
| 2023/0212498 A1 | 7/2023 | Bode |
| 2023/0220027 A1 | 7/2023 | Orvar |
| 2023/0220332 A1 | 7/2023 | Amit |
| 2023/0220347 A1 | 7/2023 | Hwang |
| 2023/0225361 A1 | 7/2023 | Yaakov |
| 2023/0225391 A1 | 7/2023 | Mandelik |
| 2023/0227760 A1 | 7/2023 | Vila |
| 2023/0227764 A1 | 7/2023 | Prabhudharwadkar |
| 2023/0240324 A1 | 8/2023 | Dikovsky |
| 2023/0240325 A1 | 8/2023 | Leune |
| 2023/0240334 A1 | 8/2023 | Marchal |
| 2023/0248020 A1 | 8/2023 | Chuang |
| 2023/0250148 A1 | 8/2023 | Lancaster |
| 2023/0255253 A1 | 8/2023 | Levin |
| 2023/0257711 A1 | 8/2023 | Roberts |
| 2023/0270965 A1 | 8/2023 | Guney |
| 2023/0272318 A1 | 8/2023 | Liu |
| 2023/0272324 A1 | 8/2023 | Castillo |
| 2023/0272346 A1 | 8/2023 | Genovese |
| 2023/0272347 A1 | 8/2023 | Clevers |
| 2023/0279320 A1 | 9/2023 | Flynn |
| 2023/0284662 A1 | 9/2023 | Kaplan |
| 2023/0287317 A1 | 9/2023 | Kaplan |
| 2023/0303646 A1 | 9/2023 | Boss |
| 2023/0303956 A1 | 9/2023 | Weissenbach |
| 2023/0313109 A1 | 10/2023 | Sieck |
| 2023/0320288 A1 | 10/2023 | Scully |
| 2023/0322904 A1 | 10/2023 | Sanctorum |
| 2023/0323287 A1 | 10/2023 | Daris |
| 2023/0332101 A1 | 10/2023 | Walsh |
| 2023/0340390 A1 | 10/2023 | Zheng |
| 2023/0348545 A1 | 11/2023 | Gasser |
| 2023/0354851 A1 | 11/2023 | Montelongo |
| 2023/0357445 A1 | 11/2023 | Scheer |
| 2023/0365639 A1 | 11/2023 | Wehkamp |
| 2023/0365919 A1 | 11/2023 | Barrett |
| 2023/0365920 A1 | 11/2023 | Hiller |
| 2023/0371552 A1 | 11/2023 | Jackson |
| 2023/0374432 A1 | 11/2023 | Goh |
| 2023/0383223 A1 | 11/2023 | Wang |
| 2023/0392120 A1 | 12/2023 | Dhadwar |
| 2023/0397633 A1 | 12/2023 | Davila |
| 2023/0399620 A1 | 12/2023 | Dhadwar |
| 2023/0404951 A1 | 12/2023 | Ephraim |
| 2023/0407224 A1 | 12/2023 | Lavon |
| 2023/0413856 A1 | 12/2023 | Padilla |
| 2023/0416674 A1 | 12/2023 | Figueroa |
| 2023/0416747 A1 | 12/2023 | Zheng |
| 2024/0000128 A1 | 1/2024 | Han |
| 2024/0002784 A1 | 1/2024 | Inada |
| 2024/0002803 A1 | 1/2024 | Savir |
| 2024/0008507 A1 | 1/2024 | Felke |
| 2024/0010983 A1 | 1/2024 | Weissenbach |
| 2024/0010984 A1 | 1/2024 | Cruz |
| 2024/0016185 A1 | 1/2024 | March |
| 2024/0034979 A1 | 2/2024 | Chen |
| 2024/0034987 A1 | 2/2024 | Kaplan |
| 2024/0041064 A1 | 2/2024 | Zotter |
| 2024/0041067 A1 | 2/2024 | Scionti |
| 2024/0043493 A1 | 2/2024 | Weiss |
| 2024/0043787 A1 | 2/2024 | Robertson |
| 2024/0052291 A1 | 2/2024 | Connon |
| 2024/0060191 A1 | 2/2024 | Reed |
| 2024/0066149 A1 | 2/2024 | Kinoshita |
| 2024/0074478 A1 | 3/2024 | Block |
| 2024/0076594 A1 | 3/2024 | Paldus |
| 2024/0084258 A1 | 3/2024 | Yamamoto |
| 2024/0090531 A1 | 3/2024 | Macqueen |
| 2024/0093141 A1 | 3/2024 | Holmström |
| 2024/0093152 A1 | 3/2024 | Kaplan |
| 2024/0093153 A1 | 3/2024 | Chin |
| 2024/0101968 A1 | 3/2024 | Keophiphath |
| 2024/0108031 A1 | 4/2024 | Sagalowicz |
| 2024/0117287 A1 | 4/2024 | Mueller-Auffermann |

(56) References Cited

U.S. PATENT DOCUMENTS

| | | | |
|---|---|---|---|
| 2024/0117401 A1 | 4/2024 | Balcarcel | |
| 2024/0122222 A1 | 4/2024 | Ercili-Cura | |
| 2024/0141268 A1 | 5/2024 | Tandikul | |
| 2024/0148012 A1 | 5/2024 | Hosseini | |
| 2024/0148022 A1 | 5/2024 | Davila | |
| 2024/0148023 A1 | 5/2024 | Li | |
| 2024/0148024 A1 | 5/2024 | Ong | |
| 2024/0148025 A1 | 5/2024 | Nikinmaa | |
| 2024/0148034 A1 | 5/2024 | Hosseini | |
| 2024/0150723 A1 | 5/2024 | Forte | |
| 2024/0150724 A1 | 5/2024 | Hosseini | |
| 2024/0156127 A1 | 5/2024 | Häkämies | |
| 2024/0156138 A1 | 5/2024 | Häkämies | |
| 2024/0158449 A1 | 5/2024 | Flynn | |
| 2024/0164404 A1 | 5/2024 | Frelka | |
| 2024/0164406 A1 | 5/2024 | Häkämies | |
| 2024/0165557 A1 | 5/2024 | Tervasmäki | |
| 2024/0174957 A1 | 5/2024 | Dezfuli | |
| 2024/0174963 A1 | 5/2024 | Huang | |
| 2024/0182859 A1 | 6/2024 | Han | |
| 2024/0191198 A1 | 6/2024 | Benson | |
| 2024/0191200 A1 | 6/2024 | Simmons | |
| 2024/0191206 A1 | 6/2024 | Amit | |
| 2024/0196944 A1 | 6/2024 | Leung | |
| 2024/0200033 A1 | 6/2024 | Banks | |
| 2024/0200110 A1 | 6/2024 | Nissinen | |
| 2024/0209033 A1 | 6/2024 | Chaung | |
| 2024/0218311 A1 | 7/2024 | Nahmias | |
| 2024/0218315 A1 | 7/2024 | Vainikka | |
| 2024/0218319 A1 | 7/2024 | Ercili-Cura | |
| 2024/0225047 A9 | 7/2024 | Stadler | |
| 2024/0225060 A1 | 7/2024 | Walker | |
| 2024/0228940 A1 | 7/2024 | Goral | |
| 2024/0229096 A1 | 7/2024 | Bae | |
| 2024/0240133 A1 | 7/2024 | Buchmann | |
| 2024/0254419 A1 | 8/2024 | Castillo | |
| 2024/0254435 A1 | 8/2024 | Jämsä | |
| 2024/0254470 A1 | 8/2024 | Forman | |
| 2024/0261371 A1 | 8/2024 | Xiao | |
| 2024/0268422 A1 | 8/2024 | Hosseini | |
| 2024/0277831 A1 | 8/2024 | King | |
| 2024/0287463 A1 | 8/2024 | Chen | |
| 2024/0287569 A1 | 8/2024 | Chen | |
| 2024/0298678 A1 | 9/2024 | Hosseini | |
| 2024/0301442 A1 | 9/2024 | Wang | |
| 2024/0315306 A1 | 9/2024 | Larumbe Beramendi | |
| 2024/0318133 A1 | 9/2024 | Johnson | |
| 2024/0327771 A1 | 10/2024 | Yoshioka | |
| 2024/0336895 A1 | 10/2024 | Pelling | |
| 2024/0352423 A1 | 10/2024 | Hosseini | |
| 2024/0397977 A1 | 12/2024 | Wernimont | |
| 2024/0399431 A1 | 12/2024 | Balaban | |
| 2024/0400960 A1 | 12/2024 | Thyden | |
| 2025/0000123 A1 | 1/2025 | Matthew | |
| 2025/0043228 A1 | 2/2025 | Mueller-Auffermann | |
| 2025/0043240 A1* | 2/2025 | Ovissipour | C12N 9/54 |
| 2025/0108072 A1 | 4/2025 | Silva | |
| 2025/0179122 A1 | 6/2025 | Andrews | |
| 2025/0215372 A1 | 7/2025 | Timmins | |
| 2025/0280854 A1 | 9/2025 | Badri | |
| 2025/0340821 A1 | 11/2025 | Boyce | |

FOREIGN PATENT DOCUMENTS

| | | | |
|---|---|---|---|
| CN | 101463319 A | 6/2009 | |
| CN | 101603026 B | 1/2011 | |
| CN | 102603886 B | 8/2013 | |
| CN | 103045636 B | 3/2014 | |
| CN | 103113461 B | 6/2014 | |
| CN | 102618440 B | 7/2014 | |
| CN | 103320461 B | 4/2015 | |
| CN | 103468673 B | 8/2015 | |
| CN | 103757025 B | 10/2015 | |
| CN | 103641903 B | 3/2016 | |
| CN | 104292939 B | 4/2016 | |
| CN | 103205453 B | 6/2016 | |
| CN | 103960457 B | 6/2016 | |
| CN | 205662385 U | 10/2016 | |
| CN | 104582828 B | 11/2016 | |
| CN | 106086041 A | 11/2016 | |
| CN | 104445634 B | 3/2017 | |
| CN | 104497119 B | 11/2017 | |
| CN | 104387465 B | 12/2017 | |
| CN | 106811473 B | 5/2018 | |
| CN | 105985956 B | 9/2018 | |
| CN | 105524158 B | 1/2019 | |
| CN | 105731654 B | 2/2019 | |
| CN | 105800886 B | 2/2019 | |
| CN | 105348380 B | 3/2019 | |
| CN | 105622763 B | 3/2019 | |
| CN | 106635972 B | 3/2019 | |
| CN | 109628533 A | 4/2019 | |
| CN | 105199969 B | 5/2019 | |
| CN | 106146088 B | 5/2019 | |
| CN | 104404012 B | 6/2019 | |
| CN | 110484487 A | 11/2019 | |
| CN | 110583892 A | 12/2019 | |
| CN | 105861594 B | 4/2020 | |
| CN | 107176762 B | 6/2020 | |
| CN | 107217069 B | 6/2020 | |
| CN | 110128519 B | 6/2020 | |
| CN | 107188944 B | 7/2020 | |
| CN | 107267537 B | 7/2020 | |
| CN | 108467426 B | 8/2020 | |
| CN | 110257227 B | 8/2020 | |
| CN | 111088282 B | 8/2020 | |
| CN | 110241023 B | 9/2020 | |
| CN | 106929547 B | 10/2020 | |
| CN | 109336982 B | 10/2020 | |
| CN | 111019881 B | 10/2020 | |
| CN | 111808820 A | 10/2020 | |
| CN | 106978390 B | 11/2020 | |
| CN | 109321519 B | 1/2021 | |
| CN | 106635953 B | 2/2021 | |
| CN | 107686516 B | 2/2021 | |
| CN | 108373510 B | 2/2021 | |
| CN | 212488409 U | 2/2021 | |
| CN | 112626013 A | 4/2021 | |
| CN | 112717120 A | 4/2021 | |
| CN | 111087449 B | 5/2021 | |
| CN | 110468143 B | 6/2021 | |
| CN | 112919718 A | 6/2021 | |
| CN | 112941034 A | 6/2021 | |
| CN | 107487841 B | 7/2021 | |
| CN | 108771028 B | 8/2021 | |
| CN | 109055085 B | 8/2021 | |
| CN | 111620745 B | 8/2021 | |
| CN | 112795531 B | 8/2021 | |
| CN | 109021088 B | 9/2021 | |
| CN | 109180794 B | 9/2021 | |
| CN | 111269926 B | 9/2021 | |
| CN | 113355354 A | 9/2021 | |
| CN | 109287864 B | 10/2021 | |
| CN | 109674023 B | 10/2021 | |
| CN | 109467595 B | 11/2021 | |
| CN | 108148875 B | 12/2021 | |
| CN | 111333700 B | 12/2021 | |
| CN | 111333716 B | 12/2021 | |
| CN | 111500608 B | 1/2022 | |
| CN | 110255699 B | 2/2022 | |
| CN | 110697959 B | 2/2022 | |
| CN | 114010525 A | 2/2022 | |
| CN | 108752455 B | 3/2022 | |
| CN | 109206475 B | 3/2022 | |
| CN | 111560059 B | 3/2022 | |
| CN | 111973805 B | 3/2022 | |
| CN | 109536507 B | 4/2022 | |
| CN | 111944823 B | 4/2022 | |
| CN | 114106103 B | 4/2022 | |
| CN | 114316017 A | 4/2022 | |
| CN | 114317303 A | 4/2022 | |
| CN | 111153982 B | 5/2022 | |
| CN | 109593630 B | 6/2022 | |
| CN | 110564772 B | 7/2022 | |

(56)　　　　References Cited

FOREIGN PATENT DOCUMENTS

| | | | |
|---|---|---|---|
| CN | 110804091 | B | 7/2022 |
| CN | 111662370 | B | 7/2022 |
| CN | 110438027 | B | 8/2022 |
| CN | 112225793 | B | 8/2022 |
| CN | 113527513 | B | 8/2022 |
| CN | 114891733 | A | 8/2022 |
| CN | 114958716 | A | 8/2022 |
| CN | 217265341 | U | 8/2022 |
| CN | 111500590 | B | 9/2022 |
| CN | 114990055 | A | 9/2022 |
| CN | 217377581 | U | 9/2022 |
| CN | 115247180 | A | 10/2022 |
| CN | 115247188 | A | 10/2022 |
| CN | 115247189 | A | 10/2022 |
| CN | 109504680 | B | 11/2022 |
| CN | 114540123 | B | 11/2022 |
| CN | 113025563 | B | 12/2022 |
| CN | 115462435 | A | 12/2022 |
| CN | 115595296 | A | 1/2023 |
| CN | 115651891 | A | 1/2023 |
| CN | 112961833 | B | 3/2023 |
| CN | 115820372 | A | 3/2023 |
| CN | 115820564 | A | 3/2023 |
| CN | 115820607 | A | 3/2023 |
| CN | 112501126 | B | 4/2023 |
| CN | 114804533 | B | 4/2023 |
| CN | 115975806 | A | 4/2023 |
| CN | 116004520 | A | 4/2023 |
| CN | 218860500 | U | 4/2023 |
| CN | 111892646 | B | 5/2023 |
| CN | 114835824 | B | 5/2023 |
| CN | 115536711 | B | 5/2023 |
| CN | 116041478 | A | 5/2023 |
| CN | 116042681 | A | 5/2023 |
| CN | 116103166 | A | 5/2023 |
| CN | 116121174 | A | 5/2023 |
| CN | 219079145 | U | 5/2023 |
| CN | 110592004 | B | 6/2023 |
| CN | 112522205 | B | 6/2023 |
| CN | 114712485 | B | 6/2023 |
| CN | 116200372 | A | 6/2023 |
| CN | 116200420 | A | 6/2023 |
| CN | 116217681 | A | 6/2023 |
| CN | 116239702 | A | 6/2023 |
| CN | 116254220 | A | 6/2023 |
| CN | 116327884 | A | 6/2023 |
| CN | 219186467 | U | 6/2023 |
| CN | 114317330 | B | 7/2023 |
| CN | 114767757 | B | 7/2023 |
| CN | 116376951 | A | 7/2023 |
| CN | 113754784 | B | 8/2023 |
| CN | 115044541 | B | 8/2023 |
| CN | 116333075 | B | 8/2023 |
| CN | 116555389 | A | 8/2023 |
| CN | 116621643 | A | 8/2023 |
| CN | 113862277 | B | 9/2023 |
| CN | 114751991 | B | 9/2023 |
| CN | 115485367 | B | 9/2023 |
| CN | 115975002 | B | 9/2023 |
| CN | 116458565 | B | 9/2023 |
| CN | 116693650 | A | 9/2023 |
| CN | 116731120 | A | 9/2023 |
| CN | 116731148 | A | 9/2023 |
| CN | 116801725 | A | 9/2023 |
| CN | 113717973 | B | 10/2023 |
| CN | 115404222 | B | 10/2023 |
| CN | 116590225 | B | 10/2023 |
| CN | 116926014 | A | 10/2023 |
| CN | 116970548 | A | 10/2023 |
| CN | 114805534 | B | 11/2023 |
| CN | 116333159 | B | 11/2023 |
| CN | 116732099 | B | 11/2023 |
| CN | 117004555 | A | 11/2023 |
| CN | 117070381 | A | 11/2023 |
| CN | 117126894 | A | 11/2023 |
| CN | 114525304 | B | 12/2023 |
| CN | 116987200 | B | 12/2023 |
| CN | 117210386 | A | 12/2023 |
| CN | 117243262 | A | 12/2023 |
| CN | 117247886 | A | 12/2023 |
| CN | 117247897 | A | 12/2023 |
| CN | 117281134 | A | 12/2023 |
| CN | 117304334 | A | 12/2023 |
| CN | 117363577 | A | 1/2024 |
| CN | 117430685 | A | 1/2024 |
| CN | 113908252 | B | 2/2024 |
| CN | 116143899 | B | 2/2024 |
| CN | 116875476 | B | 2/2024 |
| CN | 117486981 | A | 2/2024 |
| CN | 117511861 | A | 2/2024 |
| CN | 117535349 | A | 2/2024 |
| CN | 117551693 | A | 2/2024 |
| CN | 117551694 | A | 2/2024 |
| CN | 117551729 | A | 2/2024 |
| CN | 117568267 | A | 2/2024 |
| CN | 117586424 | A | 2/2024 |
| CN | 117599112 | A | 2/2024 |
| CN | 117603902 | A | 2/2024 |
| CN | 115386541 | B | 3/2024 |
| CN | 117384275 | B | 3/2024 |
| CN | 117486996 | B | 3/2024 |
| CN | 117643791 | A | 3/2024 |
| CN | 117717503 | A | 3/2024 |
| CN | 117737103 | A | 3/2024 |
| CN | 117778468 | A | 3/2024 |
| CN | 111471644 | B | 4/2024 |
| CN | 114316031 | B | 4/2024 |
| CN | 114790237 | B | 4/2024 |
| CN | 114958761 | B | 4/2024 |
| CN | 114990056 | B | 4/2024 |
| CN | 117447580 | B | 4/2024 |
| CN | 117837749 | A | 4/2024 |
| CN | 117866883 | A | 4/2024 |
| CN | 114686438 | B | 5/2024 |
| CN | 116003541 | B | 5/2024 |
| CN | 116262781 | B | 5/2024 |
| CN | 116262782 | B | 5/2024 |
| CN | 116986758 | B | 5/2024 |
| CN | 117959819 | A | 5/2024 |
| CN | 117964154 | A | 5/2024 |
| CN | 117965599 | A | 5/2024 |
| CN | 117987355 | A | 5/2024 |
| CN | 118048371 | A | 5/2024 |
| CN | 118086050 | A | 5/2024 |
| CN | 118086356 | A | 5/2024 |
| CN | 118108545 | A | 5/2024 |
| CN | 220907314 | U | 5/2024 |
| CN | 116218695 | B | 6/2024 |
| CN | 117586842 | B | 6/2024 |
| CN | 118146312 | A | 6/2024 |
| CN | 118207231 | A | 6/2024 |
| CN | 118291386 | A | 7/2024 |
| CN | 118344490 | A | 7/2024 |
| CN | 118373892 | A | 7/2024 |
| CN | 118374440 | A | 7/2024 |
| CN | 118388055 | A | 7/2024 |
| CN | 116924844 | B | 8/2024 |
| CN | 118439747 | A | 8/2024 |
| CN | 118440883 | A | 8/2024 |
| CN | 118440891 | A | 8/2024 |
| CN | 118460420 | A | 8/2024 |
| CN | 118497116 | A | 8/2024 |
| CN | 118546864 | A | 8/2024 |
| CN | 116058444 | B | 9/2024 |
| CN | 118598338 | A | 9/2024 |
| CN | 118702786 | A | 9/2024 |
| CN | 116003512 | B | 10/2024 |
| CN | 118059163 | B | 10/2024 |
| CN | 118389446 | B | 10/2024 |
| CN | 118633673 | B | 10/2024 |
| CN | 118724315 | A | 10/2024 |
| CN | 118726142 | A | 10/2024 |
| CN | 118813529 | A | 10/2024 |
| CN | 221788804 | U | 10/2024 |

(56)            References Cited

FOREIGN PATENT DOCUMENTS

| | | | |
|---|---|---|---|
| CN | 116555266 | B | 11/2024 |
| CN | 117886893 | B | 11/2024 |
| CN | 118872847 | A | 11/2024 |
| CN | 118878701 | A | 11/2024 |
| CN | 118909950 | A | 11/2024 |
| CN | 118956737 | A | 11/2024 |
| CN | 118956911 | A | 11/2024 |
| CN | 119014506 | A | 11/2024 |
| CN | 119020438 | A | 11/2024 |
| CN | 119039392 | A | 11/2024 |
| CN | 117624382 | B | 12/2024 |
| CN | 118324849 | B | 12/2024 |
| CN | 118581048 | B | 12/2024 |
| CN | 119113034 | A | 12/2024 |
| CN | 119120354 | A | 12/2024 |
| CN | 119144663 | A | 12/2024 |
| CN | 119193265 | A | 12/2024 |
| CN | 119193355 | A | 12/2024 |
| CN | 119193471 | A | 12/2024 |
| CN | 119193472 | A | 12/2024 |
| CN | 118546228 | B | 1/2025 |
| CN | 119235703 | A | 1/2025 |
| CN | 119242709 | A | 1/2025 |
| CN | 119265260 | A | 1/2025 |
| CN | 119318609 | A | 1/2025 |
| CN | 119320777 | A | 1/2025 |
| CN | 119350464 | A | 1/2025 |
| CN | 114874978 | B | 2/2025 |
| CN | 118995825 | B | 2/2025 |
| CN | 118995826 | B | 2/2025 |
| CN | 119214214 | B | 2/2025 |
| CN | 119432767 | A | 2/2025 |
| CN | 119464267 | A | 2/2025 |
| CN | 119523087 | A | 2/2025 |
| CN | 119529034 | A | 2/2025 |
| CN | 119530146 | A | 2/2025 |
| CN | 118755665 | B | 3/2025 |
| CN | 119563773 | A | 3/2025 |
| CN | 119662526 | A | 3/2025 |
| CN | 119685251 | A | 3/2025 |
| CN | 119700624 | A | 3/2025 |
| CN | 116925199 | B | 4/2025 |
| CN | 119490567 | B | 4/2025 |
| CN | 119745714 | A | 4/2025 |
| CN | 119776473 | A | 4/2025 |
| CN | 119824043 | A | 4/2025 |
| CN | 119842678 | A | 4/2025 |
| CN | 119874939 | A | 4/2025 |
| CN | 116083350 | B | 5/2025 |
| CN | 119912542 | A | 5/2025 |
| CN | 119913201 | A | 5/2025 |
| CN | 119932079 | A | 5/2025 |
| CN | 119950382 | A | 5/2025 |
| CN | 119979470 | A | 5/2025 |
| CN | 120040325 | A | 5/2025 |
| CN | 120060399 | A | 5/2025 |
| CN | 118186038 | B | 6/2025 |
| CN | 119530102 | B | 6/2025 |
| CN | 120098096 | A | 6/2025 |
| CN | 120098904 | A | 6/2025 |
| CN | 120098929 | A | 6/2025 |
| CN | 120136978 | A | 6/2025 |
| CN | 120137844 | A | 6/2025 |
| CN | 120137888 | A | 6/2025 |
| CN | 120138095 | A | 6/2025 |
| CN | 118440172 | B | 7/2025 |
| CN | 118791576 | B | 7/2025 |
| CN | 119177256 | B | 7/2025 |
| CN | 119776442 | B | 7/2025 |
| CN | 119979551 | B | 7/2025 |
| CN | 120240570 | A | 7/2025 |
| CN | 120241960 | A | 7/2025 |
| CN | 120248133 | A | 7/2025 |
| CN | 120272479 | A | 7/2025 |
| CN | 120289658 | A | 7/2025 |
| CN | 120361192 | A | 7/2025 |
| CN | 116284346 | B | 8/2025 |
| CN | 119823285 | B | 8/2025 |
| CN | 120400160 | A | 8/2025 |
| CN | 120425015 | A | 8/2025 |
| CN | 120247599 | B | 9/2025 |
| CN | 120249193 | A | 9/2025 |
| CN | 120590479 | A | 9/2025 |
| CN | 120665174 | A | 9/2025 |
| CN | 120700159 | A | 9/2025 |
| CN | 117305394 | B | 10/2025 |
| CN | 118421739 | B | 10/2025 |
| CN | 120365401 | B | 10/2025 |
| CN | 120733036 | A | 10/2025 |
| CN | 120757608 | A | 10/2025 |
| CN | 120796498 | A | 10/2025 |
| CN | 120131528 | B | 11/2025 |
| CN | 118235848 | B | 12/2025 |
| EP | 0234773 | B1 | 4/1992 |
| EP | 1096017 | A2 | 5/2001 |
| EP | 2708232 | B1 | 11/2016 |
| EP | 2965745 | B1 | 8/2017 |
| EP | 2853584 | B1 | 3/2021 |
| EP | 4108307 | A3 | 2/2023 |
| EP | 4328296 | A1 | 2/2024 |
| EP | 4418882 | A1 | 8/2024 |
| EP | 4445745 | A1 | 10/2024 |
| EP | 4501443 | A1 | 2/2025 |
| EP | 4624571 | A1 | 10/2025 |
| GB | 2385767 | A | 9/2003 |
| IN | 201621025611 | A | 2/2018 |
| IN | 202421035535 | A | 5/2024 |
| IN | 202421103034 | A | 1/2025 |
| IN | 202521005363 | A | 3/2025 |
| JP | 4635196 | B2 | 2/2011 |
| JP | 4978913 | B2 | 7/2012 |
| JP | 6089189 | B2 | 3/2017 |
| JP | 6351952 | B2 | 7/2018 |
| JP | 6901091 | B2 | 7/2021 |
| JP | 2023039157 | A | 3/2023 |
| JP | 2023055867 | | 4/2023 |
| JP | 7475873 | B2 | 4/2024 |
| KR | 101033738 | B1 | 5/2011 |
| KR | 101121077 | B1 | 6/2012 |
| KR | 101434734 | B1 | 9/2014 |
| KR | 101754272 | B1 | 7/2017 |
| KR | 101956097 | B1 | 3/2019 |
| KR | 101970888 | B1 | 4/2019 |
| KR | 102040203 | B1 | 11/2019 |
| KR | 102200324 | B1 | 1/2021 |
| KR | 20210105789 | A | 8/2021 |
| KR | 102362988 | B1 | 2/2022 |
| KR | 102414754 | B1 | 6/2022 |
| KR | 20230057206 | A | 4/2023 |
| KR | 102529976 | B1 | 5/2023 |
| KR | 20230079340 | A | 6/2023 |
| KR | 20230109353 | A | 7/2023 |
| KR | 102581772 | B1 | 9/2023 |
| KR | 20240077718 | A | 6/2024 |
| KR | 20240164155 | A | 11/2024 |
| KR | 20250073874 | A | 5/2025 |
| KR | 20250100942 | A | 7/2025 |
| KR | 102882918 | B1 | 11/2025 |
| RU | 2755539 | C1 | 9/2021 |
| TW | 200533742 | A | 10/2005 |
| TW | I715083 | B | 1/2021 |
| TW | 202111110 | A | 3/2021 |
| TW | 202239332 | | 10/2022 |
| TW | M638177 | U | 3/2023 |
| WO | 1995008630 | A1 | 3/1995 |
| WO | 1998037880 | A1 | 9/1998 |
| WO | 1999008539 | A1 | 2/1999 |
| WO | 1999063058 | A1 | 12/1999 |
| WO | 2000071728 | A1 | 11/2000 |
| WO | 0114529 | A1 | 3/2001 |
| WO | 2001060166 | A1 | 8/2001 |
| WO | 2001062947 | | 8/2001 |
| WO | 0164047 | A1 | 9/2001 |
| WO | 0190333 | A2 | 11/2001 |

(56) References Cited

FOREIGN PATENT DOCUMENTS

| | | | |
|---|---|---|---|
| WO | 0164047 | A9 | 6/2002 |
| WO | 0114529 | A9 | 9/2002 |
| WO | 2002067690 | A1 | 9/2002 |
| WO | 02095003 | A2 | 11/2002 |
| WO | 2002090527 | A1 | 11/2002 |
| WO | 0190333 | A3 | 1/2003 |
| WO | 03012058 | A2 | 2/2003 |
| WO | 2003045317 | A2 | 6/2003 |
| WO | 2003051908 | A1 | 6/2003 |
| WO | 03094835 | A2 | 11/2003 |
| WO | 03012058 | A3 | 12/2003 |
| WO | 2004005493 | A1 | 1/2004 |
| WO | 2004023887 | A1 | 3/2004 |
| WO | 2004055155 | A2 | 7/2004 |
| WO | 2004069298 | A1 | 8/2004 |
| WO | 02095003 | A3 | 9/2004 |
| WO | 2004055155 | A3 | 9/2004 |
| WO | 2004078924 | A3 | 5/2005 |
| WO | 2005083058 | A1 | 9/2005 |
| WO | 2005090564 | A1 | 9/2005 |
| WO | 2005120244 | A1 | 12/2005 |
| WO | 2005108617 | A3 | 2/2006 |
| WO | 2006028684 | A2 | 3/2006 |
| WO | 2006029197 | A1 | 3/2006 |
| WO | 2006029198 | A2 | 3/2006 |
| WO | 2006041429 | A2 | 4/2006 |
| WO | 2006029198 | A3 | 5/2006 |
| WO | 2006048783 | A2 | 5/2006 |
| WO | 2006053010 | A2 | 5/2006 |
| WO | 2006053010 | A3 | 7/2006 |
| WO | 2006048783 | A8 | 8/2006 |
| WO | 2006048783 | A3 | 11/2006 |
| WO | 2007005370 | A1 | 1/2007 |
| WO | 03094835 | A3 | 3/2007 |
| WO | 2006097110 | A3 | 4/2007 |
| WO | 2007049904 | A1 | 5/2007 |
| WO | 2006041429 | A3 | 6/2007 |
| WO | 2007042577 | A3 | 6/2007 |
| WO | 2007066694 | A1 | 6/2007 |
| WO | 2007079936 | A1 | 7/2007 |
| WO | 2007085412 | A1 | 8/2007 |
| WO | 2007085412 | B1 | 10/2007 |
| WO | 2007111105 | A1 | 10/2007 |
| WO | 2007141309 | A2 | 12/2007 |
| WO | 2007146689 | A2 | 12/2007 |
| WO | 2008036916 | A2 | 3/2008 |
| WO | 2007146689 | A3 | 4/2008 |
| WO | 2008038287 | A2 | 4/2008 |
| WO | 2007141309 | A3 | 5/2008 |
| WO | 2008051854 | A9 | 6/2008 |
| WO | 2008085879 | A2 | 7/2008 |
| WO | 2008106012 | A1 | 9/2008 |
| WO | 2008124133 | A1 | 10/2008 |
| WO | 2008128289 | A1 | 10/2008 |
| WO | 2008036916 | A3 | 11/2008 |
| WO | 2008085879 | A3 | 11/2008 |
| WO | 2008121563 | A3 | 11/2008 |
| WO | 2008134220 | A1 | 11/2008 |
| WO | 2008136398 | A1 | 11/2008 |
| WO | 2008141207 | A1 | 11/2008 |
| WO | 2009006930 | A1 | 1/2009 |
| WO | 2009006997 | A1 | 1/2009 |
| WO | 2009007852 | A2 | 1/2009 |
| WO | 2008033517 | A9 | 2/2009 |
| WO | 2009023562 | A2 | 2/2009 |
| WO | 2009036113 | A1 | 3/2009 |
| WO | 2009039001 | A1 | 3/2009 |
| WO | 2006028684 | A3 | 4/2009 |
| WO | 2008038287 | A3 | 4/2009 |
| WO | 2008133938 | A3 | 4/2009 |
| WO | 2009046978 | A1 | 4/2009 |
| WO | 2009047007 | A1 | 4/2009 |
| WO | 2009048119 | A1 | 4/2009 |
| WO | 2009023562 | A3 | 5/2009 |
| WO | 2009078333 | A1 | 6/2009 |
| WO | 2009007852 | A3 | 8/2009 |
| WO | 2009080912 | A3 | 8/2009 |
| WO | 2009114702 | A2 | 9/2009 |
| WO | 2009145875 | A1 | 12/2009 |
| WO | 2009149171 | A2 | 12/2009 |
| WO | 2009151541 | A1 | 12/2009 |
| WO | 2009152484 | A2 | 12/2009 |
| WO | 2009152485 | A2 | 12/2009 |
| WO | 2009156030 | A1 | 12/2009 |
| WO | 2009156413 | A1 | 12/2009 |
| WO | 2010009478 | A2 | 1/2010 |
| WO | 2008149353 | A3 | 2/2010 |
| WO | 2009114702 | A3 | 2/2010 |
| WO | 2009149171 | A3 | 3/2010 |
| WO | 2009152484 | A3 | 3/2010 |
| WO | 2010009478 | A3 | 3/2010 |
| WO | 2010022508 | A1 | 3/2010 |
| WO | 2010022509 | A1 | 3/2010 |
| WO | 2010033085 | A1 | 3/2010 |
| WO | 2009149171 | A4 | 5/2010 |
| WO | 2009152485 | A3 | 5/2010 |
| WO | 2010050448 | A1 | 5/2010 |
| WO | 2010072676 | A1 | 7/2010 |
| WO | 2010080826 | A1 | 7/2010 |
| WO | 2010086078 | A1 | 8/2010 |
| WO | 2010089151 | A1 | 8/2010 |
| WO | 2010092335 | A1 | 8/2010 |
| WO | 2010110767 | A1 | 9/2010 |
| WO | 2010080985 | A8 | 10/2010 |
| WO | 2010115185 | A1 | 10/2010 |
| WO | 2010089151 | A8 | 11/2010 |
| WO | 2010125006 | A1 | 11/2010 |
| WO | 2010129503 | A1 | 11/2010 |
| WO | 2010129600 | A2 | 11/2010 |
| WO | 2010135247 | A1 | 11/2010 |
| WO | 2010135588 | A2 | 11/2010 |
| WO | 2007146689 | A9 | 12/2010 |
| WO | 2010135588 | A3 | 1/2011 |
| WO | 2011008959 | A1 | 1/2011 |
| WO | 2011014363 | A1 | 2/2011 |
| WO | 2011014391 | A1 | 2/2011 |
| WO | 2010129600 | A3 | 4/2011 |
| WO | 2011011072 | A3 | 4/2011 |
| WO | 2011053281 | A1 | 5/2011 |
| WO | 2011056183 | A1 | 5/2011 |
| WO | 2011058558 | A2 | 5/2011 |
| WO | 2011060613 | A9 | 6/2011 |
| WO | 2011068526 | A1 | 6/2011 |
| WO | 2011073199 | A1 | 6/2011 |
| WO | 2011091111 | A1 | 7/2011 |
| WO | 2011058558 | A3 | 10/2011 |
| WO | 2011133902 | A2 | 10/2011 |
| WO | 2011134920 | A1 | 11/2011 |
| WO | 2011139804 | A2 | 11/2011 |
| WO | 2011133886 | A3 | 12/2011 |
| WO | 2011154525 | A1 | 12/2011 |
| WO | 2011159071 | A2 | 12/2011 |
| WO | 2011159359 | A2 | 12/2011 |
| WO | 2012019122 | A2 | 2/2012 |
| WO | 2012019160 | A1 | 2/2012 |
| WO | 2012027533 | A1 | 3/2012 |
| WO | 2012029909 | A1 | 3/2012 |
| WO | 2012040550 | A1 | 3/2012 |
| WO | 2011133902 | A3 | 4/2012 |
| WO | 2011139804 | A3 | 4/2012 |
| WO | 2011159895 | A3 | 5/2012 |
| WO | 2012019122 | A3 | 5/2012 |
| WO | 2011159071 | A3 | 6/2012 |
| WO | 2012078037 | A1 | 6/2012 |
| WO | 2012027209 | A3 | 7/2012 |
| WO | 2012097079 | A2 | 7/2012 |
| WO | 2012099279 | A1 | 7/2012 |
| WO | 2012099786 | A1 | 7/2012 |
| WO | 2012106759 | A1 | 8/2012 |
| WO | 2012109279 | A2 | 8/2012 |
| WO | 2012109279 | A3 | 10/2012 |
| WO | 2012145682 | A1 | 10/2012 |
| WO | 2012147048 | A2 | 11/2012 |
| WO | 2012154738 | A1 | 11/2012 |

(56) References Cited

FOREIGN PATENT DOCUMENTS

| | | | |
|---|---|---|---|
| WO | 2012158244 | A2 | 11/2012 |
| WO | 2012163368 | A1 | 12/2012 |
| WO | 2012166973 | A1 | 12/2012 |
| WO | 2012173078 | A1 | 12/2012 |
| WO | 2012147048 | A3 | 1/2013 |
| WO | 2012158244 | A3 | 1/2013 |
| WO | 2013010048 | A2 | 1/2013 |
| WO | 2013040688 | A1 | 3/2013 |
| WO | 2013010048 | A3 | 4/2013 |
| WO | 2013049247 | A1 | 4/2013 |
| WO | 2013049692 | A1 | 4/2013 |
| WO | 2012097079 | A3 | 6/2013 |
| WO | 2013082309 | A1 | 6/2013 |
| WO | 2013090769 | A2 | 6/2013 |
| WO | 2013090919 | A1 | 6/2013 |
| WO | 2013096386 | A1 | 6/2013 |
| WO | 2013106548 | A1 | 7/2013 |
| WO | 2013090769 | A3 | 8/2013 |
| WO | 2013116432 | A1 | 8/2013 |
| WO | 2013122864 | A1 | 8/2013 |
| WO | 2013148348 | A1 | 10/2013 |
| WO | 2013158312 | A1 | 10/2013 |
| WO | 2013166339 | A1 | 11/2013 |
| WO | 2013169802 | A1 | 11/2013 |
| WO | 2013170017 | A2 | 11/2013 |
| WO | 2013170636 | A1 | 11/2013 |
| WO | 2013172628 | A1 | 11/2013 |
| WO | 2013182553 | A2 | 12/2013 |
| WO | 2013184958 | A1 | 12/2013 |
| WO | 2013184960 | A2 | 12/2013 |
| WO | 2013184962 | A1 | 12/2013 |
| WO | 2013186294 | A1 | 12/2013 |
| WO | 2013182553 | A3 | 1/2014 |
| WO | 2013184962 | A4 | 1/2014 |
| WO | 2014010746 | A1 | 1/2014 |
| WO | 2013170017 | A3 | 2/2014 |
| WO | 2013184958 | A4 | 2/2014 |
| WO | 2013184960 | A3 | 3/2014 |
| WO | 2014037919 | A1 | 3/2014 |
| WO | 2014046293 | A1 | 3/2014 |
| WO | 2014060898 | A2 | 4/2014 |
| WO | 2014071419 | A2 | 5/2014 |
| WO | 2014074012 | A1 | 5/2014 |
| WO | 2014075807 | A1 | 5/2014 |
| WO | 2014052451 | A3 | 6/2014 |
| WO | 2014060898 | A3 | 6/2014 |
| WO | 2014084027 | A1 | 6/2014 |
| WO | 2014094386 | A1 | 6/2014 |
| WO | 2014110512 | A1 | 7/2014 |
| WO | 2014144198 | A1 | 9/2014 |
| WO | 2014145593 | A2 | 9/2014 |
| WO | 2014148361 | A1 | 9/2014 |
| WO | 2014152603 | A1 | 9/2014 |
| WO | 2014182242 | A1 | 11/2014 |
| WO | 2014199114 | A1 | 12/2014 |
| WO | 2014145593 | A3 | 1/2015 |
| WO | 2015003773 | A1 | 1/2015 |
| WO | 2015027209 | A2 | 2/2015 |
| WO | 2015038988 | A1 | 3/2015 |
| WO | 2015047298 | A1 | 4/2015 |
| WO | 2015057980 | A1 | 4/2015 |
| WO | 2015061361 | A1 | 4/2015 |
| WO | 2015027209 | A3 | 5/2015 |
| WO | 2015066377 | A1 | 5/2015 |
| WO | 2015070372 | A1 | 5/2015 |
| WO | 2015086783 | A1 | 6/2015 |
| WO | 2015095809 | A1 | 6/2015 |
| WO | 2015101510 | A1 | 7/2015 |
| WO | 2015102528 | A1 | 7/2015 |
| WO | 2015118233 | A1 | 8/2015 |
| WO | 2015120174 | A1 | 8/2015 |
| WO | 2015121471 | A1 | 8/2015 |
| WO | 2015140708 | A1 | 9/2015 |
| WO | 2015148515 | A1 | 10/2015 |
| WO | 2015165583 | A1 | 11/2015 |
| WO | 2015171644 | A1 | 11/2015 |
| WO | 2015188131 | A1 | 12/2015 |
| WO | 2015191462 | A1 | 12/2015 |
| WO | 2015194208 | A1 | 12/2015 |
| WO | 2015172002 | A3 | 1/2016 |
| WO | 2016010165 | A1 | 1/2016 |
| WO | 2016016894 | A1 | 2/2016 |
| WO | 2016023775 | A1 | 2/2016 |
| WO | 2016027850 | A1 | 2/2016 |
| WO | 2010042189 | A3 | 3/2016 |
| WO | 2015185691 | A9 | 3/2016 |
| WO | 2016033241 | A1 | 3/2016 |
| WO | 2016036275 | A1 | 3/2016 |
| WO | 2016065326 | A2 | 4/2016 |
| WO | 2016073858 | A1 | 5/2016 |
| WO | 2016076761 | A1 | 5/2016 |
| WO | 2016065326 | A3 | 6/2016 |
| WO | 2016087560 | A1 | 6/2016 |
| WO | 2016091349 | A1 | 6/2016 |
| WO | 2016099971 | A1 | 6/2016 |
| WO | 2016110786 | A1 | 7/2016 |
| WO | 2015171928 | A8 | 8/2016 |
| WO | 2016120594 | A1 | 8/2016 |
| WO | 2016025750 | A3 | 9/2016 |
| WO | 2016139340 | A1 | 9/2016 |
| WO | 2016143826 | A1 | 9/2016 |
| WO | 2016110786 | A8 | 10/2016 |
| WO | 2016156476 | A1 | 10/2016 |
| WO | 2016166310 | A1 | 10/2016 |
| WO | 2016168454 | A1 | 10/2016 |
| WO | 2016057529 | A3 | 11/2016 |
| WO | 2016176456 | A1 | 11/2016 |
| WO | 2016190394 | A1 | 12/2016 |
| WO | 2016195157 | A1 | 12/2016 |
| WO | 2017011598 | A1 | 1/2017 |
| WO | 2017025210 | A1 | 2/2017 |
| WO | 2017026462 | A1 | 2/2017 |
| WO | 2017042242 | A1 | 3/2017 |
| WO | 2017044864 | A1 | 3/2017 |
| WO | 2017049094 | A1 | 3/2017 |
| WO | 2017062517 | A1 | 4/2017 |
| WO | 2017066471 | A1 | 4/2017 |
| WO | 2017070303 | A1 | 4/2017 |
| WO | 2017075260 | A1 | 5/2017 |
| WO | 2017078176 | A1 | 5/2017 |
| WO | 2017081214 | A1 | 5/2017 |
| WO | 2017085086 | A1 | 5/2017 |
| WO | 2017089016 | A1 | 6/2017 |
| WO | 2017091943 | A1 | 6/2017 |
| WO | 2017097983 | A1 | 6/2017 |
| WO | 2017116449 | A1 | 7/2017 |
| WO | 2017117091 | A1 | 7/2017 |
| WO | 2017117559 | A1 | 7/2017 |
| WO | 2017124100 | A1 | 7/2017 |
| WO | 2016176456 | A9 | 8/2017 |
| WO | 2017132185 | A1 | 8/2017 |
| WO | 2017143071 | A1 | 8/2017 |
| WO | 2017146646 | A1 | 8/2017 |
| WO | 2017147216 | A1 | 8/2017 |
| WO | 2017149025 | A1 | 9/2017 |
| WO | 2017165244 | A1 | 9/2017 |
| WO | 2017174329 | A1 | 10/2017 |
| WO | 2017175086 | A1 | 10/2017 |
| WO | 2017177169 | A1 | 10/2017 |
| WO | 2017180669 | A1 | 10/2017 |
| WO | 2017189683 | A1 | 11/2017 |
| WO | 2017191691 | A1 | 11/2017 |
| WO | 2017193087 | A1 | 11/2017 |
| WO | 2017196175 | A1 | 11/2017 |
| WO | 2017207822 | A1 | 12/2017 |
| WO | 2017216620 | A1 | 12/2017 |
| WO | 2017223457 | A1 | 12/2017 |
| WO | 2018007597 | A1 | 1/2018 |
| WO | 2018011805 | A2 | 1/2018 |
| WO | 2018016814 | A1 | 1/2018 |
| WO | 2018017419 | A1 | 1/2018 |
| WO | 2017193087 | A8 | 2/2018 |
| WO | 2018011805 | A3 | 2/2018 |
| WO | 2018033542 | A1 | 2/2018 |

(56) References Cited

FOREIGN PATENT DOCUMENTS

| | | | |
|---|---|---|---|
| WO | 2018034655 | A1 | 2/2018 |
| WO | 2018035158 | A1 | 2/2018 |
| WO | 2018038711 | A1 | 3/2018 |
| WO | 2018011805 | A9 | 4/2018 |
| WO | 2018049025 | A3 | 5/2018 |
| WO | 2018096343 | A1 | 5/2018 |
| WO | 2018102780 | A1 | 6/2018 |
| WO | 2018104197 | A1 | 6/2018 |
| WO | 2017100313 | A8 | 7/2018 |
| WO | 2018081476 | A9 | 7/2018 |
| WO | 2018125631 | A1 | 7/2018 |
| WO | 2018132494 | A1 | 7/2018 |
| WO | 2018138515 | A1 | 8/2018 |
| WO | 2018144965 | A1 | 8/2018 |
| WO | 2018146689 | A1 | 8/2018 |
| WO | 2018148376 | A1 | 8/2018 |
| WO | 2018155913 | A1 | 8/2018 |
| WO | 2018162346 | A1 | 9/2018 |
| WO | 2018162353 | A1 | 9/2018 |
| WO | 2018167621 | A1 | 9/2018 |
| WO | 2018185025 | A1 | 10/2018 |
| WO | 2018185634 | A1 | 10/2018 |
| WO | 2018187568 | A1 | 10/2018 |
| WO | 2018189738 | A1 | 10/2018 |
| WO | 2018204497 | A1 | 11/2018 |
| WO | 2018204847 | A2 | 11/2018 |
| WO | 2018205985 | A1 | 11/2018 |
| WO | 2018208628 | A1 | 11/2018 |
| WO | 2018208836 | A1 | 11/2018 |
| WO | 2017214709 | A8 | 12/2018 |
| WO | 2018227016 | A1 | 12/2018 |
| WO | 2018232750 | A1 | 12/2018 |
| WO | 2018234430 | A1 | 12/2018 |
| WO | 2019010116 | A1 | 1/2019 |
| WO | 2019014652 | A1 | 1/2019 |
| WO | 2019016795 | A1 | 1/2019 |
| WO | 2019018660 | A1 | 1/2019 |
| WO | 2019030069 | A2 | 2/2019 |
| WO | 2019032725 | A1 | 2/2019 |
| WO | 2019046782 | A2 | 3/2019 |
| WO | 2019032725 | A8 | 4/2019 |
| WO | 2019067966 | A1 | 4/2019 |
| WO | 2019046782 | A3 | 5/2019 |
| WO | 2019092054 | A1 | 5/2019 |
| WO | 2019098310 | A1 | 5/2019 |
| WO | 2019088496 | A3 | 6/2019 |
| WO | 2019108756 | A1 | 6/2019 |
| WO | 2019113556 | A1 | 6/2019 |
| WO | 2019115675 | A1 | 6/2019 |
| WO | 2019122239 | A1 | 6/2019 |
| WO | 2019126438 | A1 | 6/2019 |
| WO | 2019126748 | A1 | 6/2019 |
| WO | 2019088528 | A3 | 7/2019 |
| WO | 2019140260 | A1 | 7/2019 |
| WO | 2019144968 | A1 | 8/2019 |
| WO | 2019171298 | A1 | 9/2019 |
| WO | 2019178508 | A1 | 9/2019 |
| WO | 2019181999 | A1 | 9/2019 |
| WO | 2019182156 | A1 | 9/2019 |
| WO | 2019169233 | A9 | 10/2019 |
| WO | 2019191495 | A1 | 10/2019 |
| WO | 2019209892 | A1 | 10/2019 |
| WO | 2019210870 | A1 | 11/2019 |
| WO | 2019211189 | A1 | 11/2019 |
| WO | 2019212293 | A1 | 11/2019 |
| WO | 2019212973 | A1 | 11/2019 |
| WO | 2019224467 | A1 | 11/2019 |
| WO | 2019231848 | A1 | 12/2019 |
| WO | 2019234442 | A1 | 12/2019 |
| WO | 2019240221 | A1 | 12/2019 |
| WO | 2019245278 | A1 | 12/2019 |
| WO | 2019246066 | A1 | 12/2019 |
| WO | 2020006409 | A1 | 1/2020 |
| WO | 2020016655 | A2 | 1/2020 |
| WO | 2020023450 | A1 | 1/2020 |
| WO | 2020030628 | A1 | 2/2020 |
| WO | 2020036184 | A1 | 2/2020 |
| WO | 2020016655 | A3 | 3/2020 |
| WO | 2020047124 | A1 | 3/2020 |
| WO | 2020047300 | A1 | 3/2020 |
| WO | 2020049535 | A1 | 3/2020 |
| WO | 2020051042 | A1 | 3/2020 |
| WO | 2020056343 | A1 | 3/2020 |
| WO | 2019115675 | A9 | 4/2020 |
| WO | 2020067502 | A1 | 4/2020 |
| WO | 2020072125 | A1 | 4/2020 |
| WO | 2020072140 | A1 | 4/2020 |
| WO | 2020076776 | A1 | 4/2020 |
| WO | 2020077144 | A1 | 4/2020 |
| WO | 2020081097 | A1 | 4/2020 |
| WO | 2020081128 | A1 | 4/2020 |
| WO | 2020095305 | A1 | 5/2020 |
| WO | 2020097083 | A1 | 5/2020 |
| WO | 2020100143 | A1 | 5/2020 |
| WO | 2020104650 | A1 | 5/2020 |
| WO | 2020106743 | A1 | 5/2020 |
| WO | 2020116765 | A1 | 6/2020 |
| WO | 2020120251 | A2 | 6/2020 |
| WO | 2020123876 | A1 | 6/2020 |
| WO | 2020131661 | A1 | 6/2020 |
| WO | 2020120251 | A3 | 7/2020 |
| WO | 2020141236 | A1 | 7/2020 |
| WO | 2020144166 | A1 | 7/2020 |
| WO | 2020146368 | A1 | 7/2020 |
| WO | 2020146373 | A1 | 7/2020 |
| WO | 2020148480 | A1 | 7/2020 |
| WO | 2020150078 | A1 | 7/2020 |
| WO | 2020155807 | A1 | 8/2020 |
| WO | 2020167676 | A1 | 8/2020 |
| WO | 2020169703 | A1 | 8/2020 |
| WO | 2020160187 | A3 | 9/2020 |
| WO | 2020176224 | A1 | 9/2020 |
| WO | 2020176758 | A1 | 9/2020 |
| WO | 2020179257 | A1 | 9/2020 |
| WO | 2020182970 | A1 | 9/2020 |
| WO | 2020201296 | A1 | 10/2020 |
| WO | 2020206162 | A1 | 10/2020 |
| WO | 2020206470 | A1 | 10/2020 |
| WO | 2020210398 | A1 | 10/2020 |
| WO | 2020219755 | A1 | 10/2020 |
| WO | 2020222239 | A1 | 11/2020 |
| WO | 2020225709 | A1 | 11/2020 |
| WO | 2020230138 | A1 | 11/2020 |
| WO | 2020234425 | A1 | 11/2020 |
| WO | 2020237021 | A1 | 11/2020 |
| WO | 2020223381 | A3 | 12/2020 |
| WO | 2020238961 | A1 | 12/2020 |
| WO | 2020239807 | A1 | 12/2020 |
| WO | 2020243324 | A1 | 12/2020 |
| WO | 2020243695 | A1 | 12/2020 |
| WO | 2020245355 | A1 | 12/2020 |
| WO | 2020249544 | A1 | 12/2020 |
| WO | 2020251537 | A1 | 12/2020 |
| WO | 2020252388 | A1 | 12/2020 |
| WO | 2020264200 | A1 | 12/2020 |
| WO | 2021003188 | A1 | 1/2021 |
| WO | 2021013698 | A1 | 1/2021 |
| WO | 2021015571 | A1 | 1/2021 |
| WO | 2021016523 | A1 | 1/2021 |
| WO | 2021021968 | A1 | 2/2021 |
| WO | 2021028674 | A1 | 2/2021 |
| WO | 2021030412 | A1 | 2/2021 |
| WO | 2021032637 | A1 | 2/2021 |
| WO | 2021041461 | A1 | 3/2021 |
| WO | 2021044377 | A1 | 3/2021 |
| WO | 2021044379 | A1 | 3/2021 |
| WO | 2021046305 | A1 | 3/2021 |
| WO | 2021047495 | A1 | 3/2021 |
| WO | 2021048325 | A1 | 3/2021 |
| WO | 2021051054 | A1 | 3/2021 |
| WO | 2021055366 | A1 | 3/2021 |
| WO | 2021055579 | A1 | 3/2021 |
| WO | 2021055592 | A1 | 3/2021 |
| WO | 2021055616 | A1 | 3/2021 |

(56) References Cited

FOREIGN PATENT DOCUMENTS

| | | | |
|---|---|---|---|
| WO | 2021055841 | A1 | 3/2021 |
| WO | 2021061832 | A1 | 4/2021 |
| WO | 2021061900 | A1 | 4/2021 |
| WO | 2021066113 | A1 | 4/2021 |
| WO | 2021067641 | A1 | 4/2021 |
| WO | 2021069353 | A1 | 4/2021 |
| WO | 2021074556 | A1 | 4/2021 |
| WO | 2021084159 | A1 | 5/2021 |
| WO | 2021085637 | A1 | 5/2021 |
| WO | 2021087404 | A1 | 5/2021 |
| WO | 2021089355 | A1 | 5/2021 |
| WO | 2021089661 | A1 | 5/2021 |
| WO | 2021092049 | A1 | 5/2021 |
| WO | 2021092051 | A1 | 5/2021 |
| WO | 2021094500 | A1 | 5/2021 |
| WO | 2021094826 | A1 | 5/2021 |
| WO | 2021095034 | A1 | 5/2021 |
| WO | 2021102375 | A1 | 5/2021 |
| WO | 2021106697 | A1 | 6/2021 |
| WO | 2021107473 | A1 | 6/2021 |
| WO | 2021110712 | A1 | 6/2021 |
| WO | 2021110767 | A1 | 6/2021 |
| WO | 2021111196 | A1 | 6/2021 |
| WO | 2021111219 | A1 | 6/2021 |
| WO | 2021111263 | A1 | 6/2021 |
| WO | 2021111270 | A1 | 6/2021 |
| WO | 2021116361 | A1 | 6/2021 |
| WO | 2021126584 | A1 | 6/2021 |
| WO | 2020201296 | A8 | 7/2021 |
| WO | 2021133602 | A1 | 7/2021 |
| WO | 2021133939 | A1 | 7/2021 |
| WO | 2021134512 | A1 | 7/2021 |
| WO | 2021138482 | A1 | 7/2021 |
| WO | 2021138674 | A1 | 7/2021 |
| WO | 2021140656 | A1 | 7/2021 |
| WO | 2021142376 | A1 | 7/2021 |
| WO | 2021146627 | A1 | 7/2021 |
| WO | 2021148663 | A1 | 7/2021 |
| WO | 2021148955 | A1 | 7/2021 |
| WO | 2021148960 | A1 | 7/2021 |
| WO | 2021149906 | A1 | 7/2021 |
| WO | 2021150837 | A1 | 7/2021 |
| WO | 2021151025 | A1 | 7/2021 |
| WO | 2021152536 | A1 | 8/2021 |
| WO | 2021158103 | A1 | 8/2021 |
| WO | 2021158104 | A1 | 8/2021 |
| WO | 2021158105 | A1 | 8/2021 |
| WO | 2021158831 | A1 | 8/2021 |
| WO | 2021160301 | A1 | 8/2021 |
| WO | 2021161397 | A1 | 8/2021 |
| WO | 2021163203 | A1 | 8/2021 |
| WO | 2021163216 | A1 | 8/2021 |
| WO | 2021163438 | A1 | 8/2021 |
| WO | 2021163481 | A1 | 8/2021 |
| WO | 2021168042 | A1 | 8/2021 |
| WO | 2021141692 | A3 | 9/2021 |
| WO | 2021173974 | A1 | 9/2021 |
| WO | 2021178254 | A1 | 9/2021 |
| WO | 2021178928 | A2 | 9/2021 |
| WO | 2021181235 | A1 | 9/2021 |
| WO | 2021191443 | A1 | 9/2021 |
| WO | 2021191623 | A1 | 9/2021 |
| WO | 2021191624 | A1 | 9/2021 |
| WO | 2021191913 | A1 | 9/2021 |
| WO | 2021195259 | A1 | 9/2021 |
| WO | 2021178928 | A3 | 10/2021 |
| WO | 2021195718 | A1 | 10/2021 |
| WO | 2021198169 | A1 | 10/2021 |
| WO | 2021207293 | A1 | 10/2021 |
| WO | 2021207401 | A1 | 10/2021 |
| WO | 2021207755 | A1 | 10/2021 |
| WO | 2021211841 | A1 | 10/2021 |
| WO | 2021214345 | A1 | 10/2021 |
| WO | 2021216460 | A1 | 10/2021 |
| WO | 2021216583 | A1 | 10/2021 |
| WO | 2021219823 | A1 | 11/2021 |
| WO | 2021220004 | A1 | 11/2021 |
| WO | 2021224434 | A1 | 11/2021 |
| WO | 2021231372 | A1 | 11/2021 |
| WO | 2021231569 | A1 | 11/2021 |
| WO | 2021234348 | A1 | 11/2021 |
| WO | 2021239046 | A1 | 12/2021 |
| WO | 2021239908 | A2 | 12/2021 |
| WO | 2021245711 | A1 | 12/2021 |
| WO | 2021248141 | A1 | 12/2021 |
| WO | 2021248158 | A1 | 12/2021 |
| WO | 2021250292 | A1 | 12/2021 |
| WO | 2021250407 | A1 | 12/2021 |
| WO | 2021251387 | A1 | 12/2021 |
| WO | 2021255435 | A1 | 12/2021 |
| WO | 2021262783 | A1 | 12/2021 |
| WO | 2021263282 | A1 | 12/2021 |
| WO | 2022003700 | A1 | 1/2022 |
| WO | 2022004079 | A1 | 1/2022 |
| WO | 2022008424 | A1 | 1/2022 |
| WO | 2022011163 | A1 | 1/2022 |
| WO | 2022024119 | A1 | 2/2022 |
| WO | 2022026999 | A1 | 2/2022 |
| WO | 2022034092 | A1 | 2/2022 |
| WO | 2022034211 | A1 | 2/2022 |
| WO | 2022036370 | A1 | 2/2022 |
| WO | 2022036371 | A1 | 2/2022 |
| WO | 2022037481 | A1 | 2/2022 |
| WO | 2022038240 | A2 | 2/2022 |
| WO | 2022038241 | A1 | 2/2022 |
| WO | 2022039998 | A1 | 2/2022 |
| WO | 2022040375 | A1 | 2/2022 |
| WO | 2022020431 | A3 | 3/2022 |
| WO | 2022047263 | A1 | 3/2022 |
| WO | 2022049217 | A1 | 3/2022 |
| WO | 2022050733 | A1 | 3/2022 |
| WO | 2022052877 | A1 | 3/2022 |
| WO | 2022053706 | A1 | 3/2022 |
| WO | 2022067034 | A1 | 3/2022 |
| WO | 2021239908 | A3 | 4/2022 |
| WO | 2021263179 | A9 | 4/2022 |
| WO | 2022069613 | A1 | 4/2022 |
| WO | 2022079717 | A1 | 4/2022 |
| WO | 2022079718 | A1 | 4/2022 |
| WO | 2022081511 | A1 | 4/2022 |
| WO | 2022087509 | A1 | 4/2022 |
| WO | 2022038240 | A3 | 5/2022 |
| WO | 2022087750 | A1 | 5/2022 |
| WO | 2022093846 | A1 | 5/2022 |
| WO | 2022094418 | A1 | 5/2022 |
| WO | 2022096664 | A1 | 5/2022 |
| WO | 2022097139 | A1 | 5/2022 |
| WO | 2022097716 | A1 | 5/2022 |
| WO | 2022098213 | A1 | 5/2022 |
| WO | 2022104373 | A1 | 5/2022 |
| WO | 2022112593 | A1 | 6/2022 |
| WO | 2022114955 | A1 | 6/2022 |
| WO | 2022115033 | A1 | 6/2022 |
| WO | 2022115289 | A2 | 6/2022 |
| WO | 2022115609 | A1 | 6/2022 |
| WO | 2022117750 | A1 | 6/2022 |
| WO | 2022121509 | A1 | 6/2022 |
| WO | 2022122548 | A1 | 6/2022 |
| WO | 2022123519 | A2 | 6/2022 |
| WO | 2022125590 | A1 | 6/2022 |
| WO | 2022125793 | A1 | 6/2022 |
| WO | 2022125809 | A1 | 6/2022 |
| WO | 2022129862 | A1 | 6/2022 |
| WO | 2022132059 | A1 | 6/2022 |
| WO | 2022132983 | A1 | 6/2022 |
| WO | 2022139499 | A1 | 6/2022 |
| WO | 2022140185 | A1 | 6/2022 |
| WO | 2022140187 | A1 | 6/2022 |
| WO | 2022140210 | A1 | 6/2022 |
| WO | 2022140389 | A1 | 6/2022 |
| WO | 2022114955 | A8 | 7/2022 |
| WO | 2022115289 | A3 | 7/2022 |
| WO | 2022115506 | A3 | 7/2022 |
| WO | 2022123519 | A3 | 7/2022 |

(56) References Cited

FOREIGN PATENT DOCUMENTS

| | | | | |
|---|---|---|---|---|
| WO | 2022125587 | A9 | 7/2022 | |
| WO | 2022144434 | A1 | 7/2022 | |
| WO | 2022147107 | A1 | 7/2022 | |
| WO | 2022147184 | A1 | 7/2022 | |
| WO | 2022153957 | A1 | 7/2022 | |
| WO | 2022155578 | A1 | 7/2022 | |
| WO | 2022156939 | A1 | 7/2022 | |
| WO | 2022159959 | A1 | 7/2022 | |
| WO | 2021222479 | A9 | 8/2022 | |
| WO | 2022172000 | A1 | 8/2022 | |
| WO | 2022174030 | A1 | 8/2022 | |
| WO | 2022178357 | A1 | 8/2022 | |
| WO | WO-2022171696 | A1 * | 8/2022 | ............. A23J 1/005 |
| WO | 2021239908 | A9 | 9/2022 | |
| WO | 2022187181 | A1 | 9/2022 | |
| WO | 2022187745 | A1 | 9/2022 | |
| WO | 2022189505 | A1 | 9/2022 | |
| WO | 2022189704 | A1 | 9/2022 | |
| WO | 2022192426 | A1 | 9/2022 | |
| WO | 2022192429 | A1 | 9/2022 | |
| WO | 2022192434 | A1 | 9/2022 | |
| WO | 2022192441 | A1 | 9/2022 | |
| WO | 2022192446 | A1 | 9/2022 | |
| WO | 2022192448 | A1 | 9/2022 | |
| WO | 2022192454 | A1 | 9/2022 | |
| WO | 2022192455 | A1 | 9/2022 | |
| WO | 2022192694 | A1 | 9/2022 | |
| WO | 2022196710 | A1 | 9/2022 | |
| WO | 2022197816 | A1 | 9/2022 | |
| WO | 2022203513 | A1 | 9/2022 | |
| WO | 2022204120 | A1 | 9/2022 | |
| WO | 2022204166 | A1 | 9/2022 | |
| WO | 2022204738 | A1 | 10/2022 | |
| WO | 2022207963 | A1 | 10/2022 | |
| WO | 2022208525 | A1 | 10/2022 | |
| WO | 2022211461 | A1 | 10/2022 | |
| WO | 2022212602 | A1 | 10/2022 | |
| WO | 2022215055 | A1 | 10/2022 | |
| WO | 2022216857 | A1 | 10/2022 | |
| WO | 2022218413 | A1 | 10/2022 | |
| WO | 2022221549 | A1 | 10/2022 | |
| WO | 2022225593 | A1 | 10/2022 | |
| WO | 2022225880 | A1 | 10/2022 | |
| WO | 2022225974 | A1 | 10/2022 | |
| WO | 2022149142 | A3 | 11/2022 | |
| WO | 2022178357 | A8 | 11/2022 | |
| WO | 2022221261 | A3 | 11/2022 | |
| WO | 2022229500 | A1 | 11/2022 | |
| WO | 2022229501 | A1 | 11/2022 | |
| WO | 2022229502 | A1 | 11/2022 | |
| WO | 2022229503 | A1 | 11/2022 | |
| WO | 2022229504 | A1 | 11/2022 | |
| WO | 2022229507 | A1 | 11/2022 | |
| WO | 2022229508 | A1 | 11/2022 | |
| WO | 2022232322 | A1 | 11/2022 | |
| WO | 2022234586 | A1 | 11/2022 | |
| WO | 2022235553 | A1 | 11/2022 | |
| WO | 2022235688 | A1 | 11/2022 | |
| WO | 2022238867 | A1 | 11/2022 | |
| WO | 2022245844 | A1 | 11/2022 | |
| WO | 2022246063 | A1 | 11/2022 | |
| WO | 2022225943 | A3 | 12/2022 | |
| WO | 2022248594 | A1 | 12/2022 | |
| WO | 2022251580 | A1 | 12/2022 | |
| WO | 2022259254 | A1 | 12/2022 | |
| WO | 2022261434 | A1 | 12/2022 | |
| WO | 2022261647 | A1 | 12/2022 | |
| WO | 2022266648 | A1 | 12/2022 | |
| WO | 2022268842 | A1 | 12/2022 | |
| WO | 2022270598 | A1 | 12/2022 | |
| WO | 2022270598 | A5 | 12/2022 | |
| WO | 2022236080 | A3 | 1/2023 | |
| WO | 2023002292 | A1 | 1/2023 | |
| WO | 2023003470 | A1 | 1/2023 | |
| WO | 2023003471 | A1 | 1/2023 | |
| WO | 2023003804 | A1 | 1/2023 | |
| WO | 2023004430 | A1 | 1/2023 | |
| WO | 2023275356 | A1 | 1/2023 | |
| WO | 2023277150 | A1 | 1/2023 | |
| WO | 2023278117 | A1 | 1/2023 | |
| WO | 2023278137 | A1 | 1/2023 | |
| WO | 2023278301 | A1 | 1/2023 | |
| WO | 2023278306 | A1 | 1/2023 | |
| WO | 2023278557 | A1 | 1/2023 | |
| WO | 2023279983 | A1 | 1/2023 | |
| WO | 2023281114 | A1 | 1/2023 | |
| WO | 2023281512 | A1 | 1/2023 | |
| WO | 2023282762 | A1 | 1/2023 | |
| WO | 2023285813 | A1 | 1/2023 | |
| WO | WO-2023278317 | A1 * | 1/2023 | |
| WO | 2022241289 | A3 | 2/2023 | |
| WO | 2023004515 | A1 | 2/2023 | |
| WO | 2023006897 | A1 | 2/2023 | |
| WO | 2023007050 | A1 | 2/2023 | |
| WO | 2023012523 | A1 | 2/2023 | |
| WO | 2023014712 | A1 | 2/2023 | |
| WO | 2023015317 | A1 | 2/2023 | |
| WO | 2023016357 | A1 | 2/2023 | |
| WO | 2023017509 | A1 | 2/2023 | |
| WO | 2023018995 | A1 | 2/2023 | |
| WO | 2023019203 | A1 | 2/2023 | |
| WO | 2023023857 | A1 | 3/2023 | |
| WO | 2023034384 | A1 | 3/2023 | |
| WO | 2023038547 | A1 | 3/2023 | |
| WO | 2023049162 | A1 | 3/2023 | |
| WO | 2023049537 | A1 | 3/2023 | |
| WO | 2023054556 | A1 | 4/2023 | |
| WO | 2023059044 | A1 | 4/2023 | |
| WO | 2023062015 | A1 | 4/2023 | |
| WO | 2023063468 | A1 | 4/2023 | |
| WO | 2023066646 | A1 | 4/2023 | |
| WO | 2023067595 | A1 | 4/2023 | |
| WO | 2023069931 | A1 | 4/2023 | |
| WO | 2023069991 | A1 | 4/2023 | |
| WO | 2023074607 | A1 | 5/2023 | |
| WO | 2023080894 | A1 | 5/2023 | |
| WO | 2023081615 | A1 | 5/2023 | |
| WO | 2023081618 | A1 | 5/2023 | |
| WO | 2023086502 | A1 | 5/2023 | |
| WO | 2023087033 | A1 | 5/2023 | |
| WO | 2023089568 | A1 | 5/2023 | |
| WO | 2023091821 | A1 | 5/2023 | |
| WO | 2022174030 | A9 | 6/2023 | |
| WO | 2023067081 | A3 | 6/2023 | |
| WO | 2023094619 | A1 | 6/2023 | |
| WO | 2023099413 | A1 | 6/2023 | |
| WO | 2023104984 | A1 | 6/2023 | |
| WO | 2023106300 | A1 | 6/2023 | |
| WO | 2023112952 | A1 | 6/2023 | |
| WO | 2023114918 | A1 | 6/2023 | |
| WO | 2023118412 | A1 | 6/2023 | |
| WO | 2023118414 | A1 | 6/2023 | |
| WO | 2023118597 | A1 | 6/2023 | |
| WO | 2023118872 | A1 | 6/2023 | |
| WO | 2023122133 | A1 | 6/2023 | |
| WO | 2023122688 | A1 | 6/2023 | |
| WO | 2022232322 | A9 | 7/2023 | |
| WO | 2023129418 | A1 | 7/2023 | |
| WO | 2023129971 | A2 | 7/2023 | |
| WO | 2023132371 | A1 | 7/2023 | |
| WO | 2023139493 | A1 | 7/2023 | |
| WO | 2023081816 | A3 | 8/2023 | |
| WO | 2023133568 | A3 | 8/2023 | |
| WO | 2023144148 | A1 | 8/2023 | |
| WO | 2023144369 | A1 | 8/2023 | |
| WO | 2023147288 | A1 | 8/2023 | |
| WO | 2023148598 | A1 | 8/2023 | |
| WO | 2023150293 | A2 | 8/2023 | |
| WO | 2023150555 | A1 | 8/2023 | |
| WO | 2023152487 | A1 | 8/2023 | |
| WO | 2023152488 | A1 | 8/2023 | |
| WO | 2023152489 | A1 | 8/2023 | |
| WO | 2023152492 | A1 | 8/2023 | |
| WO | 2023152493 | A1 | 8/2023 | |

(56) References Cited

FOREIGN PATENT DOCUMENTS

| | | | |
|---|---|---|---|
| WO | 2023156933 | A1 | 8/2023 |
| WO | 2023164573 | A1 | 8/2023 |
| WO | 2023146852 | A3 | 9/2023 |
| WO | 2023150293 | A3 | 9/2023 |
| WO | 2023150503 | A3 | 9/2023 |
| WO | 2023170280 | A1 | 9/2023 |
| WO | 2023170287 | A1 | 9/2023 |
| WO | 2023170643 | A1 | 9/2023 |
| WO | 2023172323 | A1 | 9/2023 |
| WO | 2023172343 | A1 | 9/2023 |
| WO | 2023176862 | A1 | 9/2023 |
| WO | 2023180600 | A1 | 9/2023 |
| WO | 2023181040 | A1 | 9/2023 |
| WO | 2022240910 | A8 | 10/2023 |
| WO | 2023186698 | A1 | 10/2023 |
| WO | 2023187031 | A1 | 10/2023 |
| WO | 2023187771 | A1 | 10/2023 |
| WO | 2023192991 | A1 | 10/2023 |
| WO | 2023192995 | A2 | 10/2023 |
| WO | 2023194619 | A1 | 10/2023 |
| WO | 2023194620 | A1 | 10/2023 |
| WO | 2023196500 | A1 | 10/2023 |
| WO | 2023197883 | A1 | 10/2023 |
| WO | 2023200008 | A1 | 10/2023 |
| WO | 2023201027 | A1 | 10/2023 |
| WO | 2023201048 | A2 | 10/2023 |
| WO | 2023201349 | A1 | 10/2023 |
| WO | 2023205677 | A1 | 10/2023 |
| WO | 2023178084 | A3 | 11/2023 |
| WO | 2023192995 | A3 | 11/2023 |
| WO | 2023201048 | A3 | 11/2023 |
| WO | 2023205656 | A3 | 11/2023 |
| WO | 2023211696 | A1 | 11/2023 |
| WO | 2023211726 | A1 | 11/2023 |
| WO | 2023212122 | A1 | 11/2023 |
| WO | 2023212677 | A2 | 11/2023 |
| WO | 2023212722 | A1 | 11/2023 |
| WO | 2023215542 | A1 | 11/2023 |
| WO | 2023220002 | A1 | 11/2023 |
| WO | 2023223083 | A1 | 11/2023 |
| WO | 2023224484 | A1 | 11/2023 |
| WO | 2023225686 | A1 | 11/2023 |
| WO | 2023225687 | A1 | 11/2023 |
| WO | 2023225995 | A1 | 11/2023 |
| WO | 2023229973 | A1 | 11/2023 |
| WO | 2023225662 | A3 | 12/2023 |
| WO | 2023233340 | A1 | 12/2023 |
| WO | 2023235815 | A1 | 12/2023 |
| WO | 2023239640 | A1 | 12/2023 |
| WO | 2023239672 | A1 | 12/2023 |
| WO | 2023240152 | A1 | 12/2023 |
| WO | 2023242230 | A1 | 12/2023 |
| WO | 2023242231 | A1 | 12/2023 |
| WO | 2023243111 | A1 | 12/2023 |
| WO | 2023244712 | A1 | 12/2023 |
| WO | 2023249963 | A1 | 12/2023 |
| WO | 2024001184 | A1 | 1/2024 |
| WO | 2024002851 | A1 | 1/2024 |
| WO | 2024003117 | A1 | 1/2024 |
| WO | 2024005054 | A1 | 1/2024 |
| WO | 2024006931 | A1 | 1/2024 |
| WO | 2024007033 | A1 | 1/2024 |
| WO | 2024009084 | A1 | 1/2024 |
| WO | 2024009087 | A1 | 1/2024 |
| WO | 2024013740 | A1 | 1/2024 |
| WO | 2024013745 | A1 | 1/2024 |
| WO | 2024014956 | A1 | 1/2024 |
| WO | 2024015329 | A1 | 1/2024 |
| WO | 2024015365 | A1 | 1/2024 |
| WO | 2024020405 | A1 | 1/2024 |
| WO | 2024023524 | A1 | 2/2024 |
| WO | 2024024720 | A1 | 2/2024 |
| WO | 2024033928 | A1 | 2/2024 |
| WO | 2024038139 | A2 | 2/2024 |
| WO | 2024038281 | A1 | 2/2024 |
| WO | 2024038139 | A3 | 3/2024 |
| WO | 2024059358 | A1 | 3/2024 |
| WO | 2024064910 | A1 | 3/2024 |
| WO | 2023044100 | A8 | 4/2024 |
| WO | 2023086502 | A9 | 4/2024 |
| WO | 2024044689 | A3 | 4/2024 |
| WO | 2024069186 | A1 | 4/2024 |
| WO | 2024071109 | A1 | 4/2024 |
| WO | 2024074916 | A1 | 4/2024 |
| WO | 2024076759 | A1 | 4/2024 |
| WO | 2024081022 | A1 | 4/2024 |
| WO | 2024084082 | A1 | 4/2024 |
| WO | 2024085898 | A1 | 4/2024 |
| WO | 2024086370 | A1 | 4/2024 |
| WO | 2023172696 | A9 | 5/2024 |
| WO | 2024088255 | A1 | 5/2024 |
| WO | 2024097749 | A2 | 5/2024 |
| WO | 2024098059 | A2 | 5/2024 |
| WO | 2024100137 | A1 | 5/2024 |
| WO | 2024100227 | A1 | 5/2024 |
| WO | 2024100228 | A1 | 5/2024 |
| WO | 2024100229 | A1 | 5/2024 |
| WO | 2024100230 | A1 | 5/2024 |
| WO | 2024100401 | A1 | 5/2024 |
| WO | 2024107345 | A1 | 5/2024 |
| WO | 2024107348 | A1 | 5/2024 |
| WO | 2024112636 | A1 | 5/2024 |
| WO | 2023230578 | A9 | 6/2024 |
| WO | 2024084014 | A3 | 6/2024 |
| WO | 2024098059 | A3 | 6/2024 |
| WO | 2024117904 | A1 | 6/2024 |
| WO | 2024118522 | A1 | 6/2024 |
| WO | 2024119096 | A1 | 6/2024 |
| WO | 2024120482 | A1 | 6/2024 |
| WO | 2024123235 | A1 | 6/2024 |
| WO | 2024126712 | A1 | 6/2024 |
| WO | 2024130251 | A1 | 6/2024 |
| WO | 2024130392 | A1 | 6/2024 |
| WO | 2024133961 | A1 | 6/2024 |
| WO | 2024134176 | A1 | 6/2024 |
| WO | 2024134658 | A1 | 6/2024 |
| WO | 2024097749 | A3 | 7/2024 |
| WO | 2024141754 | A1 | 7/2024 |
| WO | 2024141918 | A1 | 7/2024 |
| WO | 2024145619 | A1 | 7/2024 |
| WO | 2024145977 | A1 | 7/2024 |
| WO | 2024148818 | A1 | 7/2024 |
| WO | 2024151321 | A2 | 7/2024 |
| WO | 2024153174 | A1 | 7/2024 |
| WO | 2024133770 | A3 | 8/2024 |
| WO | 2024168400 | A1 | 8/2024 |
| WO | 2024170148 | A1 | 8/2024 |
| WO | 2024170696 | A1 | 8/2024 |
| WO | 2024170702 | A1 | 8/2024 |
| WO | 2024163952 | A3 | 9/2024 |
| WO | 2024181235 | A1 | 9/2024 |
| WO | 2024186212 | A1 | 9/2024 |
| WO | 2024197243 | A1 | 9/2024 |
| WO | 2024080892 | A3 | 10/2024 |
| WO | 2024211655 | A1 | 10/2024 |
| WO | 2024213599 | A1 | 10/2024 |
| WO | 2024228448 | A1 | 11/2024 |
| WO | 2024242255 | A1 | 11/2024 |
| WO | 2024125824 | A3 | 12/2024 |
| WO | 2024151548 | A9 | 12/2024 |
| WO | 2024233991 | A3 | 12/2024 |
| WO | 2024245959 | A1 | 12/2024 |
| WO | 2024251858 | A1 | 12/2024 |
| WO | 2024253585 | A | 12/2024 |
| WO | 2024256710 | A3 | 1/2025 |
| WO | 2024259376 | A3 | 1/2025 |
| WO | 2025003498 | A1 | 1/2025 |
| WO | 2025005124 | A1 | 1/2025 |
| WO | 2025005124 | A5 | 1/2025 |
| WO | 2025012442 | A1 | 1/2025 |
| WO | 2025019473 | A1 | 1/2025 |
| WO | 2025039158 | A1 | 2/2025 |
| WO | 2025040524 | A1 | 2/2025 |
| WO | 2025041145 | A2 | 2/2025 |

(56) References Cited

FOREIGN PATENT DOCUMENTS

| WO | 2025046586 A1 | 3/2025 |
| WO | 2025049891 A1 | 3/2025 |
| WO | 2025050066 A1 | 3/2025 |
| WO | 2025054345 A1 | 3/2025 |
| WO | 2025058807 A1 | 3/2025 |
| WO | 2024226461 A3 | 4/2025 |
| WO | 2025064822 A3 | 4/2025 |
| WO | 2025073942 A1 | 4/2025 |
| WO | 2025078824 A1 | 4/2025 |
| WO | 2025085759 A1 | 4/2025 |
| WO | 2025062138 A3 | 5/2025 |
| WO | 2025089214 A1 | 5/2025 |
| WO | 2025096916 A1 | 5/2025 |
| WO | 2025104748 A1 | 5/2025 |
| WO | 2025109112 A1 | 5/2025 |
| WO | 2025137123 A1 | 6/2025 |
| WO | 2025141177 A1 | 7/2025 |
| WO | 2025141178 A1 | 7/2025 |
| WO | 2025141193 A1 | 7/2025 |
| WO | 2025141211 A1 | 7/2025 |
| WO | 2025144762 A1 | 7/2025 |
| WO | 2025153091 A1 | 7/2025 |
| WO | 2025155925 A1 | 7/2025 |
| WO | 2025160262 A1 | 7/2025 |
| WO | 2025160324 A2 | 7/2025 |
| WO | 2025128722 A3 | 8/2025 |
| WO | 2025137439 A3 | 8/2025 |
| WO | 2025166336 A1 | 8/2025 |
| WO | 2025169198 A1 | 8/2025 |
| WO | 2025172423 A1 | 8/2025 |
| WO | 2025175069 A1 | 8/2025 |
| WO | 2025176874 A1 | 8/2025 |
| WO | 2025181349 A1 | 9/2025 |
| WO | 2025184567 A1 | 9/2025 |
| WO | 2025191562 A1 | 9/2025 |
| WO | 2025196762 A1 | 9/2025 |
| WO | 2025210630 A1 | 10/2025 |
| WO | 2025215354 A1 | 10/2025 |
| WO | 2025224346 A1 | 10/2025 |
| WO | 2025240521 A2 | 11/2025 |
| WO | 2025257695 A1 | 12/2025 |
| WO | 2025259382 A1 | 12/2025 |
| WO | 2026006386 A1 | 1/2026 |

OTHER PUBLICATIONS

Jang, Mi, Ellen Sofie Pete, and Per Bruheim. "The impact of serum-free culture on HEK293 cells: From the establishment of suspension and adherent serum-free adaptation cultures to the investigation of growth and metabolic profiles." Frontiers in Bioengineering and Biotechnology 10 (2022): 964397. 16 pages.

Jerabek, Tobias, et al. "Life at the periphery: what makes CHO cells survival talents." Applied Microbiology and Biotechnology 106.18 (2022): 6157-6167.

Jiang, Susu, Weixi Cai, and Baojun Xu. "Food quality improvement of soy milk made from short-time germinated soybeans." Foods 2.2 (2013): 198-212.

Kamachi, Yasuharu, and Takeshi Omasa. "Development of hyper osmotic resistant CHO host cells for enhanced antibody production." Journal of bioscience and bioengineering 125.4 (2018): 470-478.

Kim, Sung-Hyun, and Gyun-Min Lee. "Differences in optimal pH and temperature for cell growth and antibody production between two Chinese hamster ovary clones derived from the same parental clone." Journal of microbiology and biotechnology 17.5 (2007): 712-720.

Klepetsanis, Pavlos G., and Petros G. Koutsoukos. "Spontaneous precipitation of calcium sulfate at conditions of sustained supersaturation." Journal of colloid and interface science 143.2 (1991): 299-308.

Klöckner, Wolf, et al. "Correlation between mass transfer coefficient k L a and relevant operating parameters in cylindrical disposable shaken bioreactors on a bench-to-pilot scale." Journal of biological engineering 7 (2013): 1-14.

Kohli, Vinny, and Siddhartha Singha. "Protein digestibility of soybean: how processing affects seed structure, protein and non-protein components." Discover Food 4.1 (2024): 7. 16 pages.

Kraus, Barbara, et al. "Avian cell line—Technology for large scale vaccine production." BMC proceedings. vol. 5. BioMed Central, 2011. 3 pages.

Kurano, N., et al. "Growth behavior of Chinese hamster ovary cells in a compact loop bioreactor. 2. Effects of medium components and waste products." Journal of biotechnology 15.1-2 (1990): 113-128.

Lab 1st Bioreactor BR500-Series V.20221208, 11 pages.

Lee, Tsung-Yih, et al. "Inhibitory effect of excessive glucose on its biochemical pathway and the growth of Chinese hamster ovary (CHO) cells." Journal of Carbohydrate Chemistry 34.1 (2015): 1-11.

Leong, Dawn Sow Zong, et al. "Evaluation and use of disaccharides as energy source in protein-free mammalian cell cultures." Scientific reports 7.1 (2017): 45216. 10 pages.

Li, Jincai, et al. "Feeding lactate for CHO cell culture processes: impact on culture metabolism and performance." Biotechnology and bioengineering 109.5 (2012): 1173-1186.

Li, Xiao, et al. "Transcriptomic analysis reveals MAPK signaling pathways affect the autolysis in baker's yeast." FEMS yeast research 20.5 (2020): foaa036. 11 pages.

Lin, Hsiao-Hsien, et al. "High glucose enhances cAMP level and extracellular signal-regulated kinase phosphorylation in Chinese hamster ovary cell: Usage of Br-CAMP in foreign protein β-galactosidase expression." Journal of bioscience and bioengineering 124.1 (2017): 108-114.

Lobo and Borges, Protease activity during 72 hours germination of Soyabean (Glycine max var JS-355), Poster, Feb. 2013. 2 pages.

López-Martínez, Manuel Ignacio, Fidel Toldrá, and Leticia Mora. "Sequential Enzymatic Hydrolysis and Ultrasound Pretreatment of Pork Liver for the Generation of Bioactive and Taste-Related Hydrolyzates." Journal of agricultural and food chemistry 72.28 (2024): 15693-15703.

Lu, Subiao, Xiangming Sun, and Yuanxing Zhang. "Insight into metabolism of CHO cells at low glucose concentration on the basis of the determination of intracellular metabolites." Process biochemistry 40.5 (2005): 1917-1921.

Luo, Jun, et al. "Comparative metabolite analysis to understand lactate metabolism shift in Chinese hamster ovary cell culture process." Biotechnology and bioengineering 109.1 (2012): 146-156.

Major-Godlewska, Marta, and Magdalena Cudak. "Gas Hold-Up in Vessel with Dual Impellers and Different Baffles." Energies 15.22 (2022): 8685. 14 pages.

Majors, Brian S., et al. "E2F-1 overexpression increases viable cell density in batch cultures of Chinese hamster ovary cells." Journal of biotechnology 138.3-4 (2008): 103-106.

Martínez-Edo, Gabriel, et al. "Isothiocyanate-Functionalized mesoporous silica nanoparticles as building blocks for the design of nanovehicles with optimized drug release profile." Nanomaterials 9.9 (2019): 1219. 16 pages.

Martínez, Verónica S.; Dietmair, Stefanie; Quek, Lake-Ee; Hodson, Mark P.; Gray, Peter; Nielsen, Lars K. . (2013). Flux balance analysis of CHO cells before and after a metabolic switch from lactate production to consumption. Biotechnology and Bioengineering, 110(2), 660-666. doi: 10.1002/bit.24728.

Matsuo, Taisuke, et al. "The effects of vitamin B6 compounds on cell proliferation and melanogenesis in B16F10 melanoma cells." Oncology Letters 15.4 (2018): 5181-5184.

Mengke Yuan; Jingcheng Zhang; Yuanpeng Gao;Zikun Yuan;Zhenliang Zhu;Yongke Wei;Teng Wu;Jing Han;Yong Zhang;. (2021). HMEJ-based safe-harbor genome editing enables efficient generation of cattle with increased resistance to tuberculosis . Journal of Biological Chemistry, doi:10.1016/j.jbc.2021.100497. 12 pages.

Merten, O-W., S. Petres, and E. Couve. "A simple serum-free freezing medium for serum-free cultured cells." Biologicals 23.2 (1995): 185-189.

Michele Sadler, "Myco-protein—a new food", BNF Nutrition Bulletin, Sep. 1990. 11 pages.

(56) References Cited

OTHER PUBLICATIONS

Morrison, Carly et al., Improvement of growth rates through nucleoside media supplementation of CHO clones; Cytotechnology, 10.1007/s10616-019-00319-0(; May 21, 2019. 10 pages.

Mosser, Mathilde, et al. "Combination of yeast hydrolysates to improve CHO cell growth and IgG production." Cytotechnology 65.4 (2013): 629-641.

Mulukutla, Bhanu Chandra, et al. "Identification and control of novel growth inhibitors in fed-batch cultures of Chinese hamster ovary cells." Biotechnology and Bioengineering 114.8 (2017): 1779-1790.

Nayar, Gautam. Oxygen transport in animal cell biogreactors with vibrating-plate aerators. Diss. Massachusetts Institute of Technology, 1995. 270 pages.

Njoroge, B. NK, and Slade Gilbert Mwamachi. "Ammonia removal from an aqueous solution by the use of a natural zeolite." Journal of Environmental Engineering and Science 3.2 (2004): 147-154.

Nolan, Ryan P., and Kyongbum Lee. "Dynamic model of CHO cell metabolism." Metabolic engineering 13.1 (2011): 108-124.

Pan, Xiao, et al. "Metabolic characterization of a CHO cell size increase phase in fed-batch cultures." Applied microbiology and biotechnology 101 (2017): 8101-8113.

Papapetrou, Eirini P., and Axel Schambach. "Gene insertion into genomic safe harbors for human gene therapy." Molecular Therapy 24.4 (2016): 678-684.

Peksel, Begüm, et al. "Mild heat induces a distinct "eustress" response in Chinese Hamster Ovary cells but does not induce heat shock protein synthesis." Scientific reports 7.1 (2017): 15643. 12 pages.

Pennycook, Betheney R., et al. "E2F-dependent transcription determines replication capacity and S phase length." Nature communications 11.1 (2020): 3503. 10 pages.

Pereira, Sara, Helene Faustrup Kildegaard, and Mikael Rørdam Andersen. "Impact of CHO metabolism on cell growth and protein production: An overview of toxic and inhibiting metabolites and nutrients." Biotechnology Journal 13.3 (2018): 1700499. 40 pages.

Perillo, Matteo, et al. "The spontaneous immortalization probability of mammalian cell culture strains, as their proliferative capacity, correlates with species body mass, not longevity." biomedical journal 46.3 (2023): 100596. Supplementary Material. 1 page.

Petry, Florian, and Denise Salzig. "Large-scale production of size-adjusted β-cell spheroids in a fully controlled stirred-tank reactor." Processes 10.5 (2022): 861. 22 pages.

Podpora, Bartłomiej, et al. "Spent brewer's yeast extracts as a new component of functional food." Czech Journal of Food Sciences 34.6 (2016): 554. 10 pages.

Polacco, Joseph C., and Evelyn A. Havir. "Comparisons of soybean urease isolated from seed and tissue culture." Journal of Biological Chemistry 254.5 (1979): 1707-1715.

Prabhu, Anuja, and Mugdha Gadgil. "Nickel and cobalt affect galactosylation of recombinant IgG expressed in CHO cells." Biometals 32 (2019): 11-19.

Qian, Yueming; Sowa, Steven W.; Aron, Kathryn L.; Xu, Ping; Langsdorf, Erik; Warrack, Bethanne; Aranibar, Nelly; Tremml, Gabi; Xu, Jianlin; McVey, Duncan; Reily, Michael; Khetan, Anurag; Borys, Michael C.; Li, Zheng Jian. (2020). New insights into genetic instability of an industrial CHO cell line by orthogonal omics. Biochemical Engineering Journal, 107799-. doi: 10.1016/j.bej.2020.107799. 38 pages.

Qin, Jane Yuxia; Zhang, Li; Clift, Kayla L.; Hulur, Imge; Xiang, Andy Peng; Ren, Bing-Zhong; Lahn, Bruce T.; Hansen, Immo A. . (2010). Systematic Comparison of Constitutive Promoters and the Doxycycline-Inducible Promoter. PLoS ONE, 5(5), e10611-. doi:10.1371/journal.pone.0010611.

Rafacz-Livingston, K. A., C. M. Parsons, and R. A. Jungk. "The effects of various organic acids on phytate phosphorus utilization in chicks." Poultry Science 84.9 (2005): 1356-1362.

Rao, Potu N., and Joseph Engelberg. "HeLa cells: effects of temperature on the life cycle." Science 148.3673 (1965): 1092-1094.

Zhang, Lili, et al. "An oncogenic role for the phosphorylated h-subunit of human translation initiation factor eIF3." Journal of Biological Chemistry 283.35 (2008): 24047-24060.

Zhao, Xinghui, et al. "Overexpression of survivin and cyclin D1 in CHO cells confers apoptosis resistance and enhances growth in serum-free suspension culture." Biotechnology letters 33 (2011): 1293-1300.

Zhu, Marie M., et al. "Effects of elevated pCO2 and osmolality on growth of CHO cells and production of antibody-fusion protein B1: A case study." Biotechnology progress 21.1 (2005): 70-77.

Rees, Byron, et al. "Characterization and performance of the Allegro™ STR 200 single-use stirred tank bioreactor." BMC Proceedings. vol. 9. No. Suppl 9. London: BioMed Central, 2015. 2 pages.

Renner, Wolfgang A., et al. "Recombinant cyclin E expression activates proliferation and obviates surface attachment of Chinese hamster ovary (CHO) cells in protein-free medium." Biotechnology and bioengineering 47.4 (1995): 476-482.

Roca, Berta Capella, et al. "An arginase-based system for selection of transfected CHO cells without the use of toxic chemicals." Journal of Biological Chemistry 294.49 (2019): 18756-18768.

Rochovansky, Olga. "Pyrimidine biosynthesis in the chick." Archives of Biochemistry and Biophysics 138.2 (1970): 574-581.

Romanova, Nadiya, et al. "Hyperosmolality in CHO cell culture: effects on the proteome." Applied microbiology and biotechnology 106.7 (2022): 2569-2586.

Sasaki, Masahiro, et al. "Development of a novel serum-free freezing medium for mammalian cells using the silk protein sericin." Biotechnology and applied biochemistry 42.2 (2005): 183-188.

Sciola and Yavorsky, Mycoplasm removal, Millipore ED, May 6, 2006. 3 pages.

Shang, Menglin, et al. "Investigating the influence of physiologically relevant hydrostatic pressure on CHO cell batch culture." Scientific Reports 11.1 (2021): 162. 9 pages.

Shin, Woo-Shik, et al. "Application of scale-up criterion of constant oxygen mass transfer coefficient (kLa) for production of itaconic acid in a 50 L pilot-scale fermentor by fungal cells of Aspergillus terreus." J. Microbiol. Biotechnol. 23.10 (2013): 1445-1453.

Shrestha, Dewan, et al. "Genomics and epigenetics guided identification of tissue-specific genomic safe harbors." Genome biology 23.1 (2022): 199.

Sieck, Jochen B., et al. "Adaptation for survival: Phenotype and transcriptome response of CHO cells to elevated stress induced by agitation and sparging." Journal of biotechnology 189 (2014): 94-103.

Sigma Aldrich, Electrical Schematic for P&D Pilot 130L, Nov. 12, 2008.23 pages.

Sigma Cell Freezing Medium, Serum-Free (1X) product information. Date unknown. 1 page.

Sikdar, Subhas K., and Sudhir B. Sawant. "Ammonia removal from mammalian cell culture medium by ion-exchange membranes." Separation science and technology 29.12 (1994): 1579-1591.

Šrom, Ondřej et al., Investigation of poloxamer cell protective ability via shear sensitive aggregates in stirred aerated bioreactor, Biochemical engineering Journal, 10.1016/j.bej.2022.108549; Jul. 21, 2022. 7 pages.

Šrom, Ondřej et al., et al., Characterization of hydrodynamic stress in ambr250® bioreactor system and its impact on mammalian cell culture, Biochemical Engineering Journal, 10.1016/j.bej.2021.108240; Oct. 19, 2021. 9 pages.

Stout, Andrew J., et al. "Engineered autocrine signaling eliminates muscle cell FGF2 requirements for cultured meat production." Cell Reports Sustainability 1.1 (2024). 9 pages.

Stout, Andrew J., et al. "Immortalized bovine satellite cells for cultured meat applications." ACS synthetic biology 12.5 (2023): 1567-1573.

Surve, Tanaya, and Mugdha Gadgil. "Manganese increases high mannose glycoform on monoclonal antibody expressed in CHO when glucose is absent or limiting: Implications for use of alternate sugars." Biotechnology Progress 31.2 (2015): 460-467.

Suzuki, Takahiro, Takeshi Sato, and Minoru Kominami. "A dense cell retention culture system using stirred ceramic membrane reactor." Biotechnology and bioengineering 44.10 (1994): 1186-1192.

(56) References Cited

OTHER PUBLICATIONS

Takagi, Yasuhiro, et al. "The enhancement of antibody concentration and achievement of high cell density CHO cell cultivation by adding nucleoside." Cytotechnology 69 (2017): 511-521.

Takalloo, Zeinab; Nikkhah, Mohsen; Nemati, Robabeh; Jalilian, Nezam; Sajedi, Reza H. . (2020). Autolysis, plasmolysis and enzymatic hydrolysis of baker's yeast (Saccharomyces cerevisiae): a comparative study. World Journal of Microbiology and Biotechnology, 36(5), 68-. doi: 10.1007/s11274-020-02840-3. 14 pages.

Takuma, Shinya, Chikashi Hirashima, and James M. Piret. "Effects of glucose and CO2 concentrations on CHO cell physiology." Animal Cell Technology: Basic & Applied Aspects: Proceedings of the Fifteenth Annual Meeting of the Japanese Association for Animal Cell Technology (JAACT), Fuchu, Japan, Nov. 11-15, 2002. Dordrecht: Springer Netherlands, 2003. 5 pages.

Tamaru, Shizuka, et al. "Dietary soybean peptides containing a low-molecular fraction can lower serum and liver triglyceride levels in rats." Journal of nutritional science and vitaminology 60.6 (2014): 436-442.

Tang, Ning, and Leif H. Skibsted. "Zinc bioavailability from phytate-rich foods and zinc supplements. Modeling the effects of food components with oxygen, nitrogen, and sulfur donor ligands." Journal of agricultural and food chemistry 65.39 (2017): 8727-8743.

Tao, Fangfang, et al. "Simulation study on gas holdup of large and small bubbles in a high pressure gas-liquid bubble column." Processes 7.9 (2019): 594. 16 pages.

Thompson, Larry H., and Raymond M. Baker. "Isolation of mutants of cultured mammalian cells." Methods in cell biology. vol. 6. Academic Press, 1973. 209-281.

Tihanyi, Borbála, and László Nyitray. "Recent advances in CHO cell line development for recombinant protein production." Drug Discovery Today: Technologies 38 (2020): 25-34.

Tomita, Kazunori. "How long does telomerase extend telomeres? Regulation of telomerase release and telomere length homeostasis." Current genetics 64.6 (2018): 1177-1181.

Torres, Mauro, et al. "Long term culture promotes changes to growth, gene expression, and metabolism in CHO cells that are independent of production stability." Biotechnology and Bioengineering 120.9 (2023): 2389-2402.

Vagadia, Brinda Harish, Sai Kranthi Vanga, and Vijaya Raghavan. "Inactivation methods of soybean trypsin inhibitor—A review." Trends in Food Science & Technology 64 (2017): 115-125.

Van Driessche, Alexander ES, T. M. Stawski, and M. Kellermeier. "Calcium sulfate precipitation pathways in natural and engineered environments." Chemical Geology 530 (2019): 119274. 29 pages.

Walls, Peter LL, et al. "Quantifying the potential for bursting bubbles to damage suspended cells." Scientific reports 7.1 (2017): 15102. 9 pages.

Watson, Pavinee E., et al. "Drivers of palatability for cats and dogs—What it means for pet food development." Animals 13.7 (2023): 1134. 22 pages.

Weidner, Tobias; Druzinec, Damir; Mühlmann, Martina; Buchholz, Rainer; Czermak, Peter . (2017). The components of shear stress affecting insect cells used with the baculovirus expression vector system. Zeitschrift für Naturforschung C doi: 10.1515/znc-2017-0066. 11 pages.

Weiss, Christine H., Corinna Merkel, and Aline Zimmer. "Impact of iron raw materials and their impurities on CHO metabolism and recombinant protein product quality." Biotechnology Progress 37.4 (2021): e3148. 14 pages.

Wlaschin, Katie F., and Wei-Shou Hu. "Engineering cell metabolism for high-density cell culture via manipulation of sugar transport." Journal of biotechnology 131.2 (2007): 168-176.

Wurm, Florian M., and Maria João Wurm. "Cloning of CHO cells, productivity and genetic stability—a discussion." Processes 5.2 (2017): 20. 13 pages.

Wurm, Maria J., and Florian M. Wurm. "Naming CHO cells for bio-manufacturing: Genome plasticity and variant phenotypes of cell populations in bioreactors question the relevance of old names." Biotechnology Journal 16.7 (2021): 2100165. 24 pages.

Xiao, Shang, et al. "Continuous feeding reduces the generation of metabolic byproducts and increases antibodies expression in Chinese hamster ovary-K1 cells." Life 11.9 (2021): 945. 12 pages.

Xu, Jianlin, et al. "Systematic development of temperature shift strategies for Chinese hamster ovary cells based on short duration cultures and kinetic modeling." MAbs. vol. 11. No. 1. Taylor & Francis, 2019. 15 pages.

Xu, Sen, et al. "A practical approach in bioreactor scale-up and process transfer using a combination of constant P/V and vvm as the criterion." Biotechnology Progress 33.4 (2017): 1146-1159.

Xu, Sen, et al. "Impact of Pluronic® F68 on hollow fiber filter-based perfusion culture performance." Bioprocess and Biosystems Engineering 40 (2017): 1317-1326.

Yamanaka, Kumiko, et al. "Development of serum-free and grain-derived-nutrient-free medium using microalga-derived nutrients and mammalian cell-secreted growth factors for sustainable cultured meat production." Scientific Reports 13.1 (2023): 498. 13 pages.

Yamano-Adachi, Noriko, et al. "Establishment of fast-growing serum-free immortalised cells from Chinese hamster lung tissues for biopharmaceutical production." Scientific Reports 10.1 (2020): 17612. 12 pages.

Yehia, N. S., et al. "Effects of some parameters affecting the crystallization rate of calcium sulfate dihydrate in sodium chloride solution." Journal of American Science 7.6 (2011): 635-644.

Yuan, Mengke, et al. "HMEJ-based safe-harbor genome editing enables efficient generation of cattle with increased resistance to tuberculosis." Journal of Biological Chemistry 296 (2021). 10 pages.

Yuk, Inn H., et al. "Effects of copper on CHO cells: cellular requirements and product quality considerations." Biotechnology Progress 31.1 (2015): 226-238.

Zagari, Francesca, et al. "Lactate metabolism shift in CHO cell culture: the role of mitochondrial oxidative activity." New biotechnology 30.2 (2013): 238-245.

Zhang, Li-xiang, et al. "Responses of CHO-DHFR cells to ratio of asparagine to glutamine in feed media: cell growth, antibody production, metabolic waste, glutamate, and energy metabolism." Bioresources and Bioprocessing 3 (2016): 1-12.

Agustini, Rudiana, and Nuniek Herdyastuti. "The Study of Amylase's Reaction Kinetics From Soybean Sprouts (Glycine max L.) in Hydrolyzing Starch." International Joint Conference on Science and Engineering (IJCSE 2020). Atlantis Press, 2020. 6 pages.

Akita, Kiyomi, and Fumitake Yoshida. "Bubble size, interfacial area, and liquid-phase mass transfer coefficient in bubble columns." Industrial & Engineering Chemistry Process Design and Development 13.1 (1974): 84-91.

Akpapunam, M. A., S. O. Igbedioh, and I. Aremo. "Effect of malting time on chemical composition and functional properties of soybean and bambara groundnut flours." International journal of food sciences and nutrition 47.1 (1996): 27-33.

Alam, Mohd Nazrul Hisham Zainal, and Firdausi Razali. "Scaleup of Stirred and Aerated BioengineeringTM Bioreactor Based on Constant Mass Transfer Coefficient." Jurnal Teknologi (2005): 95â-110.

Alhuthali, Sakhr, Pavlos Kotidis, and Cleo Kontoravdi. "Osmolality effects on CHO cell growth, cell vol. antibody productivity and glycosylation." International journal of molecular sciences 22.7 (2021): 3290. 19 pages.

Ali, Haider, Sofia Zhu, and Jannike Solsvik. "Effects of geometric parameters on volumetric mass transfer coefficient of non-Newtonian fluids in stirred tanks." International Journal of Chemical Reactor Engineering 20.7 (2022): 697-711.

Alkhalidi, A., R. Amano, and M. Khawaja. "Estimation model of KLa constant using bubble release rate and bubble size." Sch. J. Eng. Tech. 7.2 (2019): 33-40.

Altamirano, Claudia, et al. "Considerations on the lactate consumption by CHO cells in the presence of galactose." Journal of biotechnology 125.4 (2006): 547-556.

Altamirano, Claudia, et al. "Strategies for fed-batch cultivation of t-PA producing CHO cells: substitution of glucose and glutamine and rational design of culture medium." Journal of biotechnology 110.2 (2004): 171-179.

(56) References Cited

OTHER PUBLICATIONS

Application note: Batch cultivation of CHO-K1 cells in Labfors 5 Cell, Prof. Dr.-Ing. habil. Ralf Pörtner, Hamburg University of Technology, Institute of Bioprocess and Biosystems Engineering, Hamburg, Germany www.infors-ht. com, 2 pages.

Application note: Batch culture of CHO cells in the Multifors Cell, ZHAW, IBT, CH-Wädenswil, and INFORS HT, CH-Bottmingen, www.infors-ht.com, 2 pages.

ATCC hTERT-immortalized Cell Culture Guide, www.atcc.org, 2022, 32 pages.

Aznauryan, Erik, et al. "Discovery and validation of human genomic safe harbor sites for gene and cell therapies." Cell Reports Methods 2.1 (2022). 10.1016/j.crmeth.2021.100154. 20 pages.

Barlat, I., et al. "Loss of the G1-S control of cyclin A expression during tumoral progression of Chinese hamster lung fibroblasts." Cell Growth & Differentiation: The Molecular Biology Journal of the American Association for Cancer Research 4.2 (1993): 105-113.

Beiranvand, Fateme, Seyed Hesam Najibi, and Bahram Hashemi Shahraki. "Experimental measurement of equilibrium surface tension of an aqueous solution of polyethylene glycol and a surfactant." Iranian Journal of Oil and Gas Science and Technology 9.3 (2020): 26-43.

Białkowska, Kamila, et al. "Spheroids as a type of three-dimensional cell cultures—examples of methods of preparation and the most important application." International journal of molecular sciences 21.17 (2020): 6225. 17 pages.

Branda, Catherine S., and Susan M. Dymecki. "Talking about a revolution: The impact of site-specific recombinases on genetic analyses in mice." Developmental cell 6.1 (2004): 7-28.

Brose, Daniel J., and Paul Van Eikeren. "A membrane-based method for removal of toxic ammonia from mammalian-cell culture." Applied biochemistry and biotechnology 24 (1990): 457-468.

Buffo, M. M., et al. "Influence of dual-impeller type and configuration on oxygen transfer, power consumption, and shear rate in a stirred tank bioreactor." Biochemical Engineering Journal 114 (2016): 130-139.

Carina Villacrés; Venkata S. Tayi;Michael Butler;. (2021). Strategic feeding of NS0 and CHO cell cultures to control glycan profiles and immunogenic epitopes of monoclonal antibodies. Journal of Biotechnology, doi: 10.1016/j.jbiotec.2021.04.005. 14 pages.

Castel, Christophe, Roda Bounaceur, and Eric Favre. "Membrane processes for direct carbon dioxide capture from air: possibilities and limitations." Frontiers in Chemical Engineering 3 (2021): 668867. 15 pages.

Chalmers, Jeffrey J. "Cells and bubbles in sparged bioreactors." Cell Culture Engineering IV: Improvements of Human Health (1995): 311-320.

Chen, Zhao-Lie, et al. "Temperature shift as a process optimization step for the production of pro-urokinase by a recombinant Chinese hamster ovary cell line in high-density perfusion culture." Journal of bioscience and bioengineering 97.4 (2004): 239-243.

Chung, Myung-Il, et al. "Reduction of ammonia accumulation and improvement of cell viability by expression of urea cycle enzymes in Chinese hamster ovary cells." Journal of microbiology and biotechnology 13.2 (2003): 217-224.

Chusainow, Janet, et al. "A study of monoclonal antibody-producing CHO cell lines: What makes a stable high producer?." Biotechnology and bioengineering 102.4 (2009): 1182-1196.

Clincke, Marie-Francoise, et al. "Very high density of CHO cells in perfusion by ATF or TFF in WAVE bioreactor™. Part I. Effect of the cell density on the process." Biotechnology progress 29.3 (2013): 754-767.

Conway, John, Hélène Gaudreau, and Claude P. Champagne. "The effect of the addition of proteases and glucanases during yeast autolysis on the production and properties of yeast extracts." Canadian journal of microbiology 47.1 (2001): 18-24.

Cudak, Magdalena. "The effect of vessel scale on gas hold-up in gas-liquid systems." Chemical and Process Engineering 41.4 (2020): 241-256.

Cunningham, John T., et al. "Protein and nucleotide biosynthesis are coupled by a single rate-limiting enzyme, PRPS2, to drive cancer." Cell 157.5 (2014): 1088-1103.

Curriden, Scott, and Ellis Englesberg. "Inhibition of growth of proline-requiring Chinese hamster ovary cells (CHO-K1) resulting from antagonism by a system amino acids." Journal of Cellular Physiology 106.2 (1981): 245-252.

Darrin Kuystermans; Mohamed Al-Rubeai. (2009). cMyc increases cell number through uncoupling of cell division from cell size in CHO cells. , 9(1), 76-0. doi: 10.1186/1472-6750-9-76.

Davies, Sarah L., et al. "Functional heterogeneity and heritability in CHO cell populations." Biotechnology and Bioengineering 110.1 (2013): 260-274.

De Zawadzki, Andressa et al., Increasing calcium phosphate aqueous solubility and spontaneous supersaturation combining citrate and gluconate with perspectives for functional foods, Journal of Food Chemistry. 10.1016/j.foodchem.2021.131701; Nov. 30, 2021. 9 pages.

Derouazi, Madiha, et al. "Genetic characterization of CHO production host DG44 and derivative recombinant cell lines." Biochemical and biophysical research communications 340.4 (2006): 1069-1077.

DeZengotita, Vivian M., et al. "Selected amino acids protect hybridoma and CHO cells from elevated carbon dioxide and osmolality." Biotechnology and bioengineering 78.7 (2002): 741-752.

DeZengotita, Vivian M., Roy Kimura, and William M. Miller. "Effects of CO 2 and osmolality on hybridoma cells: growth, metabolism and monoclonal antibody production." Cell Culture Engineering VI (1998): 213-227.

Dong, Q., & Saneoka, H. (2020). Physiological Characteristics, Phytase Activity, and Mineral Bioavailability of a Low-Phytate Soybean Line during Germination. Plant Foods for Human Nutrition, 75(3), 383-389. doi: 10.1007/s11130-020-00827-x.

Fan, Yuzhou, et al. "Amino acid and glucose metabolism in fed-batch CHO cell culture affects antibody production and glycosylation." Biotechnology and bioengineering 112.3 (2015): 521-535.

Faust, Christine, et al. "Impact of lipopolysaccharides on cultivation and recombinant protein expression in human embryonal kidney (HEK-293) cells." Engineering in Life Sciences 21.11 (2021): 778-785.

Folmsbee, "An explanation and evaluation of sterile connector soiling tests" PALL technical position paper, Oct. 19, 2021, 6 pages.

Fu, Bo, et al. "Competition between chemolithotrophic acetogenesis and hydrogenotrophic methanogenesis for exogenous H2/CO2 in anaerobically digested sludge: impact of temperature." Frontiers in Microbiology 10 (2019): 2418. 9 pages.

Gao, Yang, et al. "Constitutive activation of transforming growth factor Beta receptor 1 in the mouse uterus impairs uterine morphology and function." Biology of reproduction 92.2 (2015): 34-1.

Grein, Tanja A., et al. "Aeration and shear stress are critical process parameters for the production of oncolytic measles virus." Frontiers in bioengineering and biotechnology 7 (2019): 78. 11 pages.

Ha, Thanh Toan, Thi Phuong Lien Duong, and Thi Bich Tram Phan. "Effect of germination on antioxidant capacity and nutritional quality of soybean seeds (Glycinemax (L.) merr.)." CTU Journal of Innovation and Sustainable Development 06 (2017): 93-101.

Harsini and Swartz, Trends in cultivated meat scale-up and bioprocessing; Good Food Institute, Mar. 20, 2024. 42 pages.

Hoeijmakers, Jan HJ, Hanny Odijk, and Andries Westerveld. "Differences between rodent and human cell lines in the amount of integrated DNA after transfection." Experimental cell research 169.1 (1987): 111-119.

Holmlund, A. C., et al. "Growth and metabolism of recombinant CHO cell-lines in serum free medium containing derivatives of glutamine." Animal Cell Technology. Butterworth-Heinemann, 1992. 176-179.

Huang, Zhuangrong, et al. "CHO cell productivity improvement by genome-scale modeling and pathway analysis: Application to feed supplements." Biochemical Engineering Journal 160 (2020): 107638. 34 pages.

Huang, Zhuangrong, et al. "Insights into the impact of rosmarinic acid on CHO cell culture improvement through transcriptomics analysis." Processes 10.3 (2022): 533. 12 pages.

(56)            References Cited

OTHER PUBLICATIONS

Huntley, Nichole F., and John F. Patience. "Xylose: absorption, fermentation, and post-absorptive metabolism in the pig." Journal of Animal Science and Biotechnology 9 (2018): 1-9.

Andreassen et al., (2020) Screening of by-products from the food industry as growth promoting agents in serum-free media for skeletal muscle growth. Food Funct, 11: pp. 2477-2488 (Year: 2020).

Deionized Water Conductivity. Datasheet [online]. Alpha Measurement Systems, 2024 [retrieved on Aug. 5, 2025] Retrieved from the Internet: < https://alpha-measure.com/deionized-water-conductivity/> (Year: 2024) (pp. 1-5).

DMEM Formulation. Datasheet [online]. Sigma, 2025 [retrieved on Aug. 5, 2025]. Retrieved from the Internet: (Year: 2025) (pp. 1-13).

Jiang et al. "Strategies for Sustainable Substitution of Livestock Meat" Foods Sep. 3, 2020 (Year: 2020) (pp. 1-20).

Mattick et al., (2015) Anticipatory life cycle analysis of in vitro biomass cultivation for cultured meat production in the United States. Environ. Sci. Technol., 49: pp. 11941-11949.

R. Ian Freshney, Scale-up and Automation. In: Culture of Animal Cell: A Manual of Basic Technique and Specialized Applications (Hoboken, NJ, John Wiley & Sons, Inc., 2010), pp. 497-515. QH585.2.F74 2010 (Year: 2010).

Romero et al. "Systems biology and metabolic modeling for cultivated meat: A promising approach for cell culture media optimization and cost reduction" Comprehensive Reviews in Food Science and Food Safety vol. Jul. 4, 2023 (Year: 2023) (pp. 1-2).

Sommeregger et al., "Powerful expression in Chinese Hamster Ovary cells using bacterial artificial chromosomes: Parameters influencing productivity" 7 (Suppl. 6) BMC Proceedings P25, 1-2 (Year: 2013).

Obaidi et al., "The role of protein hydrolysates in prolonging viability and enhancing antibody production of CHO cells" 105 Applied Microbiology and Biotechnology 3115-3129 (Year: 2021).

Khan et al., "Akt Kinase Pohsphorylation of Inositol 1,4,5-Triphosphate Receptors" 281(6) The Journal of Biological Chamistry 3731-3737 (Year: 2006).

Crea et al., "Over-expression of hTERT in CHO K1 results in decreased apoptosis and reduced serum dependency" 121 Journal of Biotechnology 109-123 (Year: 2006).

Kook, Moo-Chang, et al. "*Bacillus subtilis* fermentation for enhancement of feed nutritive value of soybean meal." Journal of applied biological chemistry 57.2 (2014): 183-188.

United States Environmental Protection Agency, "Water: Monitoring & Assessment", Mar. 6, 2012. (Year: 2012) 2 pages.

R. Ian Freshney, "Preparation and Sterilization", "Scale-up and Automation." In: Culture of Animal Cell: A Manual of Basic Technique and Specialized Applications. (Hoboken, NJ, John Wiley & Sons, Inc., 2010), pp. 133-162, 497-515. QH585.2.F74 2010 (Year: 2010).

Pasitka, L., Cohen, M., Regenbaum, S et al. Spontaneous immortalization of bovine fibroblasts following long-term expansion offers a non-transformed cell source for cultivated beef. Nat Food 6, 1079-1094 (2025). https://doi.org/10.1038/s43016-025-01255-3.

Barakova et al., "The efficiency of phytase and impact-disintegrator-activator processing ofacid in soy protein hydrolysates", Processes and Food Production Equipment, 2023, No. 3, pp. 3-10. DOI: 10.17586/2310-1164-2023-16-3-3-10.

\* cited by examiner

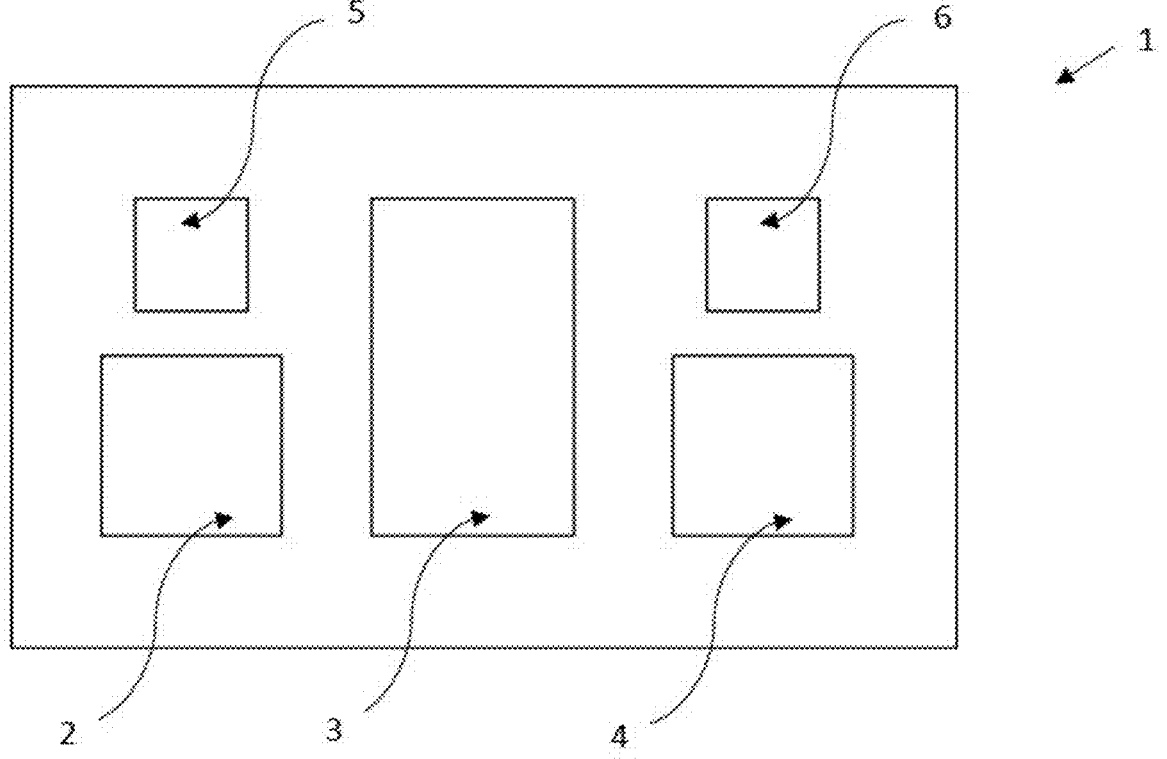

CULTURE MEDIA BASED ON PROTEIN HYDROLYSATE AND A PROCESS FOR PREPARING THEREOF

CROSS-REFERENCE TO RELATED APPLICATIONS

This application is a continuation of PCT Patent Application No. PCT/IB2024/053805 filed Apr. 18, 2024, which claims priority to U.S. Provisional Patent Application No. 63/497,051 filed Apr. 19, 2023, each of which are incorporated by reference herein in their entireties.

FIELD OF THE INVENTION

The invention relates to a culture media based on a protein hydrolysate suitable for cell cultivation and a process for preparation thereof. The culture media according to the invention may be used, for example, for cell cultivation for preparing a food product comprising a cell biomass for animal or human nutrition.

BACKGROUND OF THE INVENTION

Mammalian cells are composed of a variety of chemical compounds. A major component of cell biomass is protein, which usually makes up 60% to 80% of dry mass of cells. Proteins are long polymers of amino acids. There are 20 proteinogenic amino acids, 9 of which are dietary essential in mammals, meaning that they cannot be synthesized by the organism and must be sourced from food, or, in the case of cultivated cells, from the culture media. Additionally, some amino acids may be considered "semi-essential" or conditionally essential, because they can be only synthesized from a particular essential amino acid, or their synthesis tends to be very slow under some conditions.

Cell line-specific spontaneous mutations or deliberate modifications may cause cells to become unable to synthesize one or more amino acids, and therefore said amino acids need to be provided in the culture media (auxotrophy). The cells may, through spontaneous mutations or deliberate modification, gain or regain the ability to synthesize a particular amino acid. Even non-essential amino acids, which the cells are able to synthesize, may be important to the cultivation process, as the cells may also exhibit improved growth or metabolic characteristics when provided with some non-essential amino acids. Cells may also be able to utilize certain other nitrogen sources, notably ammonia, to synthesize non-essential amino acids.

Generally, amino acids mainly serve as building blocks for protein synthesis, and thus are consumed in media in proportion to the amino acid composition of the cellular protein. However, some amino acids may be consumed by the cells at a higher rate than would correspond to their abundance in cellular protein, as they may be used in energetic metabolism, nucleic acid synthesis and other such processes. To provide cells in culture with adequate amino acids for protein synthesis, commonly used culture media formulations contain individual amino acids at different ratios of concentration. These amino acids are usually produced by fermentation processes with microorganisms engineered to produce a specific amino acid. Some amino acids can also be synthesized chemically, but this is generally more expensive than microbial production. However, while microbial production works well for the needs of cell cultivation in research and therapeutic protein production applications, it is generally too expensive for cultivated meat production.

Therefore, there is a need for culture media with an alternative and more economically advantageous source of amino acids. This culture media should be suitable for cell cultivation and economically favorable.

BRIEF SUMMARY OF THE INVENTION

The disadvantages of the solutions according to state of the art are solved by the present invention that provides culture media suitable for cell cultivation and the processes for preparation thereof.

The culture media may be prepared by dissolving media components in water or a suitable aqueous buffer. The complete medium may be prepared outside of the cell cultivation device, formed for example by a bioreactor, and subsequently introduced to the cultivation device; alternatively, constituent solutions of one or more components may be prepared outside of the cultivation device and introduced separately to the cultivation device; alternatively, the individual components or mixes of components may be introduced to and dissolved directly in the cultivation device; alternatively, a combination of the aforementioned methods may be used.

Sterilization of the culture media is crucial to prevent the contamination of the cultivation device, formed for example by a bioreactor, by undesirable microorganisms. The culture medium may be sterilized after being introduced into the cultivation device; alternatively, the complete culture medium, constituent solutions of one or more components, individual components or their mixes may be sterilized before being introduced into the cultivation device; alternatively, a combination of the aforementioned methods may be used.

The culture media according to the present invention may comprise protein hydrolysate as a source of amino acids. The protein hydrolysate may serve as a source of all amino acids in culture media according to the invention for the purpose of cell cultivation, or some amino acids may be supplied to the media separately. The advantageous process of protein hydrolysis into shorter peptide chains and/or single amino acids is also provided by the present invention.

BRIEF DESCRIPTION OF THE SEVERAL VIEWS OF THE DRAWINGS

FIG. 1 depicts the cultivation system according to the invention.

DETAILED DESCRIPTION OF THE INVENTION

The disadvantages of the solutions according to state of the art are solved by the present invention that provides culture media suitable for cell cultivation, and the processes for preparation thereof.

The culture media according to the invention may be used, for example, for cell cultivation for the purpose of using the cell biomass for animal or human nutrition. The culture media according to the invention may be used for cultivated meat production.

The cell types used for cultivation processes in the culture media according to the present invention may comprise many types of non-human metazoan cells, for example, stem cells comprising embryonic stem cells (ESCs) and other cell types derived from blastocyst or other early-stage embryos, muscle stem cells such as myosatellite cells, mesenchymal stem cells or cells derived from the bone marrow, fat tissue, subcutaneous tissue or other tissues, or cells where the stemness character is induced or established afterwards such as induced pluripotent stem cells (iPSCs). Other used cell types may be, for example, myoblasts, myocytes, fibroblasts, fibro-adipogenic progenitors, preadipocytes, adipocytes, epithelial cells, cartilage cells and tendon-derived cells such as chondroblasts and chondrocytes, macrophages, keratinocytes, hepatocytes, testicular cells, Sertoli cells, or any other appropriate cells.

The cell lines used for cultivation processes in the culture media according to the invention may include, for example, Chinese hamster ovary (CHO) cells, for example CHO-K1 or CHO-DG44, C2C12, Madin-Darby bovine kidney cells (MDBKs), Madin-Darby canine kidney (MDCK) cells, UMNSAH/DF-1, or any other appropriate cell lines.

The cells used for cultivation processes in the culture media according to the invention may be any appropriate non-human metazoan cells. The cells for cultivation may be non-human vertebrate cells. The cells may be, for example, bovine, porcine, fish (piscine), game (cervine), avian, rodent (cricetine, murine), equine or any other appropriate cells. The cells for cultivation may be selected, without limitation, from at least one of the following animals: cattle (*Bos taurus*), chicken (*Gallus domesticus*), domestic pig (*Sus domesticus*), house cricket (*Acheta domesticus*), garden snail (*Helix pomatia*), common carp (*Cyprinus carpio*), horse (*Equus ferus*), edible crab (*Cancer pagurus*), marsh frog (*Pelophylax ridibundus*), common *octopus* (*Octopus vulgaris*), gilt-head bream (*Sparus aurata*), roe deer (*Capreolus capreolus*), common sea urchin (*Echinus esculentus*), harbor seal (*Phoca vitulina*), European stag beetle (*Lucanus cervus*), African elephant (*Loxodonta africana*), house mouse (*Mus musculus*), green sea turtle (*Chelonia mydas*), or from any other appropriate animals.

In one aspect of the invention the cultivated cells may be bovine cells. The bovine cells may be selected from the group of stem cells, comprising embryonic stem cells and other cell types derived from blastocyst or other early-stage embryos, muscle stem cells such as myosatellite cells, mesenchymal stem cells or stem cells derived from bone marrow, fat tissue, subcutaneous tissue or other tissues, or cells where the stemness character is induced or established afterward such as induced pluripotent stem cells. Other used bovine cell types may be bovine myoblasts, myocytes, fibroblasts, fibro-adipogenic progenitors, preadipocytes, adipocytes, epithelial cells cartilage and tendon-derived cells such as chondroblasts and chondrocytes, macrophages, keratinocytes, hepatocytes, testicular cells, Sertoli cells, mesenchymal stem cells, myosatellite cells, or a combination thereof.

In one aspect of the invention, the cells used for cultivation processes in the culture media according to the invention may be in at least one form of: a single cells; cell aggregates, which may take the form of cell clumps (loosely connected aggregates), spheroids (compact homogeneous aggregates) and/or organoids (compact heterogeneous aggregates); cells connected to carriers such as microcarriers, macrocarriers or microfragments; or in any other appropriate form of cells. The cells used for cultivation processes in the culture media according to the invention may be immortalized.

Culture Media Preparation—General Description

The culture medium may be prepared by dissolving the individual media components in water or a suitable aqueous buffer. The components may be sterilized by a suitable sterilization method in order to remove fungi, bacteria, viruses and other possible contaminating agents. Sterilization may occur before or after dissolving of the medium component. Sterilization may be performed by physical or chemical methods. Chemical methods may include treatment with ozone, chlorine dioxide, ethylene oxide, or any other suitable chemical compound. Physical methods may include treatment with wet or dry heat, ionizing radiation, or any other suitable physical influence. Additionally, for aqueous solutions of media components which are solids, aqueous solutions of media components which are liquids, or separate media components which are liquids, filtration may be used as a method of sterilization. Advantageously, physical methods of sterilization (including filtration) may be used, as they minimize the risk of contamination of the final product with the residues of chemical disinfectants. Advantageously, some medium components or their solutions may be mixed together before sterilization, therefore reducing the number of materials which need to be sterilized separately.

For filter sterilization of a culture medium or its components, the material of the filter may be polyethersulfone, cellulose acetate, ceramic, or any other suitable filter material. The size of the largest pores of the filter may be in the range of 0.001 μm to 10 μm, or in the range of 0.01 μm to 2 μm, or in the range of 0.05 μm to 0.5 μm. Filtration may be carried out as dead-end filtration, tangential flow filtration, alternating flow filtration, or any other suitable filtration setup.

The medium may be stored as the final complete culture medium solution, or as a set of at least one solid component or mixes of solid components, or as a set of at least one concentrated solution of one or more components, or as a set of one or more liquids, or a combination of the above.

The culture medium according to the present invention may be prepared in a culture medium tank. The culture medium tank may comprise at least one of: mixing tank, hydrolysis tank, storage tank, loading tank or waste medium tank, or any other appropriate device.

The media components may be mixed in a mixing tank, which may be made from stainless steel, glass, or any other suitable material. The mixing tank may be equipped with a stirring unit comprising, for example, a shaft with one or more impellers. The mixing tank may be equipped with a heating system. The temperature may be in the range of 10 to 40° C., or in the range of 15 to 38° C., or in the range of 18 to 35° C. The mixing tank may be connected to one or more storage tanks. The mixing tank may be connected to one or more cultivation devices, formed for example by a bioreactor. The culture medium components may be mixed directly in the cultivation device.

The volume of the mixing tank may be in the range of 500 mL to 100 m³, or in the range of 1 L to 10 m³, or in the range of 2 L to 5 m³, or in the range of 500 L to 3 m³.

The storage tanks may be made from stainless steel, glass or any other suitable material. The volume of the storage tank may be in the range of 500 mL to 100 m³, or in the range of 1 L to L to 5 m³, or in the range of 2 L to 3 m³, or in the range of 500 L to 1 m³.

The media components may be dosed into the mixing tank through sterilization filter, or may be sterilized prior to the placement to the mixing tank or may be sterilized in the mixing tank.

The mixing tank may be equipped with different types of sensors, such as, for example, thermal sensor, pH probe, conductometer, or any other type of appropriate sensor according to the needs of the process.

The processes of cell cultivation in culture media according to the present invention may be performed in a cultivation system. In one aspect of the invention, the cultivation system 1 is as depicted in FIG. 1. The cultivation system 1 may comprise a seeding tank 2, a cultivation device 3, a harvesting device 4, a control unit 5, and sensors and analytical instruments 6 as depicted in FIG. 1. Optionally, the cultivation system 1 may further comprise a device for preparing food products (not depicted in FIG. 1).

The control unit may control and/or regulate every process taking place within the cultivation system. The control unit may be operated using at least one printed circuit board (PCB) and/or microprocessor with software capable of controlling the cultivation device, regardless of the extensions and scale of the system. The control unit may be connected to at least one central data storage. The cultivation system may comprise one or more subcontrol units.

The culture media according to present invention may comprise protein hydrolysate as source of amino acids.

The process of medium preparation may further have the characteristics of a batch process, a continuous process or a combination thereof as described below.

Medium Preparation—Batch Process

In the batch process of medium preparation, the complete culture medium may be prepared, introduced into the cultivation device and subsequently inoculated with cells.

The complete culture medium may be mixed in a mixing tank, or the culture media components may be mixed directly in the cultivation device, as described above.

The complete medium may be sterilized in the mixing tank, in the cultivation device, or during transfer from the mixing tank to the cultivation device, if they are separate. Alternatively, the individual culture media components or mixture of these components may be sterilized before being added to the mixing tank or during transfer to the mixing tank, yielding a sterile complete culture medium.

Medium Preparation—Continuous Process

In the continuous process of the culture medium preparation, the preparation of the medium may take place simultaneously with the cultivation of cells.

Individual culture medium components or mixture of components may be introduced into the cultivation device during cell cultivation. The components may be sterilized before or while being transferred into the cultivation device. The components may be introduced to the cultivation device in any form, for example they may be introduced as aqueous solutions, allowing convenient filter sterilization and fast mixing of all culture media components in the cultivation device.

The rate of addition of culture media components may be fixed, or the rate of addition may be adjusted to ensure optimal conditions for cell cultivation in the cultivation device. These optimal conditions may include, but are not limited to, the ranges of pH, osmolality, shear protectant concentration, sugar concentration and amino acid concentration as specified herein in the section entitled culture media composition.

Conditions in the cultivation device may be determined by: a pH probe, a conductometer, an osmometer, a glucose prober, a refractometer, an UV-Vis spectrometer, a Raman spectrometer, or any other appropriate measurement method. In appropriate cases, concentration of specific compounds in the cultivation device may also be approximated by a mass balance equation.

To achieve the desired conditions in the cultivation device, the flow rates of medium components may be adjusted using a suitable control mechanism, for example a PID control loop.

In one aspect of the invention, the continuous medium mixing process may comprise the following steps:

- introduction of a concentrated basal medium into the cultivation device at a defined flow rate, for example if the basal medium is X times more concentrated than the desired concentration in the final medium, the basal medium is introduced at a flow rate 1/X times the total output flow rate from the cultivation device
- introduction of a concentrated sugar solution into the cultivation device wherein the flow rate is controlled so that the concentration of the sugar in the cultivation medium is kept at a desirable setpoint, for example 1 g/L
- introduction of a solution of hydrolysate and amino acids into the cultivation device wherein the flow rate is controlled so that the concentration of amino acids in the medium is kept at a desirable setpoint
- introduction of a concentrated solution of NaCl into the cultivation device wherein the flow rate is controlled so that the total osmolality of the medium is kept at a desirable setpoint, for example 310 mOsm/kg
- introduction of demineralized water into the cultivation device wherein the flow rate is adjusted to be equal to the difference of the total output flow rate from the cultivation device and the sum of all other input flow rates, thereby keeping a constant volume of liquid in the bioreactor.

Hydrolysate Preparation—General Description

The protein source for hydrolysis may be selected from an industrially scalable protein source. Industrially scalable protein sources include phototrophic organisms, such as land plants, green algae, red algae, brown algae, or other phototrophic eukaryotes, phototrophic prokaryotes such as cyanobacteria, or cultivated heterotrophic prokaryotes or eukaryotes, such as bacteria or yeast. The organism used as a protein source may be able to synthesize all amino acids from inorganic nitrogen sources, such as ammonia ions, nitrate ions or molecular nitrogen. The hydrolysis may be performed, for example, in a hydrolysis tank, or in any other suitable device.

The hydrolysis may be performed on a protein isolate or concentrate from the source organism, or on the whole biomass of the source organism. The source organism may be mechanically or chemically pretreated to improve the speed and efficiency of the hydrolysis process. Saccharides, fats or other compounds may be removed from the biomass of the source organism to facilitate easier processing. Examples of suitable industrially scalable protein sources may include soy, pea, rice, wheat, corn, fava beans, alfalfa, hemp, chickpea, potato, pumpkin, rapeseed, red lentil, Spirulina, Chlorella, sunflower, water lentil, mung bean, flax or baker's yeast. The present invention is not limited to the listed exemplary protein sources.

The protein hydrolysate or multiple hydrolysates from the same or different source organisms may serve as a source of all important amino acids in culture media for the purpose of cell cultivation, or some amino acids may be supplied separately, for example methionine, which is found in very low concentrations in most scalable protein sources. Other different individual amino acids may be supplied separately from a different source than a protein hydrolysate. Typically, methionine and some non-essential amino acids, such as asparagine or glutamic acid, are commercially available wholesale (in food grade) at prices compatible with use in industrial-scale cell cultivation. However, the majority of essential amino acid content of the media according to the invention may be sourced from hydrolysates. The approach may be more economically feasible at large scale than using individual free amino acids, as is commonly done in the biopharmaceutical industry or basic research.

The process of hydrolysis entails breaking the original protein molecule into shorter peptide chains and/or single amino acids. As used herein, the term "protein hydrolysate" is understood to be a mix of amino acids, peptides and other molecules prepared from a suitable protein source by any suitable method, including acidic, basic, or enzymatic hydrolysis, autolysis or lysis by fermentation with a suitable microorganism which is able to break down the protein. The "protein hydrolysate" according to the present disclosure may be, for example, plant protein enzymatic hydrolysates, various types of yeast extracts or lysates (such as whole yeast autolysate), or algae acidic hydrolysate.

Methods of protein hydrolysis may include acidic hydrolysis, basic hydrolysis, enzymatic hydrolysis, or autolysis. Acidic hydrolysis subjects the protein source to a very low pH, usually at an elevated temperature. The duration of reaction may be hours or days. Acidic hydrolysis unfortunately leads to significant degradation of several amino acids, most notably tryptophan, which would then have to be sourced separately at significant costs. Significant degradation of some amino acids also occurs during basic hydrolysis, which subjects the protein source to a very high pH, usually at an elevated temperature. Additionally, the acid or base used for the hydrolysis would have to be removed from the hydrolysate before it could be used to cultivate cells, presenting further complications. For example, when acidic hydrolysis is performed using hydrochloric acid, the acid may be removed by neutralization or evaporation. However, both processes are economically unfavorable because: i) neutralization process results in unfavorably high concentration of salts, which also need to be removed, and ii) evaporation is energy-intensive and the resulting HCl vapors pose a health and environmental hazard that would need to be solved. The process of autolysis relies on the activity of the endogenous enzymes of the source organism to break down the protein source, and this process is usually not very efficient and does not generally result in sufficient hydrolysis of the source protein. Additionally, proteins can be broken down by fermentation with organisms such as *Bacillus licheniformis* or *Aspergillus oryzae*, which produce a large amount of proteolytic enzymes. However, with this approach, some of the amino acids from the source protein may be consumed by the organism that was used to break down the protein during the process of fermentation. Also, metabolic waste products and other compounds from the fermenting organism may contaminate the resulting lysate and adversely affect its properties in respect to mammalian cell cultivation.

The hydrolysate according to the invention may be obtained by enzymatic hydrolysis of a suitable protein source. The industrially scalable protein source is advantageous. In one aspect of the invention soy protein isolate may be used as the protein source for enzymatic hydrolysis. Advantageously, soy protein isolate has a favorable ratio of most amino acids for the purpose of mammalian cell cultivation, with the exception of methionine which is present at a relatively low concentration. However, methionine may be added to the media separately as mentioned above.

The protein substrate for hydrolysis in solvent may be subjected to an initial thermal pretreatment to improve solubility and susceptibility to hydrolysis. The temperature during the thermal pretreatment may be in the range of 75 to 95° C., or in the range of 80 to 92.5° C., or in the range of 85 to 90° C. for a time range of 5 to 120 minutes, or 15 to 60 minutes, or for a time range of 30 to 45 minutes.

The method of enzymatic hydrolysis may use a so-called protease, an enzyme that catalyzes the breakdown of peptide bonds in order to achieve protein hydrolysis at much milder conditions than acidic or basic hydrolysis, therefore preserving all of the amino acids of the original protein.

In one aspect of the invention, the enzyme used for hydrolysis may be immobilized on a solid support. This approach sterically prevents the molecules of the enzyme from breaking each other down and allows the enzyme to be separated from the reaction mixture after the reaction and used again. The solid support may be present in the form of solid carriers suspended in the reaction mixture, or a solid structure with a large surface area, such as a sponge or fibrous structure, through which the reaction mixture is perfused. The enzyme may also be added in soluble (free) form. After hydrolysis is complete, the resulting hydrolysate is separated from the solid support with immobilized enzyme by simply draining the reaction vessel (in the case of large solid structure) or removing the enzyme on solid support by filtration or sedimentation (in the case of suspended carriers). The reaction vessel may be formed, for example, by a hydrolysis tank. The filtration step may also remove any solid residues from the source protein, such as cell wall debris. Free enzymes may be removed from the hydrolysate by ultrafiltration or deactivated with elevated temperature when hydrolysis is complete. Ultrafiltration of the hydrolysate may additionally remove any larger peptide chains which were not digested by the enzyme; these peptide chains may be harmful to the cells and therefore their removal may be beneficial. The temperature elevation used to deactivate the enzyme may also sterilize the resulting hydrolysate.

The hydrolysate may be thermally treated at the end of hydrolysis to deactivate enzymes and kill microorganisms. In one aspect of the invention, this treatment may be with lower temperature settings in the range 80 to 120° C., or 85 to 100° C., or in the range 90 to 95° C. with longer time in the range of 15 to 180 minutes, or 20 to 120 minutes, or in the range 25 to 60 minutes. In another aspect of the invention, this treatment may be performed with higher temperature in the range 80 to 160° C., or 100 to 155° C., or in the range 110 to 150° C. with shorter time in the range of 1 to 600 seconds, or 3 to 300 seconds, or in the range of 5 to 60 seconds. Method with lower temperature setting may be performed in reactor setting and both methods may be performed in flash pasteurizer or another suitable continuous flow heating device.

If the enzyme is removed by ultrafiltration, it may retain at least partial catalytic activity and thus may be recycled for another round of hydrolysis. Ultrafiltration or thermal deactivation may also be used to remove active enzyme molecules from hydrolysates prepared by immobilized enzymes, in the event that some of the enzyme detaches from the solid support and dissolves into the reaction mixture.

The solid support may be formed by, for example, silica, epoxide resin, cellulose, chitosan, glass wool, alginate, or by other appropriate materials. The solid support may be in the form of porous or solid beads, sponge, fibers, or another suitable configuration. The solid support may have a large surface area to volume ratio to allow the binding of a large amount of enzyme. For example, beads of porous silica or any other suitable material with a diameter in the range of 1 to 10000 micrometers, or in the range of 10 to 1000 micrometers, or in the range of 20 to 500 micrometers, may be used as a solid support for enzyme immobilization. Immobilization may be achieved, for example, by functionalizing the silica bead surface with amino groups and using a crosslinking agent, such as glutaraldehyde, to bind the enzyme to the solid support. Other functional groups, like aldehyde or epoxy groups, may also be used for enzyme immobilization. The amino groups in this aspect of the invention are covalently bonded to glutaraldehyde, after which excess glutaraldehyde is removed and the enzyme is added. The amino groups on the surface of the enzyme then bind the remaining free aldehyde groups of the glutaraldehyde molecules on the silica bead surface. The immobilization may be performed in water or a suitable aqueous buffer. Thanks to the porous nature and large surface area of the silica beads, a relatively high amount of enzyme may be immobilized relative to the weight of the solid support.

The enzymes according to the invention may be, for example, Alcalase (protease from *Bacillus licheniformis*), Flavourzyme (protease from *Aspergillus oryzae*), Protamex, Novo-Pro D, Thermoase PC10FNA, Protease AN Amano 100SD, Protease A Amano 2SD, Protease M Amano SD, Protease P Amano 6SD, ProteAX, Peptidase R, Alkaline Protease, Corolase 7089, Corolase 2TSN, Corolase 8000, Maxipro TNP, Maxipro FPC, Papain, Bromelain, or any other appropriate proteolytic enzyme, or the combination thereof.

Water, or a suitable aqueous buffer, may be used to dissolve the protein source for the hydrolysis. Some proteins may require a buffer to adjust the pH to a level where they have better solubility. The pH may be in the range of 2 to 12, or in the range of 5 to 10, or in the range of 6 to 8.5. A very dilute buffer, or no buffer at all, may be used so that the resulting hydrolysate may be added to the final culture media at high concentrations while minimizing its impact on media osmolarity.

The buffer may include, for example, phosphate buffer, bicarbonate buffer, tris HCl buffer, borate buffer, glycine-NaOH buffer, Good's buffer or any other appropriate buffer, or a combination thereof.

The concentration of the protein in the reaction mixture for hydrolysis may be in the range of 1 to 150 grams per liter, or in the range of 20 to 100 grams per liter, or in the range of 30 to 80 grams per liter of the reaction mixture.

The concentration of the enzyme may be in the range of 0.01 to 10% or in the range of 0.05 to 5%, or in the range of 0.1 to 1% expressed as a ratio of the concentration of enzyme to the concentration of protein in the reaction mixture (further referred to as enzyme/protein ratio). The concentration of the enzyme may be determined by the Bradford assay, BCA assay or other protein determination assays.

In one aspect of the invention, the concentration of potassium phosphate buffer in the range of 1 to 100 mM, or in the range of 10 to 40 mM, or in the range of 15 to 35 mM may be used for pH adjustment to dissolve the soy protein to a concentration in the range of 1 to 150 grams per liter, or in the range of 20 to 100 grams per liter, or in the range of 30 to 80 grams per liter. In another aspect of the invention, the soy protein is dissolved in distilled water to a concentration in the range of 1 to 150 grams per liter, or in the range of 20 to 100 grams per liter, or in the range of 30 to 80 grams per liter.

Other concentrations of the source protein may be used, however very high concentrations of source protein lead to incomplete dissolving of the protein and formation of a highly viscous colloidal solution, presenting problems for the hydrolysis and further processing, while low concentrations of protein may limit the speed of the hydrolysis reaction. To ensure the best dissolution of the proteins in the reaction mixture a heat-treatment may be used. Below boiling temperatures may be used for extended periods of time in order to significantly increase the content of dissolved proteins and to deactivate potential inhibitors of proteases and other antinutritional compounds.

In one aspect of the invention, the source protein may be added at a higher concentration than the maximum soluble concentration. This additional protein may be dissolved after the protein concentration in the reaction mixture is decreased due its hydrolysis by the enzyme. This results in high concentration of available substrate during the entire process, potentially improving hydrolysis efficiency. Multiple cycles of substrate addition into the same reaction mixture may be performed. In one aspect of the invention a base or a suitable buffer may be added to counteract the change and keep the enzyme in its pH optimum or a pH stat may be used The key parameter by which we can evaluate the conversion of substrate protein into products bioavailable for animal cells is the degree of hydrolysis, defined as the percentage of peptide bonds in the source protein that are hydrolyzed during the reaction. A higher degree of hydrolysis corresponds to a larger percentage of the source protein converted into free amino acids or short peptides, which are usable by mammalian cells as nutrition. Mammalian cells are generally incapable of absorbing and digesting proteins and longer peptides. Peptides longer than four amino acids, or in other words heavier than approximately 500 Daltons, have very poor absorption by mammalian cells. In various aspects of the invention, the amount of the source protein in the range of 20% to 100%, in the range of 30% to 70%, or in the range of 35 to 65%, or in the range of 40% to 60% may be converted into free amino acids, expressed as mass concentration of amino acids to mass concentration of protein. The degree of hydrolysis (DH), meaning the percentage of peptide bonds that undergo hydrolysis out of the total amount of peptide bonds present in the substrate at the start of the reaction, may be in the range of 10% to 60%, in the range 20% to 50%, or in the range of 25% to 40%.

Enzymes used for hydrolysis may fall into two general categories: exoproteases and endoproteases. Exoproteases cleave the protein or peptide chains at the ends, whereas endoproteases can cleave peptide bonds in the middle of the chain. In one aspect of the invention, a combination of endoproteases and exoproteases may be used, since endoproteases may create more free ends of peptide chains, increasing the efficiency of exoproteases, and exoproteases are more efficient in hydrolyzing the protein to single amino acids. In one aspect of the invention, endoproteases and exoproteases may be used sequentially in this order to maximize hydrolysis efficiency.

In one aspect of the invention, additional enzymes may be added to the reaction mixture after the beginning of hydrolysis. This may be done with the same enzyme, mainly in order to counteract the gradual decrease in its enzymatic activity due to degradation of the enzyme molecule. In one aspect of the invention, enzymes with a higher pH optimum may be added at the start of the hydrolysis, when pH is higher, and enzymes with a lower pH optimum may be added later, when the pH is lower, thus maximizing the efficiency of the respective enzymes. The pH tends to decrease naturally during hydrolysis due to the increase in the number of carboxylic groups.

In another aspect of the invention, additional substrate may be added to the reaction mixture after the beginning of hydrolysis. The advantages of this approach may be, for example, easier dispersion and dissolution of additional substrate when the previous amount of substrate is at least partially hydrolyzed.

The addition of enzyme or substrate after the beginning of the hydrolysis process may be performed in a fed-batch (additional reagents are added to the reaction mixture, and subsequently the whole reaction batch is harvested) or in continuous (addition to and harvesting from the reaction mixture are both done continuously) reaction mode.

Regardless of whether immobilized or free enzyme is used, sufficient mixing of the reaction mixture is important to achieve high efficiency. In the case of immobilized enzymes, this applies to both the enzyme immobilization and protein hydrolysis steps. In one aspect of the invention, in the case of immobilized enzymes, mixing methods which minimize mechanical damage to the solid carriers should be used. These may include roller mixing, shaking, or low-shear impellers such as hydrofoil or elephant ear impellers. In the case of enzymes immobilized to a large solid support, sufficient perfusion of the support with the reaction mixture must be assured.

The mixing of the protein source, e.g. protein isolate, with water, or with a suitable aqueous buffer, dissolving the protein source and the process of hydrolysis itself may be performed in an appropriate reaction vessel in a laboratory or industrial scale. The reaction vessel may be formed, for example, by a hydrolysis tank.

The reaction vessel for hydrolysis may comprise, for example, a batch reactor, continuous stirred tank reactor, or plug flow reactor. The volume of the reaction vessel may be in the range of 0.1 L to 100,000 L, or in the range of 0.3 L to 15 000 L, or in the range of 1 L to 5,000 L.

The mixing may be provided by the appropriate stirring unit that may comprise, for example, a paddle impeller. The elephant-ear impeller may be used. The outer diameter of stirrer or impeller may be in the range of $\frac{1}{10}$ to $\frac{9}{10}$ of the inner reactor diameter, or in the range of $\frac{3}{10}$ to $\frac{8}{10}$ of the inner reactor diameter, or in the range of $\frac{4}{10}$ to $\frac{7}{10}$ of the inner reactor diameter, for example $\frac{2}{3}$ of the inner reactor diameter. The stirrer or impeller may be located in the center of the reaction vessel or outside of the center of the reaction vessel.

The reaction components may be added to the reaction vessel manually, or based on gravity from the storage tank connected to the reaction vessel, or using a pumping system. The source protein may be in a liquid solution or in a form of powder and may be added to the reaction vessel manually or automatically.

The storage tank may be made, for example, of stainless steel or glass. The volume of the storage tank may be in the range of 100 ml to 5 m³, or in the range of 2 L to 3 m³, or in the range of 500 L to 1 m³.

The reaction vessel, for example a hydrolysis tank, may be equipped with different types of sensors, such as, for example, thermal sensor, pH probe, conductometer, or any other type of appropriate sensor according to the needs of the process of hydrolysis. The pH may be monitored during the whole procedure by a pH electrode. The temperature in the reaction vessel may be regulated, for example, with a reactor thermal jacket, which may be equipped with a heating coil and/or heating/cooling medium.

For precise monitoring of the degree of hydrolysis a sampling system may be used. The degree of hydrolysis may be monitored by titration and/or by absorbance measurement, for example at a wavelength in the range of 190 to 350 nm, or 190 to 230 nm.

After the hydrolysis process, another treatment may be used to reduce the content of phytic acid. Phytic acid is an important compound in plant metabolism, its salt form—phytin is the main storage compound of phosphorus in plants. On the other hand, phytic acid represents one of the antinutrient compounds in legumes, which can significantly influence the downstream processes as well as cell proliferation and viability. An enzymatic treatment or any other method to reduce the content of phytic acid may be used. If enzymatic treatment is used, the selection of the proper phytase enzyme is crucial as well as the proper conditions in regards to pH and temperature. The process may comprise addition of the phytase enzyme in concentration correlation to Enzyme/Substrate ratio, where substrate means the source of protein used. The Enzyme/Substrate ratio may be in the range of $1.1 \cdot 10^{-11}\%$ to 1%, or in the range of $1.1 \cdot 10^{-10}\%$ to 0.001%, or in the range of $1.1 \cdot 10^{-9}\%$ to 0.0001%. The temperature may be in the range of 20° C. to 80° C., in the range of 30° C. to 70° C., or in the range of 40° C. to 60° C. After the enzymatic treatment for time period in the range of 20 minutes to 4 hours, or in the range of 30 minutes to 3 hours, or in the range of 1 to 2 hours, the heat-treatment for enzyme deactivation may be applied. Deactivation may be performed for example for 30 minutes at 90° C., or 15 minutes at 95° C.

For the purpose of filtration, for example for removing impurities, for separation of enzyme immobilized on a carrier from the reaction mixture, or for separation of larger peptides from hydrolysate, appropriate filtration unit equipped with filtration materials may be used. The filtration material may be, for example, filtration fabrics, ceramics, glass, membranes or other suitable materials. The size of pores in filtration material may be for example, but not limited to, 500 μm-10 μm for filtration, 10 μm to 0.1 μm for microfiltration, 0.1 μm to 1 nm for ultrafiltration and 1 nm to 0.1 nm for nanofiltration. The membranes characterized with the range of 60 kDa to 500 Da may be used. As a prior step to filtration, centrifugation may be used to ease the process of filtration.

Hydrolysis by Free Enzyme

In one aspect of the invention, hydrolysis by free enzymes may be performed by dissolving the protein substrate in the reaction vessel formed, for example, by a hydrolysis tank. This protein substrate may be, for example, whole biomass, protein concentrate, protein flour, raw protein meal, protein extractor protein isolate from soy, pea, rice, wheat, corn, fava beans, alfalfa, hemp, chickpea, potato, pumpkin, rapeseed, red lentil, Spirulina, Chlorella, sunflower, water lentil, mung bean, flax or yeast, or another suitable protein source.

The concentration of protein in the reaction mixture may be in the range of 1 g/L to 150 g/L, or in the range 20 g/L to 100 g/L, or in the range of 30 to 80 g/L. For a given volume of the reaction mixture, the Alcalase may be added in calculated amounts accordingly to the Enzyme/Protein ratio in the range of 0.01 to 10%, or in the range of 0.05 to 3%, or in the range of 0.1 to 0.8% of the concentration of the enzyme/the concentration of the protein. The resulting mixture has a neutral to basic pH, allowing for a high activity of Alcalase. The temperature may be in the range of 50° C. to 70° C., or in the range 55° C. to 65° C., or in the range of 58° C. to 63° C. Over a period of constant mixing, which may be in the range of 30 minutes to 24 hours, or in the range of 1 to 12 hours, or in the range of 2 to 8 hours, the pH of the mixture decreases as the results of the hydrolysis of peptide bonds and increased number of carboxylic groups.

This allows for a high activity of Flavourzyme, which may be added in calculated amounts accordingly to the Enzyme/Protein ratio in the range 0.01 to 10%, or in the range 0.1 to 2%, or in the range of 0.2 to 1% Enzyme/Protein ratio to the reaction mixture. The resulting mixture may then be incubated for an additional time period in the range of 1 hour to 48 hours, or in the range of 5 to 24 hours, or in the range of 8 to 20 hours at temperature in the range of 30 to 80° C., or in the range of 40° C. to 70° C., or in the range of 45 to 60° C., with constant mixing, after which the residual enzyme is thermally deactivated. With this procedure, 20% to 100%, 30% to 70%, or 40% to 60% of the source protein may be converted into free amino acids.

Hydrolysis by Immobilized Enzyme

The protein hydrolysis process may be carried out in the reaction vessel formed, for example, by a hydrolysis tank. The protein hydrolysis may be carried out with immobilized enzyme in an amount in the range of 0.01 g to 10 g, or in the range of 0.25 to 1.8 g, or in the range of 0.5 to 1.5 g on 10 grams of enzyme carrier. The enzyme carrier may be made from glass, porous silica, alginate, epoxy methacrylate, chitosan, or from any other suitable material, in the form of beads, wool, sponge, fibers, or in any other suitable form. The enzyme carrier may be, for example, formed by glass beads, porous silica beads, alginate beads, epoxy methacrylate beads, glass wool, chitosan, or any other suitable enzyme carrier. Suitable enzyme carriers are described in more detail in the section herein entitled "Hydrolysate preparation—general description". For example, 1 gram of immobilized enzyme on 10 grams of porous silica beads may be used.

The immobilized enzymes may be prepared by suspending a set weight of $NH_2$-functionalized porous silica microbeads in the set weight of distilled water. The ratio of set weight of $NH_2$-functionalized porous silica microbeads versus distilled water may be in the range of 1:1 to 1:10000, or in the range of 1:10 to 1:1000, or in the range of 1:20 to 1:100. Silica beads are further activated with the addition of glutaraldehyde. The amount of glutaraldehyde added to the reaction mixture may be in the range of 0.01 to 70 mmol, or in the range of 0.05 to 40 mmol, or in the range of 0.1 to 10 mmol of glutaraldehyde per 1 g of silica beads. The excess glutaraldehyde is washed away, and the silica beads are resuspended, for example, in half the original volume. Alcalase is then added to a final concentration with constant stirring. This procedure may immobilize 10 to 100%, 60 to 90%, or 70 to 80% of the used enzyme on the silica beads. This may correspond to 10 to 100 grams, 30 to 60, or 40 to 50 grams of enzyme immobilized per 1 kilogram of silica beads.

In one aspect of the invention, silica beads with immobilized Alcalase may be added to a mixture of a soy protein and distilled water. The amount of silica beads with immobilized Alcalase may be, for example, in the range of 10 to 20 g/L, or in the range of 12 to 18 g/L, or in the range of 14 to 16 g/L, or any other appropriate amount. After hydrolysis with Alcalase the beads bound to Alcalase may be removed by centrifugation. Silica beads with immobilized Flavourzyme are added in an amount, for example, in the range of 4 to 40 g/L, or in the range of 5 to 30 g/L, or in the range of 10 to 20 g/L. The appropriate time of hydrolysis may be, for example, in the range of 10 minutes to 24 hours, or in the range of 30 minutes to 12 hours, or in the range of 1 to 6 hours.

The temperature of hydrolysis may be in the range of 10 to 90° C., or in the range of 25 to 80° C., or in the range of 50 to 70° C. In another aspect of the invention, Alcalase beads may not be removed at this step and may instead be removed at the end of the process. In yet another aspect of the invention, Alcalase and Flavourzyme beads may have different sizes, facilitating their separation after removal from the solution. In another aspect of the invention, Flavourzyme beads may be added at the start of hydrolysis or at any other point during the hydrolysis. After further hydrolysis, for a time period which may be in the range of 1 to 24 hours, or in the range of 6 to 20 hours, or in the range of 10 to 18 hours, at a temperature which may be in the range of 20 to 90° C., or in the range of 30 to 80° C., or in the range of 40 to 60° C., with constant mixing, the Flavourzyme beads are removed by centrifugation and the resulting hydrolysate is thermally sterilized, which also deactivates any enzyme which could have detached from the solid support. After filtration to remove solid debris, the hydrolysate can be used to prepare culture media. With this method, the amount of source protein in the range of 20 to 100%, or in the range of 30 to 95%, or in the range of 40 to 90%, may be converted into cell-usable products, meaning free amino acids or peptides of 500 Da or less.

Since Alcalase and Flavourzyme are quite stable in their immobilized form, they may be recycled in the hydrolysate production process according to the invention. In one aspect of the invention, the silica beads with immobilized Alcalase may be used for 2 to 50, 5 to 40, or 10 to 30 cycles of hydrolysis while maintaining around half of their original catalytic activity. In another aspect of the invention, silica beads with immobilized Flavourzyme can be used for 2 to 50, 5 to 40, or 10 to 30 hydrolysis cycles while maintaining sufficient catalytic activity. Generally, even though immobilized enzymes tend to be more stable than free enzymes, their enzymatic activity decreases with use. Therefore, in later cycles, duration of the reaction or enzyme to protein ratio may be changed to maintain a consistent quality of the resulting hydrolysate.

Culture Media Composition

In one aspect of the invention, the composition of the culture medium may be defined in terms of the total input of medium components into the cultivation process. In this aspect of the invention, summary amounts of components introduced into the cultivation process at any time point over its entire duration are provided. Furthermore, in this aspect of the invention, the provided concentration ranges for the individual medium components describe the total amount of the given component introduced into the cultivation process at any time point during the cultivation process in relation to the volume of spent culture medium which exits the process. The spent culture medium may exit the cultivation process together with the cultivated cells (harvesting), or separately from the cultivated cells (perfusion). The cultivation process may further have the characteristics of a batch process, where all of the components are introduced into the cultivation process at a single time point and the harvest is performed at a single time point, a fed-batch process, where some components may be introduced after the start of the process and the harvest is done at a single time point, a continuous process, where components may be introduced during the whole duration of cultivation and harvesting may be performed during the whole duration of cultivation, or a combination of the described characteristics. For brevity, this aspect of the invention will be referred to herein as "total input".

In another aspect of the invention, the composition of the culture medium may be described in terms of the concentration of components which are present at a particular time point during the cell cultivation process in the culture medium. In this aspect of the invention, the provided concentration ranges for the individual medium components describe the concentrations present in the culture medium in the cultivation device at any time point during the cultivation process. For brevity, this aspect of the invention will be referred to herein as "momentary composition".

Total Input

The total inputs into the culture medium according to the invention may comprise an optimized ratio essential of amino acids, which may be sourced from a protein hydrolysate, in combination with at least one type of compound selected from a group comprising: sugars, vitamins and organic micronutrients, mineral compounds, iron supplementation compounds, organic amines, and shear protectants, or a combination thereof. The media may also contain other compounds, like fatty acids, phospholipids, or nucleic acids, for example. Media according to the invention with an optimized ratio of amino acids and other nutrients may facilitate efficient production of biomass and a low production of waste metabolites, such as ammonia or lactate, by the cells.

An optimized ratio of essential amino acids is such that essential amino acids may be introduced into the cultivation process in any ratio where the percentage of essential amino acids that can be converted into cellular protein is in the range of 5% to 100%, or in the range of 20 to 90%, or in the range of 30 to 80%. The term "highest possible conversion efficiency" determines what percent of the essential amino acids provided to the cells can be converted into cellular protein, assuming no loss of amino acids to catabolism, conversion to other compounds (nucleic acids, for example), or spontaneous degradation.

The highest possible conversion efficiency is determined by the essential amino acid that is the most limiting to the cells. It is calculated such as that for all individual essential amino acids added to the medium in any form at any time point during the cultivation process, the content of that particular essential amino acid in the culture media as a fraction of total essential amino acid content added in any form at any time point to the culture media is divided by the content of that individual amino acid in cellular protein as a fraction of total content of essential amino acids in the lowest obtained ratio, in other words the ratio for the essential amino acid which forms the lowest percentage of the amino acids added to the medium in comparison to the percentage of that particular amino acid in cellular biomass, is then multiplied by 100 to obtain the highest possible conversion efficiency of the provided essential amino acids into cellular protein. All percentages in the calculation of highest possible conversion efficiency are percentages by weight.

The amino acids in the culture media may be present in the form of free amino acids or peptides. Non-essential amino acids are omitted in this calculation, as they can be synthesized by the cells and thus are not limiting in terms of the highest possible conversion efficiency. An example of possible essential amino acid content in cellular protein can be seen in Table 1 below.

The above description may be summarized by the following equation:

$$H_{EAA} = \frac{\dfrac{A_{EAAM}}{\sum A_{EAAM}}}{\dfrac{A_{EAAC}}{\sum A_{EAAC}}} * 100,$$

where $H_{EAA}$ is the highest conversion efficiency for a particular amino acid, $A_{EAAM}$ is the content of that particular essential amino acid in 100 g of protein in culture medium, $\Sigma A_{EAAM}$ is the total content of all essential amino acids in 100 g of protein in culture medium, $A_{EAAC}$ is the content of that particular essential amino acid in 100 g of cellular protein and $\Sigma A_{EAAC}$ is the total content of all essential amino acids in 100 g of cellular protein.

An example calculation for the essential amino acid tryptophan would proceed as follows: assuming that the total amount of tryptophan added to the culture media over the period of cultivation was 2 grams, and the total amount essential amino acids added to the media over the same time period was 100 grams. Table 1 shows that in 100 grams of cellular protein, out of 44.7 grams of total essential amino acids, 1.6 grams are tryptophan.

The Calculation:

$$H_{EAA} = \frac{\dfrac{2}{100}}{\dfrac{1.6}{44.7}} * 100 = 55.875\%$$

shows that the highest conversion efficiency for tryptophan is 55.875%. Now, this process is repeated for each of the nine individual essential amino acid. The lowest of nine numbers obtained is the final highest conversion efficiency.

The amount of essential amino acids that can be converted into cellular protein is determined by how closely the total input of essential amino acids into the cultivation process matches the amino acid composition of cellular protein. Because cells cannot synthesize essential amino acids, the essential amino acid with the lowest relative total input into the cultivation process in comparison to its content in cellular protein will limit maximal cell yield and therefore the maximal percentage of essential amino acids converted to cellular protein (this can be understood as an application of Liebig's law of the minimum).

The conversion efficiency for total essential amino acids may be in the range of 5% to 100%, 20% to 100%, 30% to 100%, or 50% to 100%, calculated by the above mentioned equation.

If the essential amino acid composition of cellular protein according to the example mentioned in Table 1 is used, the resulting total inputs of each essential amino acid given as grams per 100 grams of the total input of all essential amino acids may be in the ranges summarized in the Table 2.

The ranges of concentrations of amino acids in grams per 100 grams of total essential amino acids introduced into the cultivation process may be according to Table 2, regardless of whether the essential amino acid composition of cellular protein is according to Table 1 or not.

It should be noted that for the purpose of this equation, it is necessary to consistently consider amino acid content either as free amino acids, or as amino acids that are part of a peptide chain (in which case the molecular weight of each amino acid must be considered lower by the weight of one water molecule, to account for the fact that water is a byproduct of a peptide bond formation). In the equation above and Tables 1-3, everything is counted as amino acids that form a peptide chain. Elsewhere in the present document, when amino acid input or concentration is discussed, these are calculated with the molecular weights of free amino acids, and when protein input or concentration is discussed, it is assumed that the amino acids are part of a peptide chain for any calculations.

TABLE 1 example of possible essential amino acid content in the cellular protein.

| Amino acid | content [g/100 g cellular protein] |
|---|---|
| His | 2.7 |
| Ile | 5.1 |
| Leu | 8.9 |
| Lys | 8.2 |
| Met | 2.9 |
| Phe | 4.7 |
| Thr | 4.8 |
| Trp | 1.6 |
| Val | 5.8 |
| Sum | 44.7 |

TABLE 2 ranges of concentrations of amino acids in grams per 100 grams of total essential amino acids introduced into the cultivation process.

| Amino acid | range 1 | range 2 | range 3 |
|---|---|---|---|
| His | 0.30 to 6.04 | 1.21 to 5.44 | 1.81 to 4.83 |
| Ile | 0.57 to 11.41 | 2.28 to 10.27 | 3.42 to 9.13 |
| Leu | 1.00 to 19.91 | 3.98 to 17.92 | 5.97 to 15.93 |
| Lys | 0.92 to 18.34 | 3.67 to 16.51 | 5.50 to 14.68 |
| Met | 0.32 to 6.49 | 1.30 to 5.84 | 1.95 to 5.19 |
| Phe | 0.53 to 10.51 | 2.10 to 9.46 | 3.15 to 8.41 |
| Thr | 0.54 to 10.74 | 2.15 to 9.66 | 3.22 to 8.59 |
| Trp | 0.18 to 3.58 | 0.72 to 3.22 | 1.07 to 2.86 |
| Val | 0.65 to 12.98 | 2.60 to 11.68 | 3.89 to 10.38 |

However, the composition of cell biomass is somewhat variable, and therefore the values for each essential amino acid in terms of weight percentage of total essential amino acids used in the media may also be in the ranges summarized in the Table 3.

TABLE 3 ranges of weight percentage concentration of total essential amino acids introduced into the cultivation process.

| Amino acid | range 4 | range 5 | range 6 |
|---|---|---|---|
| His | 0.2 to 7.9 | 0.8 to 7.1 | 1.2 to 6.3 |
| Ile | 0.3 to 14.9 | 1.5 to 13.4 | 2.3 to 11.9 |
| Leu | 0.7 to 25.9 | 2.7 to 23.3 | 4.1 to 20.8 |
| Lys | 0.6 to 23.9 | 2.5 to 21.5 | 3.8 to 19.1 |
| Met | 0.2 to 8.5 | 0.9 to 7.6 | 1.3 to 6.8 |
| Phe | 0.3 to 13.7 | 1.4 to 12.3 | 2.2 to 11.0 |
| Thr | 0.3 to 14.0 | 1.5 to 12.6 | 2.2 to 11.2 |
| Trp | 0.1 to 4.7 | 0.5 to 4.2 | 0.7 to 3.8 |
| Val | 0.4 to 16.9 | 1.8 to 15.2 | 2.7 to 13.5 |

Amino acids may be introduced into the cultivation process in the form of free amino acids, salts of amino acids, esters of amino acids, or any other suitable derivatives, as well as oligopeptides, for example dipeptides, tripeptides or tetrapeptides, or polypeptides. The culture medium according to the invention may comprise soy protein enzymatic hydrolysate, or any other appropriate scalable hydrolysate according to the description of hydrolysates and preparation thereof, as mentioned above. For example, the suitable industrially scalable protein sources for hydrolysate preparation may include soy, pea, rice, wheat, corn, fava beans, alfalfa, hemp, chickpea, potato, pumpkin, rapeseed, red lentil, Spirulina, Chlorella, sunflower, water lentil, mung bean or yeast. The present invention is not limited to the listed exemplary protein sources.

The total input of hydrolysate (expressed as protein dry weight) introduced into the culture medium in the cultivation process may be in the range of 1 g/L to 200 g/L, or in the range of 3 g/L to 100 g/L, or in the range of 10 g/L to 60 g/L, or in the range of 8 g/L to 50 g/L.

The total input of amino acids from hydrolysate, including amino acids in the form of short peptides or suitable bioavailable derivatives, for example phosphoesters, such phosphoserine, or other derivatives, such as methylglycine, is at least 75%, 80%, 85%, 90%, or 95% by weight of the total input of all amino acids into the culture medium.

The culture medium according to the invention may comprise amino acids added separately from the hydrolysate, for example L-methionine, L-cysteine or L-ornithine. The total input of amino acids added separately from hydrolysate may be in the range of 0.02 g/L to 30 g/L, or in the range of 0.05 g/L to 15 g/L, or in the range of 0.1 g/L to 10 g/L.

The total amount of L-cysteine in culture medium may be in the range of 0.1 to 10, or 0.5 to 7, or 1 to 5% by weight with respect to the total amount of hydrolysate protein in the culture medium.

The total amount of L-ornithine in culture medium is in the range of 0 to 5, or 0.0001 to 3, or 0.001 to 0.5% with respect to the total amount of hydrolysate protein in the culture medium.

The total amount of L-methionine in culture medium may be in the range of 0.05 to 6, or 0.1 to 3, or 0.2 to 2% with respect to the total amount of hydrolysate protein in the culture medium.

The total amount of L-tryptophan in culture medium may be in the range of 0.05 to 6, or 0.1 to 3, or 0.2 to 2% with respect to the total amount of hydrolysate protein in the culture medium.

The total amount of L-histidine in culture medium may be in the range of 0.03 to 4, or 0.07 to 2, or 0.15 to 1.5% with respect to the total amount of hydrolysate protein in the culture medium.

The total amount of L-threonine in culture medium may be in the range of 0.1 to 7, or 0.2 to 5, or 0.3 to 3% with respect to the total amount of hydrolysate protein in the culture medium.

The total input of amino acids added to the culture medium separately from the hydrolysate may be in the range of 0.2% to 25%, or in the range of 0.5 to 15%, or in the range of 1 to 10%, expressed as a percentage of the total input of hydrolysate protein into the culture medium.

The culture medium according to the invention may comprise an inorganic source of bioavailable nitrogen, for example ammonia. The total input of inorganic nitrogen source may be in the range 0 g/L to 30 g/L, or in the range 0.5 g/L to 20 g/L, 1 g/L to 10 g/L.

As a sugar may be used at least one compound selected from the group: glucose, fructose, galactose, sucrose, lactose, maltose, or a combination thereof, or any other appropriate saccharide. Total input of sugars may be in an amount in the range of 1 g/L to 350 g/L, or in the range of 2 g/L to 100 g/L, or in the range of 3 g/L to 20 g/L.

The media may contain at least one of or any combination of the following ions as a mineral compound: $Ca^{2+}$, $Cl^-$, $Cu^{2+}$, $SO_4^{2-}$, $Fe^{3+}$, $NO^{3-}$, $Fe^{2+}$, $Mg^{2+}$, $K^+$, $Na^+$, $CO_3^{2-}$, $HCO_3^-$, $H_2PO_4^-$, $HPO_4^{2-}$, $PO_4^{3-}$, $Zn^{2+}$, $SeO_3^{2-}$. The media may also contain trace amounts of other mineral compounds and elements, such as cobalt, iodine or manganese.

As the media is prepared by dissolving different constituent compounds in water, any appropriate chemical compound may be used as long as it dissociates to the desired ions in aqueous solution. For example, NaCl and KCl both produce a $Cl^-$ ion when dissolved. As another example, $CuSO_4$ and $MgCl_2$ or $MgSO_4$ and $CuCl_2$ may be used to produce $Cu^{2+}$, $Mg^{2+}$, $SO_4^{2-}$ and $Cl^-$ ions. Assuming equimolar amounts, the resulting aqueous solution will have the same composition for both combinations of compounds used. The total input of mineral compounds introduced into the cultivation process may be in the range of 0.1 g/L to 50 g/L, or in the range of 1 g/L to 20 g/L, or in the range of 3 g/L to 10 g/L.

The total input of $Na^+$ may be in the range of 20 to 120 mmol/L, or in the range of 30 to 100 mmol/L, or in the range of 40 to 80 mmol/L.

The total input of $Cl^-$ may be in the range of 25 to 130 mmol/L, or in the range of 35 to 110 mmol/L, or in the range of 45 to 90 mmol/L.

The total input of $Mg^{2+}$ may be in the range of 0.3 to 10 mmol/L, or in the range of 0.5 to 8 mmol/L, or in the range of 1 to 5 mmol/L.

The total input of $PO_4^{3-}$ may be in the range of 0.5 to 12 mmol/L, or in the range of 0.7 to 10 mmol/L, or in the range of 1 to 6 mmol/L.

The total input of $SO_4^{2-}$ may be in the range of 0.1 to 5 mmol/L, or in the range 0.3 to 3 mmol/L, or in the range 0.6 to 2 mmol/L.

The total input of $K^+$ may be in the range of 2 to 18 mmol/L, or in the range of 4 to 15 mmol/L, or in the range of 6 to 12 mmol/L.

The media may contain at least one vitamin of: alpha-tocopherol (vitamin E), ascorbic acid (vitamin C), vitamin B12, biotin, choline, pantothenic acid, folic acid, niacinamide, pyridoxine, riboflavin, thiamine, i-inositol, or a combination thereof. Any appropriate bioactive derivatives or precursors of these compounds may be used. For example, cyanocobalamin may be used instead of vitamin B12, as it can be readily converted to bioactive vitamin B12 by the cells. As another example, thiamine hydrochloride (chloride salt form of thiamine) may be used instead of thiamine. The total input of vitamins introduced into the cultivation process, omitting the vitamins present in lysates or extracts, may be in the range of 0.1 mg/L to 1,000 mg/L, or in the range of 5 mg/L to 500 mg/L, or in the range of 20 mg/L to 300 mg/L.

The total input of choline may be in the range of 10 mg/L to 1,000 mg/L, or in the range of 20 mg/L to 500 mg/L, or in the range of 30 mg/L to 200 mg/L.

The total input of niacinamide (or another vitamer of vitamin B3) may be in the range 3 mg/L to 150 mg/L, or in the range 6 mg/L to 100 mg/L, or in the range of 10 mg/L to 80 mg/L.

As an organic amine may be used at least one compound selected from: putrescine, ethanolamine, or a combination thereof, or any other appropriate amine. Organic amines total input into the cultivation process may be in an amount in the range of 0.01 mg/L to 1,000 mg/L, or in the range of 0.1 mg/L to 100 mg/L, or in the range of 0.5 mg/L to 20 mg/L.

Vitamins and organic amines or their respective precursors or derivatives may be supplied in the form of a lysate or extract, for example autolysed yeast extract or any other appropriate lysate or extract. Extract or lysate for supplementation of micronutrients may be added to the culture media in an amount in the range of 0.01 g/L to 20 g/L, or in the range of 0.1 g/L to 10 g/L, or in the range of 0.5 g/L to 5 g/L.

Iron may be supplemented to the culture medium in compounds with oxidation state iron(III) or iron(II). Iron may be present as free ions, or it may be chelated with a suitable chelating agent to improve its solubility and bioavailability. Chelating agents may include citrate, gluconate, ammonium citrate, EDTA, their combinations, or any other suitable chelating agent. Iron may be introduced into the culture medium bound to the chelating agent (for example, in the form ferric citrate), or iron and the chelating agent may be added separately (for example, in the form of ferric chloride and sodium citrate). The relative amount (w/w) of the total input of the chelating agent to the total input of iron may be in the range of 10000:1 to 1:100, or in the range of 1000:1 to 1:10, or in the range of 10:1 to 1:1. The total input of iron may be in the amount in the range of 0.00001 g/L to 0.5 g/L, or in the range of 0.0001 g/L to 0.1 g/L, or in the range of 0.001 g/L to 0.05 g/L.

The media may contain at least one shear protectant of: polyethylene glycol (PEG), Pluronic® F68 (poloxamer 188), Pluronic® F127 (poloxamer 407), methyl cellulose (MC), (hydroxypropyl)methyl cellulose (HPMC), hydroxypropyl cellulose (HPC), carboxymethyl cellulose (CMC), dextran sulfate, or any other appropriate shear protectant or their combination. The total input of the shear protectant may be in the range of 0 g/L to 50 g/L, or in the range of 0.02 g/L to 10 g/L, or in the range of 0.1 g/L to 5 g/L.

In one aspect of the invention, the culture medium may comprise a composition of total inputs as described in Table 6.

Momentary Composition

According to the present invention, the physicochemical parameters and composition of the culture medium may be optimized to facilitate fast biomass production, efficient use of nutrients and low production of waste metabolites.

The osmolality of the medium may be in the range of 200 mOsm/kg to 400 mOsm/kg, or range of 250 mOsm/kg to 350 mOsm/kg, or range of 280 mOsm/kg to 330 mOsm/kg. Osmolality may be adjusted before or after the culture medium is introduced into the cultivation device, or a combination of both, and it may be adjusted at a single time point or multiple timepoints. To increase osmolality, NaCl, KCl, glucose, any other appropriate osmolyte or their combination may be used. To decrease osmolality, water or any other appropriate dilute aqueous solution may be used.

The pH of the culture medium in the cultivation device may be in the range of 6 to 8, or in the range of 6.5 to 7.5, or in the range of 6.8 to 7.3. Adjustment of pH may be performed before or after the culture medium is introduced into the cultivation device, or a combination of both, and it may be adjusted at a single time point or multiple timepoints. NaOH, HCl, $NaHCO_3$, or any other appropriate acid or base may be used to adjust the pH; alternatively, pH may be adjusted by changing the partial pressure of CO2 in the cultivation device (higher CO2 partial pressure will result in more CO2 being dissolved into the culture medium, leading to lower pH). The partial pressure of CO2 in the cultivation device may be adjusted by changing the percentage of CO2 in the sparging gas, changing the total pressure in the cultivation device, or changing the mixing and sparging rate in the cultivation device (reducing or increasing CO2 mass transfer coefficient), or any other appropriate method. The partial pressure of CO2 in the cultivation device may be in the range of 0.05 kPa to 100 kPa, or in the range 2 kPa to 60 kPa, or in the range 5 kPa to 30 kPa.

The culture medium may comprise a shear protectant to prevent cell damage from mechanical forces caused by mixing and/or sparging in the cultivation device. As a shear protectant may be used at least one of: polyethylene glycol (PEG), methyl cellulose (MC), (hydroxypropyl)methyl cellulose (HPMC), hydroxypropyl cellulose (HPC), carboxymethyl cellulose (CMC), dextran sulfate, or any other appropriate shear protectant, or their combination. Shear protectants may be present in the culture medium in a concentration in the range of 0 g/L to 50 g/L, or in the range of 0.02 g/L to 10 g/L, or in the range of 0.1 g/L to 5 g/L.

The momentary concentration of sugars in the medium may be in the range 0.005 g/L to 40 g/L, or in the range 0.1 g/L to 20 g/L, or in the range 0.5 g/L to 5 g/L.

The momentary concentration of all amino acids (taking into account both amino acids sourced from the hydrolysate and amino acids added separately and biologically available derivatives, such as esters) and peptides in the medium may be in the range of 0.005 g/L to 30 g/L, or in the range 0.1 g/L to 15 g/L, or in the range 0.5 g/L to 10 g/L.

The composition of culture media as described above may be suitable for cell lines that have been extensively adapted to conditions in vitro. However, some cell types may require additional components in the medium, for example protein growth factors, to survive and proliferate. In another aspect of the invention, a medium composition suitable for these growth-factor dependent cell lines may be described as follows.

The hydrolyzates of plant protein isolates may be used as amino acid sources in culture media according to the invention. Recombinant protein production may be used in culture medium components preparation.

The culture medium according to the invention may comprise macronutrients and micronutrients, other components adjusting the properties of the basal medium (osmolality and availability of micronutrients) and signaling components. The components may be dissolved, for example, in purified water, or in water with inorganic salts, for example phosphate buffer saline (PBS) or water or PBS with Bovine serum albumin (BSA), for example 1% BSA in total.

The signaling compounds may vary according to the specific cell type used in the cultivation in the bioreactor. Examples of those cells may be fibroblasts, myoblasts, adipocytes and their precursors or a combination thereof.

The signaling compounds may or may not induce specific change in the cell fate. Examples of these changes may be stimulation of proliferation and/or stimulation of differentiation. The signaling compounds may be used in a certain order during a certain time period. Examples of those may be the usage of a signaling compound for stimulation of proliferation which is then in the media substituted with the signaling compound for differentiation induction. The precise order of dosing of signaling compounds may or may not be correlated or crosslinked with other tools which affect the cell fate during cultivation.

Signaling compounds for various cell types aimed for stimulation of proliferation may comprise, for example, at least one of the following signaling proteins: FGF family ligands, insulin, insulin like growth factor 1 (IGF-1), TGF family ligands, or transferrin, or any other appropriate signaling compound.

Signaling compounds for various cell types aimed for myogenic differentiation may comprise at least one of FGF, insulin, TGF, Transferrin, IGF, Epidermal growth factor (EGF), Bone morphogenic protein (BMP), Interleukin 6 (IL-6), or IL-13, or any other appropriate signaling compound.

The culture medium according to the invention may comprise amino acids (AA) or their sources, in combination with at least one type of compounds that may be selected from a group comprising: saccharides, fatty acids, vitamins and organic micronutrients, mineral compounds, for example inorganic salts, supplements, for example iron supplementation compounds, organic amines, signaling compounds, for example growth factors or signaling proteins or oligonucleotides, shear protectants, additional compounds, or compounds for manipulation, or any other appropriate compounds, or a combination thereof. The media may also contain other compounds, like phospholipids, or nucleic acids, for example. The amino acids may be sourced, for example, from a protein hydrolysate.

The amino acids and their derivatives that may be supplied to the media are for example: glycine, L-alanine, L-arginine, L-asparagine L-aspartic acid, L-cystine L-glutamic acid, L-glutamine, L-histidine, L-hydroxyproline, L-ornithine, L-citrulline, L-isoleucine, L-leucine, L-lysine, L-methionine, L-phenylalanine, L-proline, L-serine, L-threonine, L-pyroglutamic acid, L-phosphoserine, L-tryptophan, L-tyrosine or L-valine. For the preparation of the culture medium, the given amino acid may be added in the pure form, or as part of a complex mixture of compounds (for example a hydrolysate), or the hydrates or salts (for example hydrochlorides or sodium salts) of amino acids may be used.

The culture media according to present invention may comprise protein hydrolysate as a main source of amino acids. The protein hydrolysate may serve as a source of all important amino acids in culture media according to the invention for the purpose of cell cultivation, or some amino acids may be supplied to the media separately, for example L-methionine, which is found in very low concentrations in most scalable protein sources. Other different individual amino acids may be supplied separately from a different source than a protein hydrolysate.

In one aspect of the invention, the culture medium may comprise at least one of the amino acids listed in Table 4. There is also disclosed in Table 4 the possible exemplary, but not limiting, concentration of at least one amino acid that may be used in the culture medium according to the invention.

TABLE 4

| Amino Acids | Concentration mg/L |
| --- | --- |
| Glycine | 0-1875 |
| L-Alanine | 0-445 |
| L-Arginine hydrochloride | 0-14750 |
| L-Asparagine-H2O | 0-750 |
| L-Aspartic acid | 0-665 |
| L-Cysteine hydrochloride-H2O | 0-1756 |
| L-Cystine-2HCl | 0-3129 |
| L-Glutamic acid | 0-735 |
| L-Glutamine | 0-36500 |
| L-Histidine hydrochloride-H2O | 0-3148 |
| L-Isoleucine | 0-5447 |
| L-Leucine | 0-5905 |

US 12,686,847 B2

23 24

TABLE 4-continued

| Amino Acids | Concentration mg/L |
|---|---|
| L-Lysine hydrochloride | 0-9125 |
| L-Methionine | 0-1724 |
| L-Phenylalanine | 0-3548 |
| L-Proline | 0-1725 |
| L-Serine | 0-2625 |
| L-Threonine | 0-5345 |
| L-Tryptophan | 0-902 |
| L-Tyrosine disodium salt dihydrate | 0-5579 |
| L-Valine | 0-5285 |

The culture medium may comprise at least one of the following organic micronutrient compounds: spermine, spermidine, putrescine, thymidine, L-Ornithine, Ethanolamine, myo-inositol, choline and/or any other appropriate organic micronutrient compounds.

Signaling compounds, for example growth factors, may be used in the culture medium according to the invention. For example, at least one of: transferrin, insulin, FGF (for example FGF-1, FGF-2), TGF (for example TGF beta 1), IGF, or any other appropriate compounds may be used as a signaling compound.

In one aspect of the invention, the content of signaling compounds, for example content of growth factors, such as FGF, TGF beta 1, insulin or transferrin or other signaling compounds may be reduced. The concentration of TGF beta 1 may be in the range of 0 to 0.002 mg/L. The concentration of transferrin in the culture medium according to the invention may be in the range of 0 to 10 mg/L, or in the range of 0.1 to 8 mg/L, or in the range of 0.5 to 5 mg/L. In one aspect of the invention, the reduced amount of transferrin may be in the range of 0 to 0.01 mg/L The concentration of insulin in the culture medium may be in the range of 0 to 2 g/L, or in the range of 0.1 mg/L to 1 g/L, or 0.5 mg to 500 mg/L. In one aspect of the invention, the reduced amount of insulin may be in the range of 0 to 0.1 mg/L The concentration of FGF-2 in the culture medium may be in the range of 0 to 1 mg/L, or in the range of 0.1 to 0.8 mg/L, or 0.2 to 0.5 mg/L. In one aspect of the invention, the reduced amount of FGF-2 may be in the range of 0 to 0.01 mg/L.

The concentration of TGF beta 1 in the culture medium may be in the range of 0 to 0.2 mg/L, or in the range of 0.01 to 0.15 mg/L, or 0.05 to 0.1 mg/L. In one aspect of the invention, the reduced amount of TGF beta 1 may be in the range of 0 to 0.001 mg/L.

In one aspect of the invention, the culture medium may be without content of any signaling compounds, for example growth factors. The culture medium according to the invention may be serum free and/or protein free.

The culture medium may comprise anti-foaming agent, for example silicone-based anti-foaming agents, polyethylene glycol (PEG), poly vinyl alcohol (PVA), polydimethylsiloxane, polysorbate 80, or vegetable oils, or any other appropriate anti-foaming agent, or the combination thereof. The concentration of the anti-foaming agent in the culture medium may be in the range of 0.001% to 5%, or in the range of 0.01 to 1%, or in the range of 0.1 to 0.5% by weight.

In one aspect of the invention, the content of culture medium components may be in the ranges according to Table 5.

TABLE 5 ranges of concentrations of culture medium components

| Media Component | Concentration (mg/L) |
|---|---|
| Supplement | |
| Transferrin | 0-10 |
| Insulin | 0-2000 |
| FGF2 | 0-1 |
| TGF beta 1 | 0-0.2 |
| Sodium selenium | 0-1.4 |
| Ascorbate | 0-6400 |
| Sugars | |
| D-Glucose (dextrose) | 0-315100 |
| Fatty Acids | |
| Linoleic acid | 0-4.2 |
| Lipoic acid | 0-10.5 |
| Amino Acids | |
| Glycine | 0-1875 |
| L-Alanine | 0-445 |
| L-Arginine hydrochloride | 0-14750 |
| L-Asparagine-H2O | 0-750 |
| L-Aspartic acid | 0-665 |
| L-Cysteine hydrochloride-H2O | 0-1756 |
| L-Cystine-2HCl | 0-3129 |
| L-Glutamic acid | 0-735 |
| L-Glutamine | 0-36500 |
| L-Histidine hydrochloride-H2O | 0-3148 |
| L-Isoleucine | 0-5447 |
| L-Leucine | 0-5905 |
| L-Lysine hydrochloride | 0-9125 |
| L-Methionine | 0-1724 |
| L-Phenylalanine | 0-3548 |
| L-Proline | 0-1725 |
| L-Serine | 0-2625 |
| L-Threonine | 0-5345 |
| L-Tryptophan | 0-902 |
| L-Tyrosine disodium salt dihydrate | 0-5579 |
| L-Valine | 0-5285 |
| Vitamins | |
| Biotin | 0-0.35 |
| Choline chloride | 0-898 |
| D-Calcium pantothenate | 0-224 |
| Folic acid | 0-265 |
| i-Inositol | 0-1260 |
| Niacinamide | 0-202 |
| Pyridoxine hydrochloride | 0-201.3 |
| Riboflavin | 0-21.9 |
| Thiamine hydrochloride | 0-217 |
| Vitamin B12 | 0-68 |
| Inorganic Salts | |
| Calcium chloride (CaCl2) (anhyd.) | 0-11660 |
| Cupric sulphate (CuSO4—5H2O) | 0-0.13 |
| Ferric nitrate (Fe(NO3)3—9H2O) | 0-5 |
| Ferric sulphate (FeSO4—7H2O) | 0-41.7 |
| Magnesium chloride (anhyd.) | 0-2864 |
| Magnesium sulphate (MgSO4) (anhyd.) | 0-4884 |
| Potassium chloride (KCl) | 0-31180 |
| Sodium bicarbonate (NaHCO3) | 0-243800 |
| Sodium chloride (NaCl) | 0-699550 |
| Sodium phosphate dibasic (Na2HPO4) (anhyd.) | 0-7102 |
| Sodium phosphate monobasic (NaH2PO4—H2O) | 0-6250 |
| Zinc sulphate (ZnSO4—7H2O) | 0-43.2 |
| Additional compounds | |
| Hypoxanthine Na | 0-239 |
| Putrescine 2HCl | 0-8.1 |
| Sodium pyruvate | 0-5500 |
| Thymidine | 0-36.5 |

In other aspects of the invention, the culture medium may comprise signaling molecules or nucleic acids.

Nucleic Acids—Oligonucleotides

In one aspect of the invention, oligonucleotides may be used as constituent components of a culture medium for a cultivation of cells. Oligonucleotides may be with single or double stranded chains of nucleic acids containing 10 to 70 nucleotides or 10 to 120 or 1 to 1,000 nucleotides.

In one aspect of the invention, the oligonucleotides may be added to the culture medium in molar concentration in the range of 5 to 100 nM/L, or in the range of 5 to 500 nM/L, or in the range of 50 nM/L to 50 mM/L, or the concentration may vary during the cultivation, when a peak of higher concentration may be followed with the lower concentration. The peak of high concentration may be from 1-10 hours or 10-72 hours of the cultivation.

In one aspect of the invention oligonucleotides may be a one of the components of a cell type specific signaling compound or may be added to the culture medium independently to the other components.

Examples of oligonucleotides serving as AONs may be oligonucleotides whose target are mRNA of target genes. Examples of those target genes may be ferroportin, myostatin, p53, miRNA140 or others.

Examples of oligonucleotides serving as ligand to the suitable protein (aptamers) may be oligonucleotides able to bind the target proteins such as FGF-2 receptor, TGF-beta receptor, TrF receptor, insulin receptor or others.

As additional compound may be used at least one of: hypoxanthine, putrescine, pyruvate, thymidine, ethanolamine the salts or derivatives thereof, for example sodium hypoxanthine or putrescine dihydrochloride, or any other appropriate additional compound.

The hypoxanthine, for example hypoxanthine sodium, may be used in the culture medium according to the invention in the concentration in the range of 0 to 239 mg/L, or in the range of 10 to 200 mg/L, or in the range of 50 to 100 mg/L.

The putrescine, for example putrescine dihydrochloride, may be used in the culture medium according to the invention in the concentration in the range of 0 to 8.1 mg/L, or in the range of 1 to 6 mg/L, or in the range of 2 to 5 mg/L.

The pyruvate, for example pyruvate sodium, may be used in the culture medium according to the invention in the concentration in the range of 0 mg/L to 5.5 g/L, or in the range of 100 mg/L to 3 g/L, or in the range of 500 mg/L to 1 g/L.

The thymidine may be used in the culture medium according to the invention in the concentration in the range of 0 to 36.5 mg/L, or in the range of 5 to 25 mg/L, or in the range of 10 to 20 mg/L.

The recombinantly prepared signaling compounds may be used in the culture medium according to the invention. The signaling compounds may be stabilized to prevent degradation, for example thermal degradation or proteolytic degradation. They may be secreted into the culture medium, or accumulated in the cellular or subcellular compartment. Then in the process of harvesting they may be or may not be collected, purified and separated or whole culture may be collected. From the whole cultivated culture, various fractions (parts) may be divided and collected in a form of pellets that are easy to handle. Those pellets may be further processed and may serve as a direct compound to be added to the culture medium. Pellets may be dissolved, lysed or reconstituted prior the application into the culture medium in an appropriate solvent.

In one aspect of the invention, a production of recombinant signaling compounds may be used as culture medium components. The recombinant protein production may comprise the following expression systems: bacterial (for example *Escherichia coli, Bacillus subtilis*), Brewer's yeast (*Saccharomyces cerevisiae*), non-conventional yeast (for example *Pichia pastoris, Hansenula polymorpha, Yarrowia lipolytica*), filamentous fungi (for example *Aspergillus* spp., *Trichoderma reesei*), plants (for example *Nicotiana tabacum, Hordeum vulgare, Zea May*), insect cells or mammalian cell lines (for example HEK293, CHO-K1), or any other appropriate expression systems. The recombinant protein production followed by the cellular lysis and derivation of the pellets or other recombinant protein rich derivatives may be used for example in *Streptococcus thermophilus, S. cerevisiae, P. pastoris* and various strains of species *Lactobacillus* spp. such as *Lactobacillus acidophilus, Lactobacillus plantarum*, and *Lactobacillus casei*.

In one aspect of the invention, the culture medium for cell cultivation for preparing food products may have the total input of hydrolysate expressed as dry protein weight introduced into the culture medium within the cultivation process in the range of 8 g/L to 50 g/L.

The total input of amino acids from hydrolysate, including amino acids in the form of short peptides or suitable bioavailable derivatives may be at least 75% by weight of the total input of all amino acids into the culture medium.

The source of substrate for hydrolysis may be selected from at least one of: phototrophic organisms, such as land plants, green algae, red algae, brown algae, or other phototrophic eukaryotes, phototrophic prokaryotes such as cyanobacteria, or cultivated heterotrophic prokaryotes or eukaryotes, such as bacteria or yeast.

The source of substrate for hydrolysis may be selected from at least one of: soy, pea, rice, wheat, corn, fava beans, alfalfa, hemp, chickpea, potato, pumpkin, rapeseed, red lentil, Spirulina, Chlorella, sunflower, water lentil, mung bean or baker's yeast.

The source of substrate for hydrolysis may be at least one of: soy bean, fava bean, or pea.

In one aspect of the invention, the culture medium may further comprise supplemented at least one of: L-methionine, or L-cysteine, L-cystine, L-ornithine, L-tryptophan, L-histidine, L-threonine, added separately from the hydrolysate.

The total input of amino acids added to the culture medium separately from the hydrolysate may be in the range of 0.1 g/L to 10 g/L.

The total input of amino acids added to the culture medium separately from the hydrolysate may be in the range of 0.5 to 15% expressed as a percentage of the total input of hydrolysate protein into the culture medium.

The total amount of L-cysteine in culture medium may be in the range of 1 to 5% by weight with respect to the total amount of hydrolysate protein in the culture medium.

The total amount of L-ornithine in culture medium may be in the range of 0.001 to 0.5% with respect to the total amount of hydrolysate protein in the culture medium.

The total amount of L-methionine in culture medium may be in the range of 0.2 to 2% with respect to the total amount of hydrolysate protein in the culture medium.

The total amount of L-tryptophan in culture medium may be in the range of 0.2 to 2% with respect to the total amount of hydrolysate protein in the culture medium.

The total amount of L-histidine in culture medium may be in the range of 0.15 to 1.5% with respect to the total amount of hydrolysate protein in the culture medium.

The total amount of L-threonine in culture medium may be in the range of 0.3 to 3% with respect to the total amount of hydrolysate protein in the culture medium.

In one aspect of the invention, the culture medium may further comprise at least one compound from a group consisting of: vitamins, sugars, minerals, organic amines, micronutrients, iron supplementation compounds, shear protectants and low-abundance organic compounds, or a combination thereof.

The vitamin may comprise at one least of: alpha-tocopherol (vitamin E), ascorbic acid (vitamin C), vitamin B12, biotin, choline, pantothenic acid, folic acid, niacinamide, pyridoxine, riboflavin, thiamine, i-inositol, or their derivatives, or a combination thereof.

The sugar may comprise at least one of: glucose, fructose, galactose, sucrose, lactose, maltose, or a combination thereof.

The organic amine may comprise at least one of: putrescine or ethanolamine.

The micronutrient may comprise at least one of: spermine, spermidine, putrescine, thymidine, L-Ornithine, Ethanolamine, myo-inositol, or choline.

The iron supplementation compound may comprise at least one compound in oxidation state iron(III) or iron(II).

The shear protectant may comprise at least one of: polyethylene glycol (PEG), Pluronic® F68 (poloxamer 188), Pluronic® F127 (poloxamer 407), methyl cellulose (MC), (hydroxypropyl)methyl cellulose (HPMC), hydroxypropyl cellulose (HPC), carboxymethyl cellulose (CMC), or dextran sulfate, or a combination thereof.

In one aspect of the invention, the total input of vitamins per liter of culture medium, except the vitamins present in lysates or extracts, may be in the range of 20 mg/L to 300 mg/L, the total input of sugars per liter of culture medium may be in the range of 3 g/L to 20 g/L, the total input of iron per liter of culture medium may be in the range of 0.001 g/L to 0.05 g/L.

The total input of choline may be in the range of 20 mg/L to 500 mg/L.

The total input of niacinamide, or another vitamer of vitamin B3, may be in the range of 6 mg/L to 100 mg/L.

The total input of mineral compounds introduced into the cultivation process may be in the range of 1 g/L to 20 g/L.

The total input of $Na^+$ may be in the range of 30 to 100 mmol/L.

The total input of $Cl^-$ may be in the range of 35 to 110 mmol/L.

The total input of $Mg^{2+}$ is in the range of 0.5 to 8 mmol/L.

The total input of $PO_4^{3-}$ is in the range of 0.7 to 10 mmol/L.

The total input of $SO_4^{2-}$ is in the range of 0.3 to 3 mmol/L.

The total input of $K^+$ is in the range of 4 to 15 mmol/L.

The total input of the shear protectant may be in the range of 0.1 g/L to 5 g/L.

In one aspect of the invention, the culture medium may comprise exogenous signaling protein in low concentration. The concentration of exogenous signaling protein may be 0, or the concentration of exogenous signaling protein may be in the range of 0 to 50 mg/L.

The cells for cultivation may be non-human metazoan cells.

In one aspect of the invention, the cells for cultivation may be non-human vertebrate cells.

In one aspect of the invention the cells for cultivation may be selected from:

stem cells comprising embryonic stem cells (ESCs) and other cell types derived from blastocysts or other early-stage embryos;

muscle stem cells, such as myosatellite cells, mesenchymal stem cells, or cells where stem characteristics are established in vitro, such as induced pluripotent stem cells (iPSCs);

or cells with the characteristics of: myoblasts, myocytes, fibroblasts, myofibroblasts, fibro-adipogenic progenitors, preadipocytes, adipocytes, epithelial cells, chondroblasts, chondrocytes, macrophages, keratinocytes, hepatocytes, or Sertoli cells.

In one aspect of the invention the cells for cultivation may be anchorage independent, meaning that the cells are able to survive and grow in suspension conditions without attachment to any surface, and/or the cells for cultivation may be able to survive and grow as a suspension of cell clumps, cell aggregates, spheroids or organoids, or the combination thereof.

The culture medium according to the invention may be used for suspension cultivation, meaning that the cultivation process entails cultivating the cells in a stirred tank or other suitable bioreactor type, where the majority of cells is present as a suspension of single cells or cell aggregates.

In one aspect of the invention the cells for cultivation may be immortalized.

In one aspect of the invention the pH of the culture medium may be in the range of 6.8 to 7.3.

In one aspect of the invention the culture medium may comprise a source of bioavailable inorganic nitrogen, wherein the total input of inorganic nitrogen source may be in the range of 1 g/L to 10 g/L.

In one aspect of the invention the process for preparation of the culture medium may have the characteristics of continuous medium preparation, where the medium components may be introduced into the cultivation process separately, the process may comprise the following steps:

a) introduction of a concentrated basal medium into the cultivation device at a defined flow rate, wherein the basal medium is X times more concentrated than the desired concentration in the final medium and the basal medium is introduced at a flow rate 1/X times the total output flow rate from the cultivation device b) introduction of a concentrated sugar solution into the cultivation device, wherein the flow rate is controlled so that the concentration of the sugar in the cultivation medium is kept at a desirable setpoint, c) introduction of a solution of hydrolysate and amino acids into the cultivation device, wherein the flow rate is controlled so that the concentration of amino acids in the medium is kept at a desirable setpoint, d) introduction of a concentrated solution of NaCl into the cultivation device, wherein the flow rate is controlled so that the total osmolality of the medium is kept at a desirable setpoint, for example 310 mOsm/kg, e) introduction of a demineralized water into the cultivation device, wherein the flow rate is adjusted to be equal to the difference of the total output flow rate from the cultivation device and the sum of all other input flow rates, thereby keeping a constant volume of liquid in the bioreactor.

In one aspect of the invention the process for preparation of the culture medium may comprise a pH adjustment by changing the partial pressure of CO2.

In one aspect of the invention the process for preparation of the culture medium comprising protein hydrolysate may comprise the step of hydrolysis of the source of protein substrate selected from at least one of: phototrophic organisms, such as land plants, green algae, red algae, brown algae, or other phototrophic eukaryotes, phototrophic prokaryotes such as cyanobacteria, or cultivated heterotrophic prokaryotes or eukaryotes, such as bacteria or yeast, or the source of protein substrate for hydrolysis may be selected from at least one of: soy, pea, rice, wheat, corn, fava beans, alfalfa, hemp, chickpea, potato, pumpkin, rapeseed, red lentil, Spirulina, Chlorella, sunflower, water lentil, mung bean or yeast.

The concentration of protein in the reaction mixture may be 30 to 130 g/L.

In one aspect of the invention the protein substrate for hydrolysis may be subjected to an initial thermal pretreatment to improve solubility and susceptibility to hydrolysis, wherein the temperature may be in the range of 80 to 95° C. for 15 to 60 minutes.

In one aspect of the invention the process for preparation of the culture medium may comprise preparation of the protein hydrolysate by enzymatic hydrolysis, wherein the enzymes used for the hydrolysis may comprise at least one endoprotease and at least one exoprotease.

In one aspect of the invention the process for preparation of the culture medium may comprise hydrolysis using at least one of the following types of enzymes: serine protease (for example a subtilisin-like protease), cysteine protease, metalloprotease, glutamic protease or aspartic protease.

The process of preparation of the culture medium may comprise hydrolysis using at least one enzyme of: Alcalase, Flavourzyme, Protamex, Novo-Pro D, Thermoase PC10FNA, Protease AN Amano 100SD, Protease A Amano 2SD, Protease M Amano SD, Protease P Amano 6SD, ProteAX, Peptidase R, Alkaline Protease, Corolase 7089, Corolase 2TSN, Corolase 8000, Maxipro TNP, Maxipro FPC, Papain, or Bromelain.

The concentration of the enzyme may be in the range of 0.05 to 5% expressed as a ratio of the concentration of enzyme to the concentration of substrate protein in the reaction mixture.

The process of enzymatic hydrolysis may take place at a temperature in the range of 30 to 65° C. The pH may be in the range of 5 to 9 and time range may be 10 to 26 hours.

The enzyme may be immobilized on microcarriers.

In one aspect of the invention in the process for preparation of the culture medium the amount of the source protein converted into free amino acids, expressed as mass concentration of amino acids to mass concentration of protein may be in the range of 35 to 65%.

The degree of hydrolysis defined as the percentage of hydrolyzed peptide bonds out of the total amount of peptide bonds present in the substrate at the start of the hydrolysis reaction may be in the range of 20% to 50%.

In one aspect of the invention the process for preparation of the culture medium may comprise monitoring of the hydrolysis by conductometry.

In one aspect of the invention in the process for preparation of the culture medium the hydrolysate may be further processed with phytase to remove phytic acid.

In one aspect of the invention the hydrolysate may be thermally treated at the end of hydrolysis in order to deactivate enzymes and kill microorganisms.

The temperature of the thermal treatment of the hydrolysate may be in the range of 85 to 100° C. for time in the range of 20 to 120 min, or the temperature may be in the range of 100 to 155° C. for time in the range of 3 to 300 s.

In the process of cell cultivation according to the invention, the culture medium according to the description above may be used.

In one aspect of the invention, the cells used in the process of cell cultivation may be non-human metazoan cells.

In one aspect of the invention, the cells used in the process of cell cultivation may exhibit at least one of the following properties:

a) immortalization (absence of Hayflick limit), b) ability to survive and proliferate in the absence of attachment to a solid surface (anchorage independence), c) ability to synthesize glutamine, d) ability to synthesize asparagine, e) ability to synthesize proline, f) ability to survive and proliferate in the absence of growth factors, or g) ability to uptake iron in the absence of transferrin.

The culture medium according to the above mentioned description may be used for cell cultivation for the purpose of preparing the food product.

EXAMPLES

Example 1—Enzymatic Hydrolysis by Free Enzyme

Hydrolysis by free enzyme was performed in the hydrolysis tank by dissolving soy protein isolate in distilled water to a concentration of 10 g/L and the addition of Alcalase to a concentration of 0.05 g/L. The Alcalase used was supplied by Novozymes company. The resulting solution had a basic pH, allowing for a high activity of Alcalase at 62° C. Over 2 hours with constant mixing, the pH of the solution decreased as the results of the hydrolysis of peptide bonds and increased number of carboxylic groups. These conditions allowed for a high activity of Flavourzyme, which was added to a concentration of 0.15 g/L. The resulting mixture was then incubated for an additional 20 hours at 62° C. with constant mixing, after which the residual enzyme was thermally deactivated. With this procedure, 43% of the source protein was converted into free amino acids.

Results of HPLC analysis of amino acid content using UV detection (cysteine was not measured in this analysis) are summarized in Table 6.

TABLE 6

| HPLC analysis of amino acid content in hydrolysate | |
| --- | --- |
| Amino acid | mg/L |
| Asp | 136.45 |
| Glu | 253.40 |
| Asn | 388.74 |
| Ser | 248.59 |
| Gln | 170.42 |
| His | 147.57 |
| Gly | 80.27 |
| Thr | 226.47 |
| Arg | 426.90 |
| Ala | 138.12 |
| Tyr | 210.82 |
| Met | 56.30 |
| Val | 286.39 |
| Cystine | 8.46 |
| Trp | 60.30 |
| Phe | 296.79 |
| Ile | 260.56 |
| Leu | 469.37 |
| Lys | 381.21 |
| Pro | 31.25 |
| Sum | 4288.91 |

Example, 2—Enzymatic Hydrolysis by
Immobilized Enzyme

The immobilized enzymes were prepared by suspending 600 mg of $NH_2$-functionalized porous silica microbeads in 50 ml of distilled water. Silica beads were further activated with the addition of 0.003% by volume of glutaraldehyde. After 30 minutes, excess glutaraldehyde was washed away with distilled water and the silica beads were suspended in half the original volume. The Alcalase, supplied by Novozymes company, was then added to a final concentration of 0.1% with constant stirring. This procedure immobilized 80% of the used enzyme on the silica beads, corresponding to 4 grams of enzyme immobilized per 1 kilogram of silica beads.

The silica beads with immobilized Alcalase were added to a mixture of 13 g/L of a soy protein in distilled water at a density of 10 grams of beads per liter. After hydrolysis in the hydrolysis tank for 2 hours at 62° C. with constant mixing, the beads with Alcalase were removed by centrifugation and 40 grams of silica beads with immobilized Flavourzyme were added. After further hydrolysis for 20 hours at 62° C. with constant mixing, the Flavourzyme beads were removed by centrifugation and the resulting hydrolysate was thermally sterilized for 20 minutes at 130° C. and pressure of 2.5 atmospheres, which also deactivated any enzyme that may have detached from the solid support. After filtration to remove solid debris, the hydrolysate was used to prepare culture media. With this method, 5% of the source protein was converted into free amino acids.

Results of HPLC (UV detection) analysis of amino acid content (cysteine was not measured in this analysis) are summarized in Table 7.

TABLE 7

| HPLC analysis of amino acid content in hydrolysate | |
| --- | --- |
| Amino acid | Soy, water (mg/L) |
| Asp | 15.33 |
| Glu | 0.00 |
| Asn | 1.51 |
| Ser | 5.86 |
| Gln | 10.57 |
| His | 14.04 |
| Gly | 68.39 |
| Thr | 0.00 |
| Arg | 21.31 |
| Ala | 32.71 |
| Tyr | 36.01 |
| Met | 11.58 |
| Val | 36.01 |
| Cystine | 4.33 |
| Trp | 8.08 |
| Phe | 123.73 |
| Ile | 33.87 |
| Leu | 204.85 |
| Lys | 51.05 |
| Pro | 1.35 |
| Sum | 680.59 |

Example 3—Culture Media Composition

The culture media have been prepared with the compositions according to the table 8 and table 9.

TABLE 8

| example total input of relevant compounds into the culture medium according to the invention. | | |
| --- | --- | --- |
| Compound | category | concentration in media [mg/L] |
| Biotin | vitamins and low-abundance organic compounds | 0.0035 |
| Choline chloride | vitamins and low-abundance organic compounds | 8.9800 |
| D-Calcium pantothenate | vitamins and low-abundance organic compounds | 2.2400 |
| Folic Acid | vitamins and low-abundance organic compounds | 2.6500 |
| Niacinamide | vitamins and low-abundance organic compounds | 2.0200 |
| Pyridoxine hydrochloride | vitamins and low-abundance organic compounds | 2.0130 |
| Riboflavin | vitamins and low-abundance organic compounds | 0.2190 |
| Thiamine hydrochloride | vitamins and low-abundance organic compounds | 2.1700 |
| Vitamin B12 | vitamins and low-abundance organic compounds | 0.6800 |
| i-Inositol | vitamins and low-abundance organic compounds | 12.6000 |
| Calcium Chloride ($CaCl_2$) (anhydrous) | mineral compounds | 116.6000 |
| Cupric sulfate ($CuSO_4 \cdot 5H_2O$) | mineral compounds | 0.0800 |
| Ferric Nitrate ($Fe(NO_3)_3 \cdot 9H_2O$) | mineral compounds | 0.0500 |
| Ferrous sulfate ($FeSO_4 \cdot 7H_2O$) | mineral compounds | 0.4170 |
| Magnesium Chloride (anhydrous) | mineral compounds | 28.6400 |
| Magnesium Sulfate ($MgSO_4$) (anhydrous) | mineral compounds | 48.8400 |
| Potassium Chloride (KCl) | mineral compounds | 311.8000 |
| Sodium Bicarbonate ($NaHCO_3$) | mineral compounds | 2,438.0000 |
| Sodium Chloride (NaCl) | mineral compounds | 6,995.5000 |
| Sodium Phosphate dibasic ($Na_2HPO_4$) (anhydrous) | mineral compounds | 71.0200 |
| Sodium Phosphate monobasic ($NaH_2PO_4 \cdot H_2O$) | mineral compounds | 62.5000 |
| Zinc sulfate ($ZnSO_4 \cdot 7H_2O$) | mineral compounds | 0.4320 |
| Sodium selenite | mineral compounds | 0.0300 |
| Soy protein enzymatic hydrolysate (expressed as protein dry mass) | amino acids | 1,000.0000 |
| Ferric citrate | iron supplementation | 120.0000 |
| Glucose | sugars | 3150.0000 |
| Putrescine | organic amines | 1.0000 |
| Ethanolamine | organic amines | 3.0000 |

TABLE 9

| example momentary composition of relevant compounds in the culture medium according to the invention | | |
|---|---|---|
| Compound | category | concentration in media [mg/L] |
| Biotin | vitamins and low-abundance organic compounds | 0.0035 |
| Choline chloride | vitamins and low-abundance organic compounds | 8.9800 |
| D-Calcium pantothenate | vitamins and low-abundance organic compounds | 2.2400 |
| Folic Acid | vitamins and low-abundance organic compounds | 2.6500 |
| Niacinamide | vitamins and low-abundance organic compounds | 2.0200 |
| Pyridoxine hydrochloride | vitamins and low-abundance organic compounds | 2.0130 |
| Riboflavin | vitamins and low-abundance organic compounds | 0.2190 |
| Thiamine hydrochloride | vitamins and low-abundance organic compounds | 2.1700 |
| Vitamin B12 | vitamins and low-abundance organic compounds | 0.6800 |
| i-Inositol | vitamins and low-abundance organic compounds | 12.6000 |
| Calcium Chloride (CaCl$_2$) (anhydrous) | mineral compounds | 116.6000 |
| Cupric sulfate (CuSO$_4$•5H$_2$O) | mineral compounds | 0.0800 |
| Ferric Nitrate (Fe(NO$_3$)$_3$•9H$_2$O) | mineral compounds | 0.0500 |
| Ferrous sulfate (FeSO$_4$•7H$_2$O) | mineral compounds | 0.4170 |
| Magnesium Chloride (anhydrous) | mineral compounds | 28.6400 |
| Magnesium Sulfate (MgSO$_4$) (anhydrous) | mineral compounds | 48.8400 |
| Potassium Chloride (KCl) | mineral compounds | 311.8000 |
| Sodium Bicarbonate (NaHCO$_3$) | mineral compounds | 2,438.0000 |
| Sodium Chloride (NaCl) | mineral compounds | 6,995.5000 |
| Sodium Phosphate dibasic (Na$_2$HPO$_4$) (anhydrous) | mineral compounds | 71.0200 |
| Sodium Phosphate monobasic (NaH$_2$PO$_4$•H$_2$O) | mineral compounds | 62.5000 |
| Zinc sulfate (ZnSO$_4$•7H$_2$O) | mineral compounds | 0.4320 |
| Sodium selenite | mineral compounds | 0.0300 |
| Soy protein enzymatic hydrolysate (expressed as protein dry mass) | amino acids | 1,000.0000 |
| Ferric citrate | iron supplementation | 120.0000 |
| Glucose | sugars | 3150.0000 |
| Putrescine | organic amines | 1.0000 |
| Ethanolamine | organic amines | 3.0000 |

Example 4—Culture Medium Batch Mixing

Medium components for batch mixing were prepared. Solution 1 comprising vitamins and micronutrient components was prepared by dissolving the compounds according to table 10 in distilled water, so that the final volume of the solution was 10 L.

TABLE 10

| Compound | mg |
|---|---|
| Biotin | 3.5 |
| Choline chloride | 8980 |
| D-Calcium pantothenate | 2240 |
| Folic Acid | 2650 |
| Niacinamide | 2020 |
| Pyridoxine hydrochloride | 2013 |
| Riboflavin | 219 |
| Thiamine hydrochloride | 2170 |
| Vitamin B12 | 680 |
| i-Inositol | 12600 |
| Cupric sulfate (CuSO$_4$•5H2O) | 80 |
| Ferric Nitrate (Fe(NO$_3$)$_3$•9H$_2$O) | 50 |
| Sodium selenite | 30 |
| Ferric citrate | 120000 |
| Putrescine | 1200 |
| Ethanolamine | 3200 |

Solution 2 (Basal solution) was prepared by dissolving compounds according to table 11 in distilled water, so that the final volume of the solution was 80 L.

TABLE 11

| Compound | g |
|---|---|
| Calcium Chloride (CaCl2) (anhydrous) | 116.6 |
| Ferrous sulfate (FeSO4,7H2O) | 0.417 |
| Magnesium Chloride (anhydrous) | 28.64 |
| Magnesium Sulfate (MgSO4) (anhydrous) | 48.84 |
| Potassium Chloride(KCl) | 311.8 |
| Sodium Bicarbonate (NaHCO3) | 2438 |
| Sodium Chloride (NaCl) | 6995 |
| Sodium Phosphate dibasic (Na2HPO4) (anhydrous) | 71.02 |
| Sodium Phosphate monobasic (NaH2PO4,H2O) | 62.5 |
| Zinc sulfate (ZnSO4,7H2O) | 0.432 |
| Glucose | 3150 |

Hydrolysate—10 liters of soy protein hydrolysate with a protein concentration of 10 g/L was prepared according to a suitable hydrolysis procedure, as is described in the chapter on hydrolysate preparation, for example as is described in Example 1.

Media components were mixed: 1 liter of solution 1, 80 liters of solution 2 and 10 liters of hydrolysate were mixed in a 120 L mixing tank.

The pH of the solution was adjusted to 7.2, using 1 M NaOH or 1 M HCl.

Total volume of the solution was adjusted to 100 L using distilled water.

Final media solution was filtered through 0.1 μm candle filters. The sterile medium was stored in a sterile storage tank, which was directly connected to a cultivation device.

Example 5—Culture Medium Continuous Mixing

Five medium component solutions were prepared (hydrolysate was prepared according to the procedure for preparation of hydrolysate, other solutions were prepared by dissolving the components in distilled water at the required concentration).

Basal medium solution was prepared with the composition according to table 12.

TABLE 12

| Compound | mg/L |
|---|---|
| Biotin | 0.0105 |
| Choline chloride | 26.94 |
| D-Calcium pantothenate | 6.72 |
| Folic Acid | 7.95 |
| Niacinamide | 6.06 |
| Pyridoxine hydrochloride | 6.039 |
| Riboflavin | 0.657 |
| Thiamine hydrochloride | 6.51 |
| Vitamin B12 | 2.04 |
| i-Inositol | 37.8 |
| Calcium Chloride (CaCl2) (anhydrous) | 349.8 |
| Cupric sulfate (CuSO4,5H2O) | 0.24 |
| Ferric Nitrate (Fe(NO3)3,9H2O) | 0.15 |
| Ferrous sulfate (FeSO4,7H2O) | 1.251 |
| Magnesium Chloride (anhydrous) | 85.92 |
| Magnesium Sulfate (MgSO4) (anhydrous) | 146.52 |
| Potassium Chloride (KCl) | 935.4 |
| Zinc sulfate (ZnSO4,7H2O) | 1.296 |
| Sodium selenite | 0.09 |
| Ferric citrate | 360 |
| Putrescine | 3.6 |
| Ethanolamine | 9.6 |

Buffer solution was prepared with the composition according to table 13.

TABLE 13

| Compound | mg/L |
|---|---|
| Sodium Bicarbonate (NaHCO3) | 24380 |
| Sodium Phosphate dibasic (Na2HPO4) (anhydrous) | 710.2 |
| Sodium Phosphate monobasic (NaH2PO4,H2O) | 625 |

Further the soy protein hydrolysate solution was prepared with the concentration of protein of 10 g/L.

Sugar solutions were prepared with the composition according to table 14.

TABLE 14

| Compound | mg/L |
|---|---|
| Glucose | 63000 |

Salt solutions were prepared with the composition according to table 15.

TABLE 15

| Compound | mg/L |
|---|---|
| Sodium Chloride (NaCl) | 139900 |

All component solutions were prepared in individual mixing tanks and equilibrated to a pH of 7.2, using a 1 M solution of NaOH or a 1 M solution of HCl.

All components were filtered into individual sterile storage tanks, using 0.1 μm candle filters.

The sterile medium components were introduced into the cultivation device at volumes of, in order, 0.33, 0.1, 0.1, 0.05 and 0.05 times the working volume of the cultivation device per day (vvd). Additionally, sterile distilled water is introduced into the cultivation device at 0.37 (vvd).

Example 6: Culture Medium Composition

The culture medium for cultivation of cells was prepared comprising the following types of media components:

a) signaling compounds b) basal medium compounds c) nutritional compounds.

The concentrated stock solutions of these three types of media components were prepared and stored individually. Final culture medium was prepared by mixing them together prior to the cultivation of cells in the final concentration per liter according to requested concentration.

One example of the culture media composition is according to Table 16. This culture medium composition comprises nutritional mixture of soy protein hydrolysate, fatty acids and saccharides combined with vitamins, inorganic salts, additional compounds and growth factors.

TABLE 16

| medium composition | |
|---|---|
| Media Component | Concentration (mg/L) |
| Growth factors | |
| Transferrin | 0.100 |
| Insulin | 20.000 |
| FGF2 | 0.100 |
| TGF beta 1 | 0.002 |
| Saccharides | |
| D-Glucose (dextrose) | 3 151.000 |
| Fatty Acids | |
| Linoleic acid | 0.042 |
| Lipoic acid | 0.105 |
| Nutritional mix | |
| soy hydrolysate | 10 000 |
| Vitamins | |
| Biotin | 0.004 |
| Choline chloride | 8.980 |
| D-Calcium pantothenate | 2.240 |
| Folic acid | 2.650 |
| i-Inositol | 12.600 |
| Niacinamide | 2.020 |
| Pyridoxine hydrochloride | 2.013 |
| Riboflavin | 0.219 |
| Thiamine hydrochloride | 2.170 |
| Vitamin B12 | 0.680 |
| Ascorbate | 64.000 |
| Inorganic Salts | |
| Sodium selenium | 0.014 |
| Calcium chloride (CaCl2) (anhyd.) | 116.600 |
| Cupric sulfate (CuSO4—5H2O) | 0.001 |
| Ferric nitrate (Fe(NO3)3—9H2O) | 0.050 |
| Ferric sulfate (FeSO4—7H2O) | 0.417 |
| Magnesium chloride (anhyd.) | 28.640 |
| Magnesium sulfate (MgSO4) (anhyd.) | 48.840 |
| Potassium chloride (KCl) | 311.800 |
| Sodium bicarbonate (NaHCO3) | 2 438.000 |
| Sodium chloride (NaCl) | 6 995.500 |
| Sodium phosphate dibasic (Na2HPO4) (anhyd.) | 71.020 |
| Sodium phosphate monobasic (NaH2PO4—H2O) | 62.500 |
| Zinc sulfate (ZnSO4—7H2O) | 0.432 |
| Additional compounds | |
| Hypoxanthine Na | 2.390 |
| Putrescine 2HCl | 0.081 |
| Sodium pyruvate | 55.000 |
| Thymidine | 0.365 |

TABLE 17

| culture medium composition | |
|---|---|
| Media Component | Concentration (mg/L) |
| Growth factors | |
| Transferrin | 0.100 |
| Insulin | 20.000 |
| FGF2 | 0.100 |
| TGF beta 1 | 0.002 |
| LIF | 0.050 |
| Saccharides | |
| D-Glucose (dextrose) | 1 000.000 |
| Amino Acids | |
| Glycine | 18.750 |
| L-Alanine | 4.450 |
| L-Arginine hydrochloride | 147.500 |
| L-Asparagine-H2O | 7.500 |
| L-Aspartic acid | 6.650 |
| L-Cysteine hydrochloride-H2O | 17.560 |
| L-Cystine-2HCl | 31.290 |
| L-Glutamic acid | 7.350 |
| L-Glutamine | 365.000 |
| L-Histidine hydrochloride-H2O | 31.480 |
| L-Isoleucine | 54.470 |
| L-Leucine | 59.050 |
| L-Lysine hydrochloride | 91.250 |
| L-Methionine | 17.240 |
| L-Phenylalanine | 35.480 |
| L-Proline | 17.250 |
| L-Serine | 26.250 |
| L-Threonine | 53.450 |
| L-Tryptophan | 9.020 |
| L-Tyrosine disodium salt dihydrate | 55.790 |
| L-Valine | 52.850 |
| Fatty Acids | |
| Linoleic acid | 0.042 |
| Lipoic acid | 0.105 |
| Vitamins | |
| Biotin | 0.004 |
| Choline chloride | 8.980 |
| D-Calcium pantothenate | 2.240 |
| Folic acid | 2.650 |
| i-Inositol | 12.600 |
| Niacinamide | 2.020 |
| Pyridoxine hydrochloride | 2.013 |
| Riboflavin | 0.219 |
| Thiamine hydrochloride | 2.170 |
| Vitamin B12 | 0.680 |
| Ascorbate | 64.000 |
| Inorganic Salts | |
| Sodium selenium | 0.014 |
| Calcium chloride (CaCl2) (anhyd.) | 116.600 |
| Cupric sulfate (CuSO4—5H2O) | 0.001 |
| Ferric nitrate (Fe(NO3)3—9H2O) | 0.050 |
| Ferric sulfate (FeSO4—7H2O) | 0.417 |
| Magnesium chloride (anhyd.) | 28.640 |
| Magnesium sulfate (MgSO4) (anhyd.) | 48.840 |
| Potassium chloride (KCl) | 311.800 |
| Sodium bicarbonate (NaHCO3) | 2 438.000 |
| Sodium chloride (NaCl) | 6 995.500 |
| Sodium phosphate dibasic (Na2HPO4) (anhyd.) | 71.020 |
| Sodium phosphate monobasic (NaH2PO4—H2O) | 62.500 |
| Zinc sulfate (ZnSO4—7H2O) | 0.432 |
| Additional compounds | |
| Hypoxanthine Na | 2.390 |
| Putrescine 2HCl | 0.081 |
| Sodium pyruvate | 55.000 |
| Thymidine | 0.365 |

Another example of the culture media composition is according to Table 17. This culture medium composition comprises nutritional mixture of raw food grade amino acids, fatty acids and saccharide D-glucose combined with vitamins, inorganic salts, additional compounds and growth factors.

The culture medium according to the invention may be suitable for cell cultivation, for example in cultivated meat production or pet food production. The advantageous processes of culture media preparation and the process of protein hydrolysis into shorter peptide chains and/or single amino acids are also provided by the present invention.

The invention claimed is:

1. A culture medium for the cultivation of cells comprising, a protein hydrolysate as a source of amino acids, wherein the protein hydrolysate is prepared by enzymatic hydrolysis of a protein substrate, wherein the cells are non-human metazoan cells, and wherein a total input of amino acids from the protein hydrolysate, including amino acids in the form of peptides or suitable bioavailable derivatives, is at least 75% by weight of a total input of all amino acids in the culture medium;

wherein a total input of the protein hydrolysate expressed as dry protein weight introduced into the culture medium is in the range of 8 g/L to 50 g/L.

2. The culture medium according to claim 1, wherein a total input of amino acids added to the culture medium separately from the protein hydrolysate is in a range of 0.1 g/L to 10 g/L.

3. The culture medium according to claim 1, wherein the protein substrate for the protein hydrolysate comprises at least one of soy, pea, rice, wheat, corn, fava beans, alfalfa, hemp, chickpea, potato, pumpkin, rapeseed, red lentil, *Spirulina*, *Chlorella*, sunflower, water lentil, mung bean, or baker's yeast.

4. The culture medium according to claim 1, further comprising one or more of vitamins, sugars, minerals, organic amines, micronutrients, iron supplementation compounds, or shear protectants.

5. The culture medium according to claim 1, further comprising at least one exogenous signaling protein, wherein the exogenous signaling protein has a concentration of up to 50 mg/L in the culture medium.

6. The culture medium according to claim 1, further comprising a source of bioavailable inorganic nitrogen, wherein a total input of the source of bioavailable inorganic nitrogen is in the range of 1 g/L to 10 g/L.

7. The culture medium according to claim 1, wherein the protein hydrolysate is thermally treated at the end of hydrolysis to deactivate enzymes and kill microorganisms.

8. The culture medium according to claim 1, wherein a total input of the protein hydrolysate expressed as a percentage of the total input of protein hydrolysate into the culture medium is in a range of 0.2% to 25%.

9. A culture medium for the cultivation of cells comprising:

a protein hydrolysate as a source of amino acids, wherein the protein hydrolysate is prepared by an enzymatic hydrolysis of a source protein substrate, wherein the cells are non-human metazoan cells, wherein a total input of supplemented amino acids, added to the culture medium separately from the protein hydrolysate, is in a range of 0.1 g/L to 10 g/L.

10. The culture medium according to claim 9, wherein the culture medium comprises at least one essential amino acid, wherein a highest possible conversion efficiency for essential total amino acids is in a range of 30% to 100%, as calculated by equation (1):

$$H_{EAA} = \frac{\dfrac{A_{EAAM}}{\sum A_{EAAM}}}{\dfrac{A_{EAAC}}{\sum A_{EAAC}}} * 100, \qquad (1)$$

where $H_{EAA}$ is the highest possible conversion efficiency for a particular amino acid, $A_{EAAM}$ is the content of the particular essential amino acid in 100 g of protein in the culture medium, $\sum A_{EAAM}$ is a total content of all essential amino acids in 100 g of protein in the culture medium, $A_{EAAC}$ is the content of the particular essential amino acid in 100 g of cellular protein, and wherein the concentrations of amino acids in grams per 100 grams of total essential amino acids introduced into the cultivation process is 0.3 g to 6.04 g for His, 0.57 g to 11.41 g for Ile, 1.00 g to 19.91 g for Leu, 0.92 g to 18.34 g for Lys, 0.32 g to 6.49 g for Met, 0.53 g to 10.51 g for Phe, 0.54 g to 10.74 g for Thr, 0.18 g to 3.58 g for Trp, 0.65 g to 12.98 g for Val; and wherein the highest possible conversion efficiency is determined by the most limiting essential amino acid.

11. The culture medium according to claim 9, further comprising a supplemented amino acid comprising at least one of: L-methionine, L-cysteine, L-cystine, L-ornithine, L-tryptophan, L-histidine, or L-threonine, added separately from the protein enzymatic hydrolysate.

12. The culture medium according to claim 11, wherein the total input of the protein hydrolysate expressed as dry protein weight introduced into the culture medium is in a range of 8 g/L to 50 g/L.

13. The culture medium according to claim 9, further comprising at least one of: vitamins, sugars, minerals, organic amines, micronutrients, iron supplementation compounds, or shear protectants.

14. The culture medium according to claim 13, wherein the culture medium comprises an organic amine, wherein the organic amine is at least one of putrescine or ethanolamine.

15. The culture medium according to claim 13, wherein the culture medium comprises a micronutrient, wherein the micronutrient comprises at least one of: spermine, spermidine, putrescine, thymidine, L-ornithine, ethanolamine, myo-inositol, or choline.

16. The culture medium according to claim 13, wherein the culture medium comprises at least one iron supplementation compound, wherein the at least one iron supplementation compound comprises iron in oxidation state iron (III) or iron (II).

17. The culture medium according to claim 13, wherein the culture medium comprises a shear protectant, wherein the shear protectant comprises at least one of: polyethylene glycol (PEG), methyl cellulose (MC), (hydroxypropyl)methyl cellulose (HPMC), hydroxypropyl cellulose (HPC), carboxymethyl cellulose (CMC), or dextran sulfate.

18. A culture medium for the cultivation of cells, comprising a protein hydrolysate as a source of amino acids, wherein the protein hydrolysate is prepared by an enzymatic hydrolysis of a protein substrate, wherein the cells are non-human metazoan cells, wherein a total input of protein hydrolysate, expressed as dry protein weight introduced into the culture medium is in a range of 8 g/L to 50 g/L.

19. The culture medium according to claim 18, wherein the enzymatic hydrolysis occurs in a hydrolysis reaction mixture comprising the enzymes and the protein substrate, wherein a total enzyme concentration in the hydrolysis reaction mixture is in a range of 0.05 to 5% expressed as a ratio of the concentration of the enzymes in the hydrolysis reaction mixture to the concentration of the protein substrate in the hydrolysis reaction mixture.

20. The culture medium according to claim 18, wherein a degree of the enzymatic hydrolysis of the protein substrate, defined as a percentage of hydrolyzed peptide bonds out of a total amount of peptide bonds present in the substrate at the start of the hydrolysis reaction, is in a range of 10% to 60%.

21. The culture medium according to claim 18, wherein the cells are anchorage independent, defined as being able to survive and grow in suspension conditions without attachment to any surface, and/or the cells are able to survive and grow as a suspension of cell clumps, cell aggregates, spheroids, or organoids.

22. The culture medium according to claim 18, wherein the concentration of protein in the reaction mixture of hydrolysis is in a range of 30 g/L to 130 g/L.

23. The culture medium according to claim 18, wherein an amount of the amino acid source in a range of 20% to 100% is converted during hydrolysis into free amino acids and short peptides smaller than 500 Da.

24. A method for preparing a culture medium for the cultivation of cells comprising:

comprising providing a protein hydrolysate as a source of amino acids, wherein the protein hydrolysate is prepared by enzymatic hydrolysis of a protein substrate, adding the protein hydrolysate to the culture medium in an amount, expressed as dry protein weight, in a range of 8 g/L to 50 g/L; and wherein a total input of amino acids from the protein hydrolysate, including amino acids in the form of peptides, bioavailable derivatives, or a combination thereof, is at least 75% by weight of a total input of all amino acids in the culture medium;

wherein the cells are non-human metazoan cells.

25. The method for preparing a culture medium according to claim 24, wherein at least two types of enzymes are used for the enzymatic hydrolysis, wherein the at least two types of enzymes comprise:

i) at least one endoprotease and at least one exoprotease, or ii) at least one of the following types of enzymes: serine protease, cysteine protease, metalloprotease, glutamic protease, or aspartic protease.

26. The method for preparing the culture medium according to claim 24, wherein the culture medium has an osmolality in a range of 200 mOsm/kg to 400 mOsm/kg.

27. The method for preparation of the culture medium according to claim 24, wherein the enzymatic hydrolysis of the protein substrate occurs in a hydrolysis reaction mixture comprising the protein substrate and an enzyme, wherein the protein substrate is at a concentration in a range of 30 g/L to 130 g/L.

28. The method for preparation of the culture medium according to claim 24, wherein the culture medium is further filtered using a filter having a pore size in a range of 0.001 μm to 10 μm.

29. The method for preparation of the culture medium according to claim 24, wherein the protein substrate is subjected to an initial thermal pretreatment to improve solubility and susceptibility to hydrolysis; wherein a temperature of the initial thermal pretreatment is in a range of 75° C. to 95° C. for a duration in a range of 5 minutes to 120 minutes.

30. The method for preparation of the culture medium according to claim 24, wherein the protein substrate is further enzymatically treated by a phytase enzyme.

\* \* \* \* \*